(12) United States Patent
Bombrun

(10) Patent No.: US 6,306,870 B1
(45) Date of Patent: Oct. 23, 2001

(54) N-CINNAMOYL DERIVATIVES OF BETA-CARBOLINE

(75) Inventor: Agnes Bombrun, Paris (FR)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 09/592,514

(22) Filed: Jun. 12, 2000

Related U.S. Application Data

(63) Continuation-in-part of application No. 09/155,811, filed as application No. PCT/EP96/02277 on May 5, 1997, now Pat. No. 6,117,881.

(30) Foreign Application Priority Data

May 10, 1996 (GB) .................................................. 9609777
May 10, 1996 (GB) .................................................. 9609820

(51) Int. Cl.$^7$ ........................ A61K 31/44; A61K 31/435; C07D 471/04; C07D 265/06
(52) U.S. Cl. ........................ 514/292; 514/277; 514/290; 514/291; 546/80; 546/84; 546/87; 544/106
(58) Field of Search .................................. 514/292, 277, 514/290, 291; 546/80, 84, 87; 544/106

(56) References Cited

U.S. PATENT DOCUMENTS

| | | |
|---|---|---|
| 3,644,384 | 2/1972 | Schulenberg ...................... 296/295 C |
| 3,717,638 | 2/1973 | Schulenberg ................... 260/268 PC |
| 3,917,599 | 11/1975 | Saxena et al. ................. 260/268 PC |
| 4,188,390 | 2/1980 | Campbell .............................. 424/251 |
| 4,686,228 | 8/1987 | Campbell et al. .................... 514/307 |
| 5,145,852 | 9/1992 | Virag .................................... 514/253 |
| 5,270,323 | 12/1993 | Milne, Jr. et al. ................... 514/309 |

(List continued on next page.)

FOREIGN PATENT DOCUMENTS

| | | | |
|---|---|---|---|
| 344 577 A3 | 6/1989 | (EP) | ............................. C07D/233/61 |
| 0 357 122 | 7/1990 | (EP) | ............................. C07D/471/04 |
| 0 362 555 | 11/1990 | (EP) | ............................. C07D/241/08 |
| 459 666 | 12/1991 | (EP) | ............................. A61K/31/505 |

(List continued on next page.)

OTHER PUBLICATIONS

A. Bowman et al., *Br. J. Pharmac.*, (1984), 81, 665–674.
F. Trigo–Rocha et al., *Am. J. Physiol.*, (Feb. 1993), 264, H419–H422.
J. Reiser et al., *Br. J. Dis. Chest*, (1986), 80, 157–163.
P. Bush et al., *J. Urol.*, (Jun. 1992), 147, 1650–1655.
F. Holmquist et al., *J. Urol.* (Oct. 1993), 150, 1310–1315.
R. Rudd et al., *Br. J. Dis. Chest*, (1983), 77, 78–86.
E. McMahon et al., *J. Pharmacol. Exp. Thera.*, (1989), 251, 1000–1005.
F. Holmquist et al., *Acta Physiol. Scand.*, (1991), 143, 299–304.
G. Barbanti, *Urol. Res.*, (1988), 16, 299–302.
L. Ignarro et al., *Biochem. and Biophys. Res. Comm.*, (1990), 170(2), 843–850.
J. Krall et al., *Bio. Reprod.*, (1988), 39, 913–922.
M. Wilkins et al., *Proc. Natl. Acad. Sci., USA*, (Aug. 1990), 87, 6465–6469.
M. Wilkins et al., *J. Clin. Invest.*, (Apr. 1990), 85, 1274–1279.
J. Rajfer, *N. Eng. J. Med.*, (Jan. 1992), 326(2), 90–94.
H. Knispel, *Urol. Res.*, (1992), 20, 253–257.
G. Gwinup, *Annals. of Internal Medicine*, (Jul. 1988), 162–163.
A. Zorgniotti, *J. Urol.*, (Apr. 1992), 147(4), 308A.
K. Azadzoi et al., *J. Urol.*, (Nov. 1992), 148, 1587–1591.
K. Azadzoi et al., *J. Urol.*, (Jan. 1992), 147, 220–225.
C. Sparwasser et al., *J. Urol.*, (Dec. 1994), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs," Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharmacol.*, (1986), 35:10, 1743–1751.
J. Doremieux et al., *Ann. Urol. Paris*, (1987), 21(6), 429–434.
D. Green et al., *Geriatrics*, (Jan. 1993), 48(1), 46–58.
M. Webster et al., *Hematol. Oncol. Cl. of N. Am.*, (Feb. 1990), 4(1), 265–289.
F. Holmquist et al., *Acta. Physiol. Scand.*, (1991), 141, 441–442.

(List continued on next page.)

*Primary Examiner*—Alan L. Rotman
*Assistant Examiner*—Rita Desai
(74) *Attorney, Agent, or Firm*—Marshall, Gerstein & Borun

(57) ABSTRACT

Carboline derivatives of formula (I), are potent and selective inhibitors of cyclic guanosine 3',5'-monophoshate specific phosphodiesterase (cGMP specific PDE) and have utility in a variety of therapeutic areas where such inhibition is thought to be beneficial, including the treatment of cardivascular disorders.

(I)

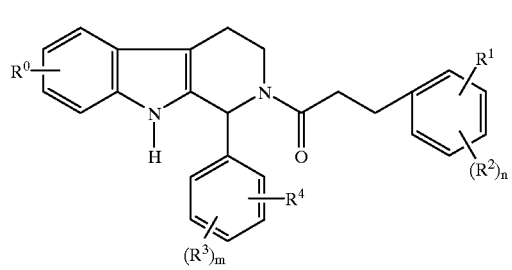

22 Claims, No Drawings

U.S. PATENT DOCUMENTS

| | | | |
|---|---|---|---|
| 5,874,437 | 2/1999 | Garvey et al. | 514/258 |
| 6,043,252 * | 3/2000 | Bombrun | 514/292 |
| 6,117,881 * | 9/2000 | Bombrun | 514/292 |

FOREIGN PATENT DOCUMENTS

| | | | |
|---|---|---|---|
| 463 756 | 1/1992 | (EP) | C07D/487/04 |
| 526 004 | 2/1993 | (EP) | C07D/487/04 |
| 1454171 | 10/1976 | (GB) | C07D/471/14 |
| 03044324 A | 2/1991 | (JP) | A61K/31/52 |
| WO 89/10123 | 2/1989 | (WO) | A61K/31/35 |
| WO 94/05661 | 3/1994 | (WO) | C07D/471/04 |
| WO 94/28902 | 12/1994 | (WO) | A61K/31/505 |
| WO 95/19978 | 7/1995 | (WO) | C07D/471/14 |

OTHER PUBLICATIONS

J. Taher et al., *J. Urol.*, (Apr. 1993), 149, 285A.
S. Uckert et al., *J. Urol.*, 151 (5 Supp.), (1994), 495A.
W. Aronson et al., *J. Urol.*, (1991), 145 (4 Supp.), 341A.
P. Bush et al., *Fed. Am. Soc. Exp. Biol.*, (1991), 5(4), 175.
P. Bush et al., *Fed. Am. Soc. Exp. Biol.*, (1992), 6(4), 2092.
W. Aronson et al., *J. Urol.*, (1992), 147 (4 Supp.), 454A.
P. Bush et al., *Circulation*, (May 1993), 87 Supp. V, V–30–V–32.
R. Pickard et al., *J. Urol.*, (May 1993) 149 (4 Supp.), 245A.
R. Pickard et al., *Clin. Pharmacol.*, (Jan. 1993), 35(5), 536P–537P.
F. Trigo–Rocha et al., *J. Urol.*, (Apr. 1993), 149, 872–877.
M. Krupp et al., *J. Cardiovas. Pharmacol.*, (1989), 13 (Supp. 2), S11–S19.
"Physicians' Desk Reference," (1992), 683, 1099–1100, 1344, 1941–1943.
R. Morales et al., *World J. Urol.*, (1990), 8, 80–83.
J. Cortijo, *Br. J. Pharmacol.*, (Feb. 1993), 108(2), 562–568.
E. Kim et al., *J. Urol.*, (1995), 153, 361–365.
S. Korenman et al., *JAGS*, (Apr. 1993), 41(4), 363–366.
K. Allenby et al., *Angiology*, (1991), 42, 418–420.
H. Hamilton et al., *J. Med. Chem.*, (1987), 30, 91–96.
H. Padma–Nathan et al., *Sem. in Urol.*, (Nov. 1986), vol. IV, No.4, 236–238.
J. Beavo et al., *TiPS*, (Apr. 1990), 11, 150–155.
S. Korenman et al., *Clin. Res.*, (1988), 36, 123A.
D. Halsted et al., *J. Urol.*, (Jul. 1986), 136, 109–110.
W. Thompson, *Pharmac. Ther.*, (1991), 51, 13–33.
M. Giembycz et al., *Clin. and Exper. Allergy*, (1992), 22, 337–344.
C. Nicholson et al., *TIPS*, (Jan. 1991), 12, 19–27.
J. LeBlanc et al., *Eur. J. Cardiothorac Surg.*, (1993), 7, 211–215.
C. Stief et al., *J. Urol.*, (Nov. 1992), 148, 1437–1440.
C. Stief et al., *World J. Urol.*, (1991), 9, 237–239.
C. Clyne et al., *Br. J. Surg.*, (Apr. 1987), 74, 246–248.
V. Mirone et al., *Acta. Urol. Ltd.*, (1992), Suppl. 4, 11–12.
P. Bush, Ph.D. Thesis (1992), pp. 159–160.
T. Lincoln, *Pharmac. Ther.*, (1989), 41, 479–502.
J. Heaton et al., *Urology*, (Feb. 1995), 45(2), 200–206.
Saxena et al., *Journal of Medicinal Chemistry*, vol. 16, No. 5, 560–564 (1973).
Ishida et al., *Chem. Pharm. Bull.*, vol. 33, No. 8, 3237–3249 (1985).
Gillespie et al., *Molecular Pharmacology*, 36:773–781 (1989).
Braña et al., *Synthetic Communications*, 20(12), 1793–1820 (1990).

Dellouve–Courillon et al., *Tetrahedron*, 46, No. 9, 3245–3266 (1990).

Murray, *DN&P* 6(3), 150–156 (1993).

Zorgniotti et al. *Int. J. Impotence Res.*, 6, 33–36 (1994).

Beyer et al., *Phys. and Behav.*, (1981), 27, 731–733.

Pickard et al., *Br. J. Pharmacol.*, (1991), 104 755–759.

Martinez–Pineiro et al., *Eur. Urol.*, (1993), 24, 492–499.

Mirone et al., *Br. J. Urol.*, (Mar., 1993), 71(3), 365.

Murray et al., *Biochemical Soc. Trans.*, (1992), 20, 460–464.

Raeburn et al., *Prog. Drug. Res.*, (1993), 12–32.

Merkel, *Cardio. Drug. Rev.*, (1993), 11(4), 501–515.

"Physicians' Desk Reference," (1992) 2207–2208.

Cimino et al., *Biochem. Pharmacology*, (1988), 37(14), 2739–2745.

Watanabe et al., *Federation Proceedings*, (1982), 41(7), 2292–2399.

Earl et al., *Life Sciences*, (1984), 35, 525–534.

Brindley, *Brit. J. Phychiat.*, (1983), 143, 332–337.

Keogh, *Aust. NZ. J. Med.*, (1989), 19, 108–112.

Funderbunk, *New Engl. J. Med.*, (1974), 290, 630–631.

Beretta, *Acta European Fertilitatis*, (1986), 17, 43–45.

"Physicians' Desk Reference," (1992), 1778–1779.

Hess in "Prazosin: Evaluation of a New Antihypertensive Agent," D. Cotton ed., American Elsevier, NY, (1974), 3–15.

Dadkar et al., *Ind. J. Exp. Biol.*, (1982), 20, 484–487.

D'Armiento et al., *Eur. J. Pharmacol.*, (1980), 65, 234–247.

Bhalla et al., *Brit. Med. J.*, (1972), 2, 1059.

Burke et al., *Med. J. Aust.*, (1980), 382–383.

Segasouthy et al., *Med. J. Malaysia*, (1982), 37(4), 384.

Ylitalo et al., *Acta Med. Scand.*, (1983), 213, 319–320.

Robbins et al., *J. Urol.*, (1983), 130, 975.

Adams et al., *J. Urol.*, (1984), 132, 1208.

Russell et al., *Med. J. Aust.*, (1985), 143, 321.

Taher et al., *Int. J. Impotence Res., Abstracts*, Milan, Italy (Sep. 14–17, 1992).

Trigo–Rocha et al., *Neurology and Urodynamics*, 13, (1998) 71–80.

* cited by examiner

N-CINNAMOYL DERIVATIVES OF BETA-CARBOLINE

CROSS-REFERENCE TO RELATED APPLICATION

This application is a divisional of U.S. patent application Ser. No. 09/155,811, filed Apr. 23, 1999 now U.S. Pat. No. 6,117,881, which is the U.S. national phase application International Application No. PCT/EP96/02277, filed on May 5, 1997.

This invention relates to a series of carboline derivatives, to processes for their preparation, pharmaceutical compositions containing them, and their use as therapeutic agents. In particular, the invention relates to carboline derivatives which are potent and selective inhibitors of cyclic guanosine 3',5'-monophosphate specific phosphodiesterase (cGMP specific PDE) having utility in a variety of therapeutic areas where such inhibition is thought to be beneficial, including the treatment of cardiovascular disorders.

Thus, according to a first aspect, the present invention provides compounds of formula (I)

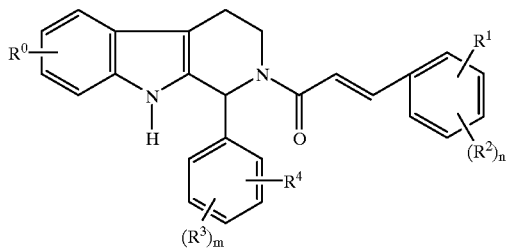

(I)

wherein $R^0$ represents -hydrogen or -halogen;

$R^1$ is selected from the group consisting of:
- -hydrogen,
- $-NO_2$,
- -trifluoromethyl,
- -trifluoromethoxy,
- -halogen,
- -cyano,
- a 5- or 6-membered heterocyclic group containing at least one heteroatom selected from oxygen, nitrogen and sulphur (optionally substituted by $-C(=O)OR^a$ or $C_{1-4}$alkyl),
- $-C_{1-6}$alkyl optionally substituted by $-OR^a$,
- $-C_{1-3}$alkoxy,
- $-C(=O)R^a$,
- $-O-C(=O)R^a$,
- $-C(=O)OR^a$,
- $-C_{1-4}$alkylene $C(=O)OR^a$,
- $-O-C_{1-4}$alkylene $-C(=O)OR^a$,
- $-C_{1-4}$alkylene-O-$C_{1-4}$alkylene-$C(=O)OR^a$,
- $-C(=O)NR^aSO_2R^c$,
- $-C(=O)C_{1-4}$alkylene Het, wherein Het represents 5- or 6-membered heterocyclic group as defined above,
- $-C_{1-4}$alkylene $NR^aR^b$,
- $-C_{2-6}$alkenylene$NR^aR^b$,
- $-C(=O)NR^aR^b$,
- $-C(=O)NR^aR^c$,
- $-C(=O)NR^aC_{1-4}$alkylene $OR^b$
- $-C(=O)NR^aC_{1-4}$alkylene Het, wherein Het represents a 5- or 6-membered heterocyclic group as defined above,
- $-OR^a$
- $-OC_{2-4}$alkylene $NR^aR^b$,
- $-OC_{1-4}$alkylene-$CH(OR^a)CH_2$ $NR^aR^b$,
- $-O-C_{1-4}$alkylene Het, wherein Het represents a 5- or 6-membered heterocyclic group as defined above,
- $-O-C_{2-4}$alkylene-$OR^a$
- $-O-C_{2-4}$alkylene-$NR^a-C(=O)-OR^b$,
- $-NR^aR^b$,
- $-NR^aC_{1-4}$alkylene$NR^aR^b$,
- $-NR^aC(=O)R^b$,
- $-NR^aC(=O)NR^aR^b$,
- $-N(SO_2C_{1-4}$alkyl$)_2$,
- $-NR^a(SO_2C_{1-4}$alkyl),
- $-SO_2NR^aR^b$, and
- $-OSO_2$trifluoromethyl;

$R^2$ is selected from the group consisting of:
- -hydrogen,
- -halogen,
- $-OR^a$,
- $-C_{1-6}$ alkyl,
- $-NO_2$, and
- $-NR^aR^b$, or $R^1$ and $R^2$, together form a 3- or 4-membered alkylene or alkenylene chain, optionally containing at least one heteroatom;

$R^3$ is selected from the group consisting of:
- -hydrogen,
- -halogen,
- $-NO_2$,
- -trifluoromethoxy,
- $-C_{1-6}$alkyl, and
- $-C(=O)OR^a$;

$R^4$ is hydrogen, or $R^3$ and $R^4$ together form a 3- or 4-membered alkylene or alkenylene chain, optionally containing at least one heteroatom;

$R^a$ and $R^b$, which may be the same or different, are independently selected from hydrogen and $C_{1-4}$alkyl;

$R^c$ represents phenyl or $C_{4-6}$cycloalkyl, which phenyl or $C_{4-6}$cycloalkyl can be optionally substituted by one or more halogen atoms, one or more $-C(=O)OR^a$ or one or more $-OR^a$;

n is an integer selected from 1, 2 and 3;

m is an integer selected from 1 and 2;

and pharmaceutically acceptable salts and solvates (e.g. hydrates) thereof.

The terms alkyl or alkylene as used herein respectively contain the appropriate indicated number of carbon atoms and appropriately include straight chained and branched alkyl or alkylene groups, typically methyl, methylene, ethyl and ethylene groups, and straight chained and branched propyl, propylene, butyl and butylene groups. The term $C_{2-6}$alkenylene as used herein contains 2 to 6 carbon atoms and appropriately includes straight chained and branched alkenylene groups, in particular ethenylene or the like.

The terms $C_{4-6}$ cycloalkyl denotes cyclic groups containing 4 to 6 carbon atoms, namely cyclobutane, cyclopentane and cyclohexane.

The term halogen as used herein includes fluorine, chlorine, bromine and iodine.

The term 5- or 6-membered heterocyclic group as used herein includes 5- or 6-membered heterocycloalkyl and heteroaryl groups, e.g. tetrahydrofuranyl, piperidyl, piperazinyl pyrrolidinyl, morpholinyl, pyridyl, imidazolyl, furyl, and tetrazolyl.

Appropriately, $R^o$ represents hydrogen. Alternatively $R^o$ may represent halogen, in particular fluorine.

$R^1$ may represent any of the substituents as hereinbefore described, or more particularly may represent any of —$OR^a$, —O—$C_{2-4}$alkyleneN$R^aR^b$, —O—$C_{1-4}$alkyleneHet and —O—$C_{2-4}$alkylene-$OR^a$. In particular, $R^1$ represents —O—$C_{2-4}$alkylene N$R^aR^b$, wherein suitably $C_{2-4}$alkylene may represent ethylene and aptly, $R^a$ and $R^b$ may independently represent methyl.

Particularly suitably $R^2$ represents hydrogen. Alternatively, in the case where $R^1$ and $R^2$ together form a 3- or 4-membered alkylene or alkenylene chain optionally containing at least one heteroatom as hereinbefore described, suitably $R^1$ and $R^2$ together form a methylenedioxy chain, an ethyleneoxy chain, an ethylenedioxy chain, an ethenyleneoxy chain, a propylene chain, a butylene chain or —$NR^a$ ethylene-O—. Aptly, $R^1$ and $R^2$ together form methylenedioxy, propylene or —$N(CH_3)$—$(CH_2)_2$—O—.

Suitably $R^3$ and $R^4$, together form a 3- or 4-membered alkylene or alkenylene chain, optionally containing at least one heteroatom as hereinbefore described. Particularly suitably $R^3$ and $R^4$ together form a methylenedioxy chain, an ethyleneoxy chain, an ethylenedioxy chain, an ethenyleneoxy chain, a propylene chain, a butylene chain or —$NR^a$ethylene-O—. Aptly $R^3$ and $R^4$ together form a methylenedioxy chain, an ethyleneoxy chain, an ethylenedioxy chain, an ethenyleneoxy chain or a propylene chain. In particular, $R^3$ and $R^4$ together form methylenedioxy or ethyleneoxy, most particularly ethyleneoxy.

A particular subgroup of compounds according to the present invention can be represented by formula (Ia)

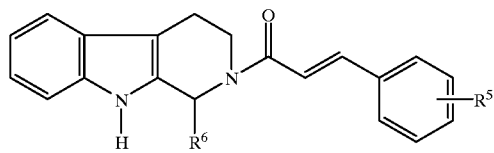

Ia wherein $R^5$ is selected from the group consisting of —OH, —$OC_{2-4}$alkylene N$R^aR^b$ and O—$C_{1-4}$alkylene Het, wherein Het is as hereinbefore described and $R^6$ represents

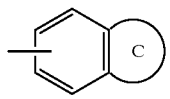

wherein C represents a 5- or 6-membered rn which may be saturated or partially or fully unsaturated and comprises carbon atoms and optionally one or two heteroatoms selected from oxygen, sulphur and nitrogen, optionally substituted by $C_{1-4}$alkyl;

and pharmaceutically acceptable salts and solvates (e.g. hydrates thereof).

Typically, $R^5$ represents —$OC_{2-4}$alkylene N$R^aR^b$, in particular —$OCH_2CH_2N(CH_3)_2$. Alternatively, $R^5$ may represent —O—$C_{1-4}$alkylene Het, where Het may suitable be piperidyl, pyrrolidinyl (optionally substituted by $C_{1-4}$alkyl, e.g. methyl) or morpholinyl.

Particularly aptly $R^6$ represents

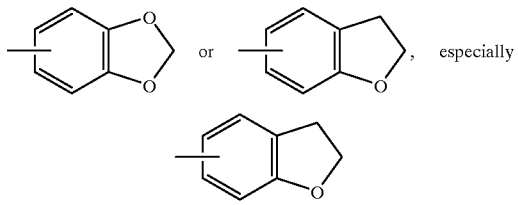, especially

The compounds of formula (I) may contain one or more asymmetric centres and thus can exist as enantiomers or diastereoisomers. It is to be understood that the invention includes both mixtures and separate individual isomers of the compounds of formula (I).

The pharmaceutically acceptable salts of the compounds of formula (I) which contain a basic centre are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of the formula (I) can also provide pharmaceutically acceptable metal salts, in particular alkali metal salts, with bases, Examples include the sodium and potassium salts.

Particular individual compounds of the invention include:
(E)-1-(1-Phenyl-1,3,4,9-tetrahydro-β-carbolin-2-yl)-3-phenylpropene-1-one
(E)-1-(1-Phenyl-1,3,4,9-tetrahydro-β-carbolin-2-yl)-3-(4-nitrophenyl)propene-1-one
(E)-1-(1-Phenyl-1,3,4,9-tetrahydro-β-carbolin-2-yl)-3-(4-trifluoromethylphenyl)propene-1-one
(E)-1-(1-Phenyl-1,3,4,9-tetrahydro-β-carbolin-2-yl)-3-(4-methoxyphenyl)propene-1 one
(E)-1-[1-(4-Methoxyphenyl)-1,3,4,9-tetrahydro-β-carbolin-2-yl]-3-(4-trifluoromethylphenyl)propene-1-one
(E)-N-[4-[3-Oxo-3-(1-phenyl-1,3,4,9-tetrahydro-β-carbolin-2-yl)propenyl]phenyl]acetamide
(E)-1-[1-(4-Methoxyphenyl)-1,3,4,9-tetrahydro-β-carbolin-2-yl]-3-phenylpropene-1-one
(E)-1-[1-(3,4-Methylenedioxyphenyl)-1,3,4,9-tetrahydro-β-carbolin-2-yl]-3-phenyl-propene-1-one
(E)-1-(1-Phenyl-1,3,4,9-tetrahydro-β-carbolin-2-yl)-3-(4-formylphenyl)propene-1-one
(E)-N-[4-[3-Oxo-3-(1-(4-nitrophenyl)-1,3,4,9-tetrahydro-β-carbolin-2-yl)propenyl]-phenyl]acetamide
(E)-1-[1-(4-Nitrophenyl)-1,3,4,9-tetrahydro-β-carbolin-2-yl]-3-phenylpropene-1-one
(E)-1-[1-(4-Trifluoromethoxyphenyl)-1,3,4,9-tetrahydro-β-carbolin-2-yl]-3-phenylpropene-1-one
(E)-1-[1-(4-Methylphenyl)-1,3,4,9-tetrahydro-β-carbolin-2-yl]-3-phenylpropene-1-one
(E)-N-[4-[3-Oxo-3-(1-(3,4-methylenedioxyphenyl)-1,3,4,9-tetrahydro-β-carbolin-2-yl)-propenyl]phenyl]acetamide
(E)-4-[3-Oxo-3-(1-phenyl-1,3,4,9-tetrahydro-β-carbolin-2-yl)-propenyl]benzoic acid, methyl ester
(E)-1-[1-(2-Chlorophenyl)-1,3,4,9-tetrahydro-β-carbolin-2-yl]-3-phenylpropene-1-one
(E)-1-(1-Phenyl-1,3,4,9-tetrahydro-β-carbolin-2-yl)-3-(3,4-Methylenedioxyphenyl)-propene-1-one
(E)-1-[1-(3,4-Methylenedioxyphenyl)-1,3,4,9-tetrahydro-β-carbolin-2-yl]-3-(4-bromophenyl)propene-1-one
(E)-1-[1-(4-Chlorophenyl)-1,3,4,9-tetrahydro-β-carbolin-2-yl]-3-phenylpropene-1-one
(E)-1-[1-(3,4-Methylenedioxyphenyl)-1,3,4,9-tetrahydro-β-carbolin-2-yl]-3-(4-ethoxyphenyl)propene-1-one (E)-4-[3-Oxo-3-(1-(3,4-methylenedioxyphenyl)-1,3,4,9-tetrahydro-β-carbolin-2-yl)propenyl]acetic acid, phenyl ester (E)-1-[1-(3,4-Methylenedioxyphenyl)-1,3,4,9-tetrahydro-β-carbolin-2-yl]-3-(4-hydroxyphenyl)propene-1-one (E)-1-[1-(3,4-Methylenedioxyphenyl)-1,3,4,9-tetrahydro-β-carbolin-2-yl]-3-(4-formylphenyl)propene-1-one (E)-1-[4-[3-Oxo-3-(1-(3,4-methylenedioxyphenyl)-1,3,4,9-tetrahydro-β-carbolin-2-yl)-propenyl]phenyl]-3-phenylurea (E)-1-[1-(3,4-Methylenedioxyphenyl)-1,3,4,9-tetrahydro-β-carbolin-2-yl]-3-(4-aminophenyl)propene-1-one (E)-1-[1-(3,4-Methylenedioxy-phenyl)-1,3,4,9-tetrahydro-β-carbolin-2-yl]-3-(4-nitro-phenyl)-propene-1-one (E)-1-[1-(3,4-Methylenedioxyphenyl)-1,3,4,9-tetrahydro-β-carbolin-2-yl]-3-[(4-bis(methylsulfonyl)aminophenyl] propene-1-one (E)-4-[3-Oxo-3-[1-(3,4-methylenedioxyphenyl)-1,3,4,9-tetrahydro-β-carbolin-2-yl]-propenyl]benzoic acid, methyl ester (E)-N-[4-[3-Oxo-3-[1-(3,4-methylenedioxyphenyl)-1,3,4,9-tetrahydro-β-carbolin-2-yl]propenyl]phenyl] methanesulfonamide (E)-4-[3-Oxo-3-[1-(3,4-methylenedioxyphenyl)-1,3,4,9-tetrahydro-β-carbolin-2-yl]propenyl]benzamide]

(E)-4-[3-Oxo-3-[1-(3,4-methylenedioxyphenyl)-1,3,4,9-tetrahydro-β-carbolin-2-yl]-propenyl]benzoic acid (E)-1-[1-(3,4-Methylenedioxyphenyl)-1,3,4,9-tetrahydro-β-carbolin-2-yl]-3-(4-cyanophenyl)propene-1-one (E)-1-[1-(3,4-Methylenedioxyphenyl)-1,3,4,9-tetrahydro-β-carbolin-2-yl]-3-(4-trifluoromethylphenyl)propene-1-one (E)-1-[1-(3,4-Methylenedioxyphenyl)-1,3,4,9-tetrahydro-β-carbolin-2-yl]-3-(3,4-methylenedioxyphenyl)propene-1-one (E)-1-[1-(3,4-Methylenedioxyphenyl)-1,3,4,9-tetrahydro-β-carbolin-2-yl]-3-(4-chlorophenyl)propene-1-one (E)-1-[1-(3,4-Methylenedioxyphenyl)-1,3,4,9-tetrahydro-β-carbolin-2-yl)-3-(4-trifluoromethoxyphenyl)propene-1-one (E)-1-[1-(3,4-Methylenedioxyphenyl)-1,3,4,9-tetrahydro-β-carbolin-2-yl]-3-(4-methylphenyl)propene-1-one (E)-[4-[3-Oxo-3-(1-(3,4-Methylenedioxyphenyl)-1,3,4,9-tetrahydro-β-carbolin-2-yl)propenyl]phenyl]urea (E)-1-[1-(3,4-Methylenedioxyphenyl)-1,3,4,9-tetrahydro-β-carbolin-2-yl]-3-(4-hydroxymethylphenyl)propene-1-one (E)-N-Benzyl4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(2,4-dichlorophenyl)propene-1-one (E)-1-[1-(3,4-Methylenedioxyphenyl)-1,3,4,9-tetrahydro-β-carbolin-2-yl]-3-(3-methoxy-4-hydroxyphenyl)propene-1-one (E)-1-[1-(3,4-Methylenedioxyphenyl)-1,3,4,9-tetrahydro-β-carbolin-2-yl]-3-(3-hydroxy-4-methoxyphenyl)propene-1-one (E)-1-[1-(3,4-Methylenedioxyphenyl)-1,3,4,9-tetrahydro-β-carbolin-2-yl]-3-(4-fluorophenyl)propene-1-one (E)-1-[1-(3,4-Methylenedioxyphenyl)-1,3,4,9-tetrahydro-β-carbolin-2-yl]-3-indan-5-yl-1-propene-1-one (E)-N-[4-[3-Oxo-3-(1-(3,4-methylenedioxyphenyl)-1,3,4,9-tetrahydro-β-carbolin-2-yl)propenyl]benzoyl] benzenesulfonamide (E)-1-[1-(3,4-Methylenedioxyphenyl)-1,3,4,9-tetrahydro-β-carbolin-2-yl]-3-(3,4-dichlorophenyl)propene-1-one (E)-1-[1-(3,4-Methylenedioxyphenyl)-1,3,4,9-tetrahydro-β-carbolin-2-yl]-3-(3,4-dimethoxyphenyl)propene-1-one (E)-1-[1-(3,4-Methylenedioxyphenyl)-1,3,4,9-tetrahydro-β-carbolin-2-yl]-3-(3,4-dihydroxyphenyl)propene-1-one (E)-N-Methyl-N-[4-(3-oxo-3-(1-(3,4-methylenedioxyphenyl)-1,3,4,9-tetrahydro-β-carbolin-2-yl)propenyl]phenyl]acetamide (E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide (E)-1-[1-(3,4-Methylenedioxyphenyl)-1,3,4,9-tetrahydro-β-carbolin-2-yl]-3-(3,5-dimethoxyphenyl)propene-1-one (E)-(N)-{4-[3-[1-(3,4-Methylenedioxyphenyl)-6-fluoro-1,3,4,9-tetrahydro-β-carbolin-2-yl]-3-oxopropenyl]phenyl}-acetamide (E)-1-[1-(3,4-Methylenedioxyphenyl)-1,3,4,9-tetrahydro-β-carbolin-2-yl]-3-(3,4 5-trimethoxyphenyl)propene-1-one (E)-N-[4-[3-Oxo-3-(1-(3,4-methylenedioxyphenyl)-1,3,4,9-tetrahydro-β-carbolin-2-yl)propenyl]phenyl] isobutyramide (E)-1-[1-(3,4-Methylenedioxyphenyl)-6-fluoro-1,3,4,9-tetrahydro-β-carbolin-2-yl]-3-phenylpropene-1-one (E)-N-(2-Methoxyethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9tetrahydro-β-carbolin-2-yl]-3-(3-hydroxyphenyl)propene-1-one (E)-1-[1-(3,4-Methylenedioxyphenyl)-1,3,4,9-tetrahydro-β-carbolin-2-yl]-3-(3-methoxyphenyl)propene-1-one (E)-1-[1-(3,4-Methylenedioxyphenyl)-1,3,4,9-tetrahydro-β-carbolin-2-yl]-3-(3-nitrophenyl)propene-1-one (E)-1-[1-(3,4-Methylenedioxyphenyl)-1,3,4,9-tetrahydro-β-carbolin-2-yl]-3-[4-(2-dimethylaminoethoxy)phenyl] propene-1-one (E)-N-(2-Morpholin-4-ylethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-[4-(1H-tetrazol-5-yl)phenyl]propene-1-one (E)-1-[1-(3,4-Methylenedioxyphenyl)-1,3,4,9-tetrahydro-β-carbolin-2-yl]-3-(3-aminophenyl)propene-1-one (E)-N-Cyclohexyl-4-[3-oxo-3-(1-(3,4-methylenedioxyphenyl)-1,3,4,9-tetrahydro-β-carbolin-2-yl)propenyl]benzamide (E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-cyanophenyl)propene-1-one (E)-N-(4-Piperidine-4-carboxylic acid, ethylester)4-[3-oxo-3-(1-(3,4-Methylenedioxyphenyl)-1,3,4,9-tetrahydro-β-carbolin-2-yl)propenyl]benzamide (E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide (E)-3-[3-Oxo-3-[1-(3,4-methylenedioxyphenyl)-1,3,4,9-tetrahydro-β-carbolin-2-yl]-propenyl]benzoic acid (E)-1-[1-(3,4-Methylenedioxyphenyl)-1,3,4,9-tetrahydro-β-carbolin-2-yl]-3-(3-(4-methylpiperazine-1-carbonyl)phenyl)propene-1-one (E)-N-(2-Piperazin-1-ylethyl)-3-[3oxo-3-(1-(3,4-methylenedioxyphenyl)-1,3,4,9-tetrahydro-β-carbolin-2-yl)propenyl]benzamide (E)-4-[3-Oxo-3-(1-(3,4-methylenedioxyphenyl)-1,3,4,9-tetrahydro-β-carbolin-2-yl)-propenyl]acetic acid ethyl ester (E)-1-[1-(3,4-Methylenedioxyphenyl)-1,3,4,9-tetrahydro-β-carbolin-2-yl]-3-(3-tetrazolophenyl)propene-1-one (E)-2-[3-Oxo-3-[1-(3,4-methylenedioxyphenyl)-1,3,4,9-tetrahydro-β-carbolin-2-yl]-propenyl]benzoicacid, methyl ester (E)-3-[3-Oxo-3-[1-(3,4-methylenedioxyphenyl)-1,3,4,9-tetrahydro-β-carbolin-2-yl]-propenyl]benzoic acid, methyl ester (E)-1-(4-[3-Oxo-3-(1-(3,4-methylenedioxyphenyl)-1,3,4,9-tetrahydro-β-carbolin-2-yl)-propenyl]phenyl)piperidine-4-carboxylic acid, ethyl ester (E)-N-(1-Ethylpyrroidin-2-yl-methyl)-3-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-(2-dimethylaminoethoxy)phenyl)propene-1-one (E)-1-[1-(3,4-Methylenedioxyphenyl)-1,3,4,9-tetrahydro-β-carbolin-2-y]-3-(3,5-diterbutyl-4-hydroxyphenyl)propene-1-one (E)-3-[3-Oxo-3-[1-(4-methoxycarbonylphenyl)-1,3,4,9-tetrahydro-β-carbolin-2-yl]propenyl]benzoic acid, methyl ester (E)-2-[3-Oxo-3-[1-(3,4-methylenedioxyphenyl)-1,3,4,9-tetrahydro-β-carbolin-2-yl]-propenyl]benzoic acid (E)-(4-[3-Oxo-3-(1-(3,4-methylenedioxyphenyl)-1,3,4,9-tetrahydro-β-carbolin-2-yl)propenyl]phenoxy)acetic acid, ethyl ester (E)-(4-[3-Oxo-3-(1-(3,4-methylenedioxyphenyl)-1,3,4,9-tetrahydro-β-carbolin-2-yl)-propenyl]phenyl)acetic acid (E)-(4-[3-Oxo-3-(1-(3,4-methylenedioxyphenyl)-1,3,4,9-tetrahydro-β-carbolin-2-yl)propenyl]phenoxy)acetic acid (E)-1-[1-(3,4-Methylenedioxyphenyl)-1,3,4,9-tetrahydro-β-carbolin-2-yl]-3-(3-nitro-4-chlorophenyl)propene-1-one (E)-1-[1-(3,4-Methylenedioxyphenyl)-1,3,4,9-tetrahydro-β-carbolin-2-yl]-3-(5-nitro-2-chlorophenyl)propene-1-one (E)-3-Chloro-4-[3-oxo-3-[1-(3,4-methylenedioxyphenyl)-1,3,4,9-tetrahydro-β-carbolin-2-yl]propenyl]benzoic acid, methyl ester (E)-(4-[3-Oxo-3-(1-(3,4-methylenedioxyphenyl)-1,3,4,9-tetrahydro-β-carbolin-2-yl)propenyl]benzyloxy)acetic acid (E)-1-[1-(3,4-Methylenedioxyphenyl)-1,3,4,9-tetrahydro-β-carbolin-2-yl]-3-(5-amino-2-chlorophenyl)propene-1-one (E)-3-Chloro-4-[3oxo-3-[1-(3,4-methylenedioxyphenyl)-1,3,4,9-tetrahydro-β-carbolin-2-yl]propenyl]benzoic acid (E)-1-[1-(3,4-Methylenedioxyphenyl)-1,3,4,9-tetrahydro-β-carbolin-2-yl]-3-(3,5-dibromo-4-hydroxyphenyl)propene-1-one (E)-1-[1-(3,4-Methylenedioxyphenyl)-1,3,4,9-tetrahydro-β-carbolin-2-yl]-3-(4-(2-dimethylaminopropoxy)phenyl)propene-1-one (E)-2-Chloro-5-[3oxo-3-[1-(3,4-methylenedioxyphenyl)-1,3,4,9-tetrahydro-β-carbolin-2-yl]propenyl]benzoic acid, methyl ester (E)-1-[1-(3,4-Methylenedioxyphenyl)-1,3,4,9-tetrahydro-β-carbolin-2-yl]-3-(4-(2-diisopropylaminoethoxy)phenyl)propene-1-one (E)-2-Chloro-5-[3-oxo-3-[1-(3,4-methylenedioxyphenyl)-1,3,4,9-tetrahydro-β-carbolin-2-yl]propenyl]benzoic acid (E)-1-[1-(3,4-Methylenedioxyphenyl)-1,3,4,9-tetrahydro-β-carbolin-2-yl]-3-(3-hydroxy-4-nitrophenyl)propene-1-one (E)-1-[1-(3,4-Methylenedioxyphenyl)-1,3,4,9-tetrahydro-β-carbolin-2-yl]-3-(3,5-dimethyl-4-hydroxyphenyl)propene-1-one (E)-1-[1-(3,4-Methylenedioxyphenyl)-1,3,4,9-tetrahydro-β-carbolin-2-yl]-3-(3-(2-dimethylaminoethoxy)4-nitrophenyl)propene-1-one (E)-1-[1-(3,4-Methylenedioxyphenyl)-1,3,4,9-tetrahydro-β-carbolin-2-yl]-3-(3-(2-dimethylaminoethoxy)-4-aminophenyl)propene-1-one (E)-1-[1-(3,4-Methylenedioxyphenyl)-1,3,4,9-tetrahydro-β-carbolin-2-yl]-3-(3-nitro-4-hydroxy-5-methoxyphenyl)propene-1-one (E)-1-[1-(3,4-Methylenedioxyphenyl)-1,3,4,9-tetrahydro-β-carbolin-2-yl]-3-(3-chlorophenyl)propene-1-one (E)-1-[1-(4-Methoxy-phenyl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2,6-dichlorophenyl)propene-1-one (E)-1-[1-(3,4-Methylenedioxyphenyl)-1,3,4,9-tetrahydro-β-carbolin-2-yl]-3-(4-methylaminomethylphenyl)propene-1-one (E)-1-[1-(3,4-Methylenedioxyphenyl)-1,3,4,9-tetrahydro-β-carbolin-2-yl]-3-(3-methylphenyl)-propene-1-one (E)-N-Methyl-(4-[3oxo-3-(1-(3,4-methylenedioxyphenyl)-1,3,4,9-tetrahydro-β-carbolin-2-yl)propenyl]benzenesulfonamide (E)-1-[1-(3,4-Methylenedioxyphenyl)-1,3,4,9-tetrahydro-β-carbolin-2-yl]-3-(3-hydroxy-4-acetylphenyl)propene-1-one (E)-1-[1-(2,3-Dihydrobenzofuran-5-yl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2-hydroxyphenyl)propene-1-one (E)-1-[1-(3,4-Methylenedioxyphenyl)-1,3,4,9-tetrahydro-β-carbolin-2-yl]-3-(3-nitro-2-piperidin-1-ylphenyl)propene-1-one (E)-1-[1-(2,3-Dihydrobenzofuran-5-yl)-1,3,4,9-tetrahydro-β-carbolin-2-yl]-3-phenylpropene-1-one (E)-1-[1-(4-isopropylphenyl)-1,3,4,9-tetrahydro-β-carbolin-2-yl]-3-(3-nitrophenyl)propene-1-one (E)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(3,4-Methylenedioxyphenyl)-1,3,4,9-tetrahydro-βcarbolin-2yl]-3-phenylpropene-1-one (E)-(S)-1-[1-(3,4-Methylenedioxyphenyl)-1,3,4,9-tetrahydro-β-carbolin-2-yl]-3-phenylpropene-1-one (E)-1-[1-(4-Methoxyphenyl)-1,3,4,9-tetrahydro-β-carbolin-2-yl]-3(3-nitrophenyl)propene-1-one (E)-1-[1-(4-Methylphenyl)-1,3,4,9-tetrahydro-β-carbolin-2-yl]-3-(2-chloro-5-nitrophenyl)propene-1-one (E)-N-(Tetrahydrofuran-2-ylmethyl)-3-[3-oxo-3-(1-(3,4-methylenedioxy)-1,3,4,9-tetrahydro-β-carbolin-2-yl)propenyl]benzamide (E)-1-[1-(Indan-5-yl)-1,3,4,9-tetrahydro-β-carbolin-2-yl]-3-phenylpropene-1-one (E)-1-[1-(3,4-Methylenedioxyphenyl)-1,3,4,9-tetrahydro-β-carbolin-2-yl]-3-(3-acetylphenyl)propene-1-one (E)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-4-[3-Oxo-3-[1-(4-methoxyphenyl)-1,3,4,9-tetrahydro-β-carbolin-2-yl]propenyl]-benzoic acid, methyl ester (E)-1-[1-(3,4-Methylenedioxyphenyl)-1,3,4,9-tetrahydro-β-carbolin-2-yl]-3-(4-methyl-3,4-dihydro-2H-benzo[1,4]oxazin-6-yl)propene-1-one (E)-1-[1-(3,4-Methylenedioxyphenyl)-1,3,4,9-tetrahydro-β-carbolin-2-yl]-3-(2-hydroxy-5-nitrophenyl)propene-1-one (E)-4-[3-Oxo-3-[1-(2,3-dihydrobenzofuran-5-yl)-1,3,4,9-tetrahydro-β-carbolin-2-yl]propenyl]benzoic acid, methyl ester (E)-4-[3-Oxo-3-[1-(4-methoxyphenyl)-1,3,4,9-tetrahydro-β-carbolin-2-yl]propenyl]benzoic acid (E)-4-[3-Oxo-3-[1-(2,3-dihydrobenzofuran-5-yl)-1,3,4,9-tetrahydro-β-carbolin-2-yl]propenyl]benzoic acid (E)-1-[1-(Benzofuran-5-yl)-1,3,4,9-tetrahydro-β-carbolin-2-yl]-3-phenylpropene-1-one (E)-3-[3-Oxo-3-(1-(3,4-methylenedioxyphenyl)-1,3,4,9-tetrahydro-β-carbolin-2-yl)-propenyl]phenyl) trifluoromethanesulfonic acid, phenyl ester (E)-1-[1-(3,4-Methylenedioxyphenyl)-1,3,4,9-tetrahydro-β-carbolin-2-yl]-3-[4-(2-hydroxyethoxy)phenyl]propene-1-one (E)-1-[1-(Benzofuran-5-yl-1,3,4,9-tetrahydro-β-carbolin-2-yl]-3-(4-(2-dimethylaminoethoxy)phenyl)propene-1-one (E)-1-[1 (3,4-Methylenedioxyphenyl)-1,3,4,9-tetrahydro-β-carbolin-2-yl]-3-(2-dimethylaminophenyl)propene-1-one (E)-1-[1-(3,4-Methylenedioxyphenyl)-1,3,4,9-tetrahydro-β-carbolin-2-yl]-3-(2-piperidin-1-ylphenyl)propene-1-one (E)-4-[3-Oxo-3-[1-(benzofuran-5-yl-1,3,4,9-tetrahydro-β-carbolin-2-yl]-propenyl]benzoic acid, methyl ester (E)-4-[3-(1-Benzofuran-5-yl-1,3,4,9-tetrahydro-β-carbolin-2-yl)-3-oxo-propenyl]benzoic acid (E)-4-[3-Oxo-3-(1-(3,4-methylenedioxyphenyl)-1,3,4,9-tetrahydro-β-carbolin-2-yl)propenyl]phenyl) trifluoromethanesulfonic acid, phenyl ester (E)-1-[1-(3,4-Methylenedioxyphenyl)-1,3,4,9-tetrahydro-β-carbolin-2-yl]-3-(2-(2-dimethylaminoethoxy)phenyl)propene-1-one (E)-1-[1-(3-Fluoro-4-methoxyphenyl)-1,3,4,9-tetrahydro-β-carbolin-2-yl]-3-phenylpropene-1-one (E)-(R)-1-[1-(2,3-Dihydrobenzofuran-5-yl)-1,3,4,9-tetrahydro-β-carbolin-2-yl]-3-(4-(2dimethylaminoethoxy)phenyl)propene-1-one (E)-1-(2,3-Dihydrobenzo[1,4]dioxin6-yl)-1,3,4,9-tetrahydro-β-carbolin-2-yl1-3-phenylpropene-1-one (E)-1-[1-(2,3-Dihydrobenzofuran-5-yl)-1,3,4,9-tetrahydro-β-carbolin-2-yl)]-3-(4-(2-pyrrolidin-1-ylethoxy)phenyl)propene-1-one (E)-1-[1-(3,4-Methylenedioxyphenyl)-1,3,4,9-tetrahydro-β-carbolin-2-yl]-3-[4-pyrrolidin-1-ylphenyl]propene-1-one (E)-(R)-1-[1-(2,3-Dihydrobenzofuran-5-yl)-1,3,4,9-tetrahydro-β-carbolin-2-yl]-3-(3-nitrophenyl)propene-1-one (E)-1-[1-(3,4-Methylenedioxyphenyl)-1,3,4,9-tetrahydro-β-carbolin-2-yl]-3-[4-imidazol-1-ylphenyl]propene-1-one (E)-4-[3-[1-(2,3-Dihydrobenzo[1,4]dioxin-6-yl)-1,3,4,9-tetrahydro-β-carbolin-2-yl]-3-oxopropenyl]benzoic acid, methyl ester (E)-1-[1-(2,3-Dihydrobenzo[1,4]dioxin-6-yl)-1,3,4,9-tetrahydro-β-carbolin-2-yl]-3-(3-nitrophenyl)propene-1-one (E)-1-[1-(2,3-Dihydrobenzo[1,4]dioxin-6-yl)-1,3,4,9-tetrahydro-β-carbolin-2-yl)]-3-(4-(2-dimethylaminoethoxy)phenyl)propene-1-one (E)-1-[1-(3-Fluoro-4-methoxyphenyl)-1,3,4,9-tetrahydro-β-carbolin-2-yl)]-3-(4-(2-dimethylaminoethoxy)phenyl)propene-1-one (E)-4-[3-[1-(2,3-Dihydrobenzo[1,4]dioxin-6-yl)-1,3,4,9-tetrahydro-β-carbolin-2-yl]-3-oxopropenyl]benzoic acid (E)-(R)-1-[1-(2,3-Dihydrobenzofuran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-1-[1-(2,3-Dihydrobenzofuran-5-yl)-1,3,4,9-tetrahydro-β-carbolin-2-yl]-3-(4-aminophenyl)propene-1-one (E)-(S)-1-[1-(2,3-Dihydrobenzofuran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(2,3-Dihydrobenzofuran-5-yl)-1,3,4,9-tetrahydro-β-carbolin-2-yl)]-3-(4-(1-(S)-methylpyrrolidin-2-yl-methoxy)phenyl)propene-1-one (E)-(R)-1-[1-(2,3-Dihydrobenzofuran-5-yl)-1,3,4,9-tetrahydro-β-carbolin-2-yl]-3-(3-hydroxyphenyl)propene-1-one (E)-(R)-1-[1-(2,3-Dihydrobenzofuran-5-yl)-1,3,4,9-tetrahydro-β-carbolin-2-yl)]-3-(4-(2-dimethylamino-1-methylethoxy)phenyl)propene-1-one (E)-1-(1-Phenyl-1,3,4,9-tetrahydro-β-carbolin-2-yl)-3-(4-(4-methylpyperazin-1-yl)-phenyl)propene-1-one (E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)phenyl)propene-1-one (E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one (E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one (E)-4-[3-Oxo-3-[1-(3,4-fluorophenyl)-1,3,4,9-tetrahydro-β-carbolin-2-yl]propenyl]benzoic acid, methyl ester (E)-(R)-[1-(2,3-Dihydrobenzofuran-5-yl)-1,3,4,9-tetrahydro-β-carbolin-2-yl)]-3-(4-(2-diethylaminoethoxy)phenyl)propene-1-one (E)-(R)1-[1-(2,3-Dihydrobenzofuran-5-yl)-1,3,4,9-tetrahydro-β-carbolin-2-yl)]-3-(4-(2-dimethylaminopropoxy)phenyl)propene-1-one (E)-4-[3-Oxo-3-[1-(3,4-difluorophenyl)-1,3,4,9-tetrahydro-β-carbolin-2-yl]propenyl]-benzoic acid (E)-(R)-1-[1-(2,3-Dihydrobenzofuran-5-yl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl)]-3-(4-(2-pyrrolidin-1-ylethoxy)phenyl)propene-1-one (E)-(R)-1-[1-(3,4-Methylenedioxyphenyl)-1,3,4,9-tetrahydro-β-carbolin-2-yl)]-3-(4-(2-diethylaminoethoxy)phenylpropene-1-one (E)-1-[1-(3-Fluoro-4-methoxyphenyl)-1,3,4,9-tetrahydro-β-carbolin-2-yl)]-3-(3-nitrophenyl)propene-1-one (E)-(R)-1-[1-(2,3-Dihydrobenzofuran-5-yl)-1,3,4,9-tetrahydro-β-carbolin-2-yl]-3-(4-trifluoromethylphenyl)propene-1-one (E)-(R)-1-[1-(2,3-Dihydrobenzofuran-5-yl)-1,3,4,9-tetrahydro-β-carbolin-2-yl]-3-(3-trifluoromethylphenyl)propene-1-one (E)-(R)-1-[1-(2,3-Dihydrobenzofuran-5-yl)-1,3,4,9-tetrahydro-β-carbolin-2-yl]-3-(4-(2-morpholin-4-ylethoxy)phenyl)propene-1-one (E)-(R)-1-[1-(2,3-Dihydrobenzofuran-5-yl)-1,3,4,9-tetrahydro-β-carbolin-2-yl]-3-(4-(2-(ethylmethylamino) ethoxy)phenyl)propene-1-one (E)-1-[1-(2,3-Dihydrobenzofuran-5-yl)-1,3,4,9-tetrahydro-β-carbolin-2-yl]-3-(4-(3-(dimethylamino)propenyl) phenyl)propene-1-one (E)-(R)-1-[1-(2,3-Dihydrobenzofuran-5-yl)-1,3,4,9-tetrahydro-β-carbolin-2-yl]-3-(4-(3-dimethylamino-2-hydroxypropoxy)phenyl)propene-1-one (E)-(R)-1-[1-(2,3-Dihydrobenzofuran-5-yl)-1,3,4,9-tetrahydro-β-carbolin-2-yl)-3-(4-formylphenyl)propene-1-one (E)-(R)-1-[1-(2,3-Dihydrobenzofuran-5-yl)-1,3,4,9-tetrahydro-β-carbolin-2-yl]-3-(4-propylaminomethyl) phenyl)propene-1-one (E)-(R)-1-[1-(2,3-Dihydrobenzofuran-5-yl)-1,3,4,9-tetrahydro-β-carbolin-2-yl]-3-[4-(2-dimethylaminoethylamino)phenylpropene-1-one (E)-(R)-1-[1-(2,3-Dihydrobenzofuran-5-yl)-1,3,4,9-tetrahydro-β-carbolin-2-yl]-3-(4-(2-aminoethoxy)phenyl)propene-1-one (E)-(R)-1-[1-(2,3-Dihydrobenzofuran-5-yl)-1,3,4,9-tetrahydro-β-carbolin-2-yl]-3-(4-hydroxyphenyl)propene-1-one (E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one (E)-(R)-1-[1-(2,3-Dihydrobenzofuran-5-yl)-1,3,4,9-tetrahydro-β-carbolin-2-yl]-3-(4-methylaminomethyl)phenyl)propene-1-one (E)-(R)-1-[1-(2,3-Dihydrobenzofuran-5-yl)-1,3,4,9-tetrahydro-β-carbolin-2-yl]-3-(4-isopropylaminomethyl)phenyl)propene-1-one (E)-(R)-1-[1-(2,3-Dihydrobenzofuran-5-yl)-1,3,4,9-tetrahydro-β-carbolin-2-yl]-3-(4-dimethylaminomethyl)phenyl)propene-1-one (E)-(R)-1-[1-(2,3-Dihydrobenzofuran-5-yl)-1,3,4,9-tetrahydro-β-carbolin-2-yl]-3-[4-(3-dimethylaminopropoxy)phenyl]propene-1-one (E)-(R)-1-[1-(2,3-Dihydrobenzofuran-5-yl)-1,3,4,9-tetrahydro-β-carbolin-2-yl]-3-(4-(2-piperidin-1-ylethoxy)phenyl)propene-1-one (E)-1-[1-(3,4-Methylenedioxyphenyl)-1,3,4,9-tetrahydro-β-carbolin-2-yl)-3-(4-(2-piperidin-1-ylethoxy)phenyl]propene-1-one (E)-(R)-[2-(4-{3-[1-(2,3-Dihydrobenzofuran-5-yl)-1,3,4,9-tetrahydro-β-carbolin-2-yl]-3-oxopropenyl}phenoxy)ethyl]methylcarbamic acid, tertbutyl ester (E)-(R)-1-[1-(2,3-Dihydrobenzofuran-5-yl)-1,3,4,9-tetrahydro-β-carbolin-2-yl]-3-[4-(2-methylaminoethoxy)phenyl]propene-1-one and pharmaceutically acceptable salts and solvates (e.g. hydrates) thereof. A specific compound of the invention is:

(E)-(R)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one and pharmaceutically acceptable salts and solvates (e.g. hydrates) thereof.

It has been shown that compounds of the present invention are potent and selective inhibitors of cGMP specific PDE. Thus, compounds of formula (I) are of interest for use in therapy, specifically for the treatment of a variety of conditions where inhibition of cGMP specific PDE is thought to be beneficial.

As a consequence of the selective PDE 5 inhibition exhibited by compounds of the present invention, cGMP levels are elevated, which in turn can give rise to beneficial anti-platelet, anti-neutrophil, anti-vasospastic, vasodilatory, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-HT$_1$. The compounds of formula (I) therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma, erectile dysfunction and diseases characterised by disorders of gut motility (e.g. irritable bowel syndrome).

It will be appreciated that references herein to treatment extend to prophylaxis as well as treatment of established conditions.

It will also be appreciated that a compound of formula (I), or a physiologically acceptable salt or solvate thereof can be administered as the raw compound, or as a pharmaceutical composition containing either entity.

There is thus provided as a further aspect of the invention a compound of formula (I) for use in the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases. stroke. bronchitis, chronic asthma, allergic asthma, allergic rhinitis, glaucoma, erectile dysfunction or diseases characterised by disorders of gut motility (e.g. IBS).

According to another aspect of the invention, there is provided the use of a compound of formula (I) for the manufacture of a medicament for the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS).

In a further aspect, the invention provides a method of treating stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS) in a human or non-human animal body which comprises administering to said body a therapeutically effective amount of a compound with formula (I).

Compounds of the invention may be administered by any suitable route, for example by oral, buccal, sub-lingual, rectal, vaginal, nasal, topical or parenteral (including intravenous, intramuscular, subcutaneous and intracoronary) administration. Oral administration is generally preferred.

For administration to man in the curative or prophylactic treatment of the disorders identified above, oral dosages of a compound of formula (I) will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of the formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agents (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example salts, or monosaccharides such as mannitol or glucose, to make the solution isotonic with blood.

Thus, the invention provides in a further aspect a pharmaceutical composition comprising a compound of the formula (I) together with a pharmaceutically acceptable diluent or carrier therefor.

There is further provided by the present invention a process of preparing a pharmaceutical composition comprising a compound of formula (I), which process comprises mixing a compound of formula (I) together with a pharmaceutically acceptable diluent or carrier therefor.

A compound of formula (I) may also be used in combination with other therapeutic agents which may be useful in the treatment of the above-mentioned disease states. The invention thus provides, in another aspect, a combination of a compound of formula (I) together with another therapeutically active agent.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a compound of formula (I) will be readily appreciated by those skilled in the art.

Compounds of formula (I) may be prepared by any suitable method known in the art or by the following processes which form part of the present invention. In the methods below $R^o$, $R^1$, $R^2$, $R^3$, and $R^4$ are are as defined in formula (I) above unless otherwise indicated.

There is a further provided by the present invention a process (A) of preparing a compound of formula (I), which process comprises reacting compounds of formula (II) and (III)

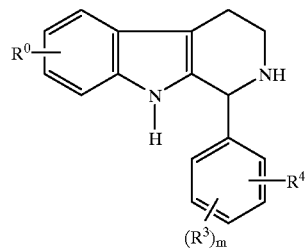

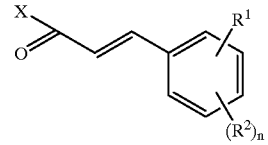

where X represents a hydroxyl or halogen group.

Suitably the reaction is carried out in the presence of 1,3-dicyclohexylcarbodiimide (DCC) or 1-(3-dimethylaminopropyl)-3-ethylcarbodiumide (EDCI) and 1-hydroxybenzotriazole (HOBT) in a suitable organic solvent, such as dimethylformamide (DMF) or dichloromethane (DCM) for several hours, e.g. 8 hours to 2 days.

Compounds of formula (I) may be prepared as individual enantiomers from the appropriate enantiomer of formula (II) or as a racemic mixture from the appropriate racemic compound of formula (II). Individual enantiomers of the compounds of the invention may be prepared from racemates by resolution using methods known in the art for the separation of racemic mixtures into their constituent enantiomers, for example using HPLC on a chiral column such as Hypersil naphtyl urea or using separation of salts of diastereoisomers.

A compound of formula (II) may be prepared by Pictet-Spengler cyclization between a tryptamine derivative of formula (IV) and an aldehyde of formula (V)

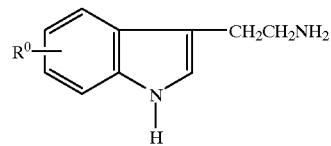

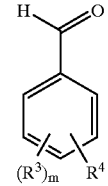

The reaction may conveniently be effected in a suitable solvent such as a halogenated hydrocarbon (e.g. dichloromethane) or an aromatic hydrocarbon (e.g. toluene) in the presence of an acid such as trifluoroacetic acid (TFA). The reaction may conveniently be carried out at a temperature of from 20° C. to reflux to provide a compound of formula (II) in one step. The reaction may also be carried out in a solvent such as an aromatic hydrocarbon (e.g. toluene) under reflux optionally using a Dean-stark apparatus to trap the water produced.

The reaction provides racemic compounds of formula (II). Enantiomers may be obtained from a resolution with N-acetyl leucine using fractional crystallization in EtOAc::MeOH as solvent. (R) and (S) enantiomers may be isolated as salts depending upon whether N-acetyl-(D) and (L)-leucine was used as the starting material.

Compounds of formulae (IV) and (V) are commercially available compounds or prepared by standard synthetic techniques as hereinafter described in the Examples.

A compound of formula (III) can be prepared from a corresponding aldehyde of formula (VI)

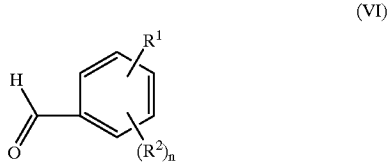

(VI)

suitably by employing a Wittig reaction followed by basic hydrolysis.

Alternatively a compound of formula (III) may be prepared from a compound of formula (VI) by a Knoevenhagel reaction employing malonic acid.

Compounds of formula (VI) can be prepared from known corresponding alcohol, nitrile, or halide derivatives, using techniques well known in the art of synthetic organic chemistry.

According to a further general process (B) compounds of formula (I) can be converted to alternative compounds of formula (I), employing suitable interconversion techniques such as hereinafter described in the Examples.

Compounds of this invention may be isolated in association with solvent molecules by crystallization from or evaporation of an appropriate solvent.

The pharmaceutically acceptable acid addition salts of the compounds of formula (I) which contain a basic centre may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of a compound of formula (I) with a suitable base. Both types of salt may be formed or inter-converted using ion-exchange resin techniques.

Thus, according to a further aspect of the invention, we provide a process for preparing a compound of formula (I) or a salt or solvate (e.g. hydrate) thereof which comprises process (A) or (B) as hereinbefore described followed by i) salt formation, or
ii) solvate (e.g. hydrate) formation.

The following additional abbreviations are hereinafter used in the accompanying examples: rt (room temperature), DMSO (dimethylsulphoxide), NBS (N-bromosuccinimide), THF (tetrahydrofuran), TFA (trifluoroacetic acid), PTSA (p-toluene sulphonic acid), AIBN (2,2'-azobis isobutyronitrile), and TBDMSCl (tert-butyldimethylsilyl chloride).

Intermediate 1
1-Phenyl-2,3,4,9-tetrahydro-1H-β-carboline

A solution of tryptamine (15 g, 94.0 mmol) and benzaldehyde (10.9 g, 1.1 equiv.) in DCM (800 mL) was treated with TFA (15 mL, 2 equiv.). The resulting mixture was stirred at rt for one day and then neutralized to pH 7 with a saturated aqueous solution of sodium carbonate. After filtration and concentration to dryness the residue was recrystallized from 2-propanol to give the title compound (11.0 g, 47%) as white crystals.
MP: 175–177° C.

Intermediate 2
1-(4-Methoxyphenyl)-2,3,4,9-tetrahydro-1H-β-carboline

This product was prepared using the same procedure as for Intermediate 1 with tryptamine (15 g, 94.9 mmol), 4-methoxybenzaldehyde (12.9 g, 1.1 equiv.) and TFA (14.6 mL, 2 equiv.) to give the title compound (20.9 g, 80%) as a brownish powder.
MP: 131° C.

Intermediate 3
1-(4-Nitrophenyl)-2,3,4,9-tetrahydro-1H-β-carboline

This product was prepared using the same procedure as for Intermediate 1 with tryptamine (2.0 g, 12.5 mmol), 4-nitrobenzaldehyde (1.88 g, 1 equiv.) and TFA (1.9 mL, 2 equiv.) to give the title compound (3.1 g, 86%) as a yellow powder.
MP: 190° C.

Intermediate 4
1-(4-Trifluoromethoxyphenyl)-2,3,4,9-tetrahydro-1H-β-carboline

This product was prepared using the same procedure as for Intermediate 1 with tryptamine (2.0 g, 12.5 mmol), 4-trifluoromethoxybenzaldehyde (2.4 g, 1 equiv.) and TFA (1.9 mL, 2 equiv.) to give the title compound (1.6 g, 38%) as a white powder.
MP: 68–69° C.

Intermediate 5
1-(4-Chlorophenyl)-2,3,4,9-tetrahydro-1H-β-carboline

This product was prepared using the same procedure as for Intermediate 1 with tryptamine (5.0 g, 30 mmol), 4-chlorobenzaldehyde (4.6 g, 1 equiv.) and TFA (4.6 mL, 2 equiv.) to give the title compound (4.16 g, 49%) as a white powder.
MP: 161° C.

Intermediate 6
1-(4-Methylphenyl)-2,3,4,9-tetrahydro-1H-β-carboline

This product was prepared using the same procedure as for Intermediate 1 with tryptamine (1.0 g, 6.2 mmol), 4-methylbenzaldehyde (0.74 g, 1 equiv.) and TFA (1 mL, 2 equiv.) to give the title compound (1.6 g, 100%) as a white powder.
MP: 207–209° C.

Intermediate 7
1-(3,4-Methylenedioxyphenyl)-2,3,4,9-tetrahydro-1H-β-carboline

This product was prepared using the same procedure as for Intermediate 1 with tryptamine (20.0 g, 120 mmol), 3,4-methylenedioxybenzaldehyde (20.6 g, 1.1 equiv.) and TFA (18 mL, 2 equiv.) to give the title compound (22 g, 60%) as white crystals after recrystallization from ethanol.
MP: 178° C.

Intermediate 8
4-(2,3,4,9-Tetrahydro-1H-β-carbolin-1-yl)benzoic Acid, Methyl Ester This product was prepared using the same procedure as for Intermediate 1 with tryptamine (2.8 g, 17.4 mmol), 4-formylbenzoic acid, methyl ester (2.87 g, 1.1 equiv.) and TFA (2.7 mL, 2 equiv.) to give the title compound (0.5 g, 9%) as white crystals after recrystallization from isopropanol:$H_2O$.
MP: 179° C.

Intermediate 9
1-Indan-5-yl-2,3,4,9-tetrahydro-1H-β-carboline

This product was prepared using the same procedure as for Intermediate 1 with tryptamine (1.28 g, 8.0 mmol), indan-5-carboxaldehyde (1.3 g, 1.1 equiv.) and TFA (1.2 mL, 2 equiv.) to give the title compound (0.36 g, 14%).

$^1$H NMR (CDCl$_3$) δ7.6 (s, 1H), 7.4 (m, 1H), 6.9–7.2 (m, 6H), 5.1 (s, 1H), 3.3–3.4 (m, 1H), 2.9–3.1 (m, 1H), 2.7–2.9 (m, 6H), 1.9–2.2 (q, 2H).

Intermediate 10

1-(2,3-Dihydrobenzofuran-5-yl)-2,3,4,9-tetrahydro-1H-β-carboline

This product was prepared using a two-step procedure. A solution of tryptamine (32.4 g, 0.2 mol) and 2,3-dihydrobenzofuran-5-carboxaldehyde (30.0 g, 1 equiv.) in toluene (1 L) was heated under reflux for 4 hours. After removal of 4 mL of water and evaporation of toluene the residue was dissolved in DCM (1 L) in the presence of TFA (31 mL, 2 equiv.). The resulting mixture was stirred at rt for 16 hours. Then 1 L of a saturated aqueous solution of NaHCO$_3$ was added. After extraction with DCM and drying over MgSO$_4$, the organic solution was evaporated in vacuo. Recrystallization from DCM:iPr$_2$O (2:30) gave the title compound as white crystals in a 80% yield.

$^1$H NMR (CDCl$_3$) δ7.6 (s, 1H), 7.5–7.6 (m, 1H), 7–7.3 (m, 5H), 6.7–6.75 (d, 1H), 5.1 (s, 1H), 4.5–4.6 (t, 2H), 3.3–3.45 (m, 1H), 3.05–3.2 (t, 3H), 2.7–3 (m, 2H).

Intermediate 11

1-(4-Isopropylphenyl)-2,3,4,9-tetrahydro-1H-β-carboline

This product was prepared using the same procedure as for Intermediate 1 with tryptamine (5.0 g, 31.2 mmol), 4-isopropylbenzaldehyde (5.08 g, 1.1 equiv.) and TFA (4.8 mL, 2 equiv.) to give the title compound (5.9 g, 67%) as white crystals after recrystallization from iPr$_2$O.

MP: 146° C.

Intermediate 12

1-(2,3-Benzofuran-5-yl)-2,3,4,9-tetrahydro-1H-β-carboline

This product was prepared using the same procedure as for Intermediate 1 with tryptamine (2.27 g, 14.1 mmol), 2,3-benzofuran-5-carboxaldehyde (2.1 g, 1 equiv., prepared according to the procedure of Dom, C.P et al EP 481671A1) and TFA (2.2 mL, 2 equiv.) to give the title compound (3.0 g, 74%) as white crystals after recrystallization from cyclohexane.

MP: 134–136° C.

Intermediate 13

1-(2,3-Dihydrobenzo[1.4]dioxin6-yl)-2,3,4,9-tetrahydro-1H-β-carboline

This product was prepared using the same procedure as for Intermediate 1 with tryptamine (4,92 g, 30.7 mmol), 2,3-dihydrobenzo[1,4]dioxin-6-carboxaldehyde (5.05 g, 1.0 equiv.) and TFA (5.0 mL, 2 equiv.) to give the title compound (7.05 g, 75%) as white crystals after recrystallization from iPr$_2$O.

MP: 144° C.

Intermediate 14

1-(3-Fluoro-4-methoxyphenyl)-2,3,4,9-tetrahydro-1H-β-carboline

This product was prepared using the same procedure as for Intermediate 1 with tryptamine (4.80 g, 30.0 mmol), 3-fluoro4-methoxybenzaldehyde (4.86 g, 1.05 equiv.) and TFA (4.6 mL, 2 equiv.) to give the title compound (5.2 g, 59%) as white crystals.

MP: 68° C.

Intermediate 15

1-(3,4-Difluorophenyl)-2,3,4,9-tetrahydro-1H-β-carboline

This product was prepared using the same procedure as for Intermediate 1 with tryptamine (5.4 g, 33.5 mmol), 3,4-difluorobenzaldehyde (5.0 g, 1.05 equiv.) and TFA (5.2 mL, 2 equiv.) to give the title compound (7.8 g, 82%) as white crystals.

MP: 151° C.

Intermediate 16

1-(3,4-Methylenedioxyphenyl)-4-fluoro-2,3,4,9-tetrahydro-1H-β-carboline

This product was prepared using the same procedure as for Intermediate 1 with 5-fluorotryptamine (1.59 g, 8.9 mmol), 3,4-methylenedioxybenzaldehyde (1.47 g, 1.1 equiv.) and TFA (1.4 mL, 2 equiv.) to give the title compound (2,34 g, 85%) as white crystals.

MP: 172° C.

Analysis for $C_{18}H_{15}FN_2O_2$:

Calculated: C,69.67; H,4.87; N,6.12.

Found: C,69.47; H,4.85; N,6.23%

Intermediate 17

1-(2-Chlorophenyl)-2,3,4,9-tetrahydro-1H-β-carboline

This product was prepared using the same procedure as for Intermediate 1 with tryptamine (1.0 g, 6.2 mmol), 2-chlorobenzaldehyde (0.7 mL, 1.0 equiv.) and TFA (1.0 mL, 2 equiv.) to give the title compound (1.2 g, 69%).

$^1$H NMR (CDCl$_3$) δ7.6 (s, 1H), 7.45 (d, 1H), 7.40 (d, 1H), 6.9–7.2 (m, 6H), 5.6 (s, 1H), 3.2–3.0 (m, 2H), 2.9–2.7 (m, 2H), 2.4 (s, 1H).

Intermediate 18

(S)-1-(3,4-Methylenedioxyphenyl)-2,3,4,9-tetrahydro-1H-β-carboline (S)-1-(3,4-Methylenedioxyphenyl)-2,3,4,9-tetrahydro-1H-β-carboline was obtained from the resolution of the corresponding racemic amine with N-acetyl-(L)-Leucine (Sigma) in MeOH followed by a recrystallization from MeOH. Treatment of the suspension of the recrystallized material in DCM with a saturated aqueous solution of NaHCO$_3$ gave the enantiomerically pure (S)-1-(3,4-methylenedioxyphenyl)-2,3,4,9-tetrahydro-1H-β-carboline as beige crystals in a 55% yield.

MP: 173° C.

Analysis for $C_{18}H_{16}N_2O_2$. 0.35H$_2$O:

Calculated: C,72.39; H,5.64; N,9.38.

Found: C,72,35; H,5.44; N,9.1%.

$[\alpha]_D^{19.6}$=−35 (c=0.53, MeOH).

Intermediate 19

(R)-1-(3,4-Methylenedioxyphenyl)-2,3,4,9-tetrahydro-1H-β-carboline

Following the same protocol as for Intermediate 18 (R)-1-(3,4-methylenedioxyphenyl)-2,3,4,9-tetrahydro-1H-β-carboline was obtained from the resolution of the corresponding racemic amine with N-acetyl-(D)-Leucine (Sigma) in MeOH followed by a recrystallization from MeOH. Treatment of the suspension of the recrystallized material in DCM with a saturated aqueous solution of NaHCO$_3$ gave the enantiomerically pure (R)-1-(3,4-methylenedioxyphenyl)-2,3,4,9-tetrahydro-1H-β-carboline as white crystals in a 59% yield.

MP: 92–94° C.

Analalysis for $C_{18}H_{16}N_2O_2$:

Calculated: C,73.95; H,5.52; N,9.58.

Found: C,73.72; H,5.52; N,9.52%.

$[\alpha]_D^{21}$=34(c=0.50, MeOH).

Intermediate 20

(R)-1-(2,3-Dihydrobenzofuran-5-yl)-2,3,4,9-tetrahydro-1H-β-carboline

Following the same protocol as for Intermediate 18 (R)-1-(2,3-dihydrobenzofuran-5-yl)-2,3,4,9-tetrahydro-1H-β-carboline was obtained from the resolution of the corresponding racemic amine with N-acetyl-(D)-Leucine (Sigma) in MeOH:EtOAc followed by a recrystallization from MeOH. Treatment of the suspension of the recrystallized material in DCM with a saturated aqueous solution of NaHCO$_3$ gave the enantiomerically pure (R)-1-(2,3-dihydrobenzofuran-5-yl)-2,3,4,9-tetrahydro-1H-β-carboline as white crystals in a 55% yield.
MP: 98–99° C.
Analysis for C$_{19}$H$_{18}$N$_2$O. 0.15H$_2$O:
Calculated: C,77.87; H,6.29; N,9.56.
Found: C,77.83; H,6.33; N,9.44%
[α]$_D^{21}$=42 (c=0.50, MeOH).

Intermediate 21

(S)-1-(4-(2,3-Dihydrobenzo(b)furan)-2,3,4,9-tetrahydro-1H-β-carboline

Following the same protocol as for Intermediate 18 (S)-1-(2,3-dihydrobenzofuran-5-yl)-2,3,4,9-tetrahydro-1H-β-carboline was obtained from the resolution of the corresponding racemic amine with N-acetyl-(L)-Leucine (Sigma) in MeOH/EtOAc followed by a recrystallization from MeOH. Treatment of the suspension of the recrystallized material in DCM with a saturated aqueous solution of NaHCO$_3$ gave the enantiomerically pure (S)-1-(2,3-dihydrobenzofuran-5-yl)-2,3,4,9-tetrahydro-1H-β-carboline as a pale yellow powder in a 45% yield.
MP: 175° C.
Analalysis for C$_{19}$H$_{18}$N$_2$O. 1.0H$_2$O:
Calculated: C,74.0; H,6.54; N,9.08.
Found: C,74.01; H,5.88; N,8.92%.
[α]$_D^{19.7}$=49 (c=0.50, MeOH).

Intermediate 22

(E)-3-(4-Ureidophenyl)acrylic Acid

A stirred solution of (E)-3-(4-aminophenyl)acrylic acid (1.0 g, 5.0 mmol) and potassium isocyanate (2.0 g, 5 equiv.) in a mixture of water and acetic acid (50 mL) was heated at 100° C. for 12 hours. After cooling, a white solid precipitated out. Filtration, washing of the filter cake with a mixture of water and MeOH, and drying it in vacuo gave the title compound (0.82 g, 80%) as a white solid.
MP>350° C.

Intermediate 23

(E)-3-(4-Acetylmethylaminophenyl)acrylic Acid

A stirred solution of N-(4-formylphenyl)-N-methylacetamide (1.0 g, 5.64 mmol), malonic acid (1.06 g, 1.8 equiv.) and piperidine (0.1 g, catalytic amount) in pyridine (3.5 mL) was heated at 60° C. for 12 hours. Pouring the resulting mixture into HCl (1N) gave a precipitate. Filtration gave the title compound (1.2 g, 98%) as a white solid.
MP: 213–215° C.
Analysis for C$_{12}$H$_{13}$NO$_3$. 0.2H$_2$O:
Calculated: C,64.68; H,6.06; N,6.29;
Found: C,64.43; H,6.18; N,6.36%.

N-(4-Formylphenyl)-N-methylacetamide (1.0 g, 46%) was obtained as an oil from N-(4-formylphenyl)acetamide (2.0 g, 12.2 mmol) in THF in the presence of iodomethane (1.2 mL, 1.5 equiv.) and NaH (0.73 g, 1.5 equiv., 60% in mineral oil).
$^1$H NMR (CDCl$_3$, 250 MHz) δ2.0 (s, 3H), 3,4 (s, 3H), 7.4 (d, 2H), 8.0 (d, 2H).

Intermediate 24

(E)-3-[4-(2-Methoxyethylcarbambyl)phenyl]acrylic Acid

The same method was employed as in the preparation of Intermediate 23 but starting from 4-formyl-N-(2-methoxyethyl)benzamide to give the title compound as a white powder in a 57% yield.
MP: 205° C.

4-Formyl-N-(2-methoxyethyl)benzamide (158 mg, 48%) was obtained by oxidation of 4-hydroxymethyl-N-(2-methoxyethyl)benzamide (330 mg, 1.6 mmol) in DCM in the presence of MnO$_2$ (3.0 g, 22 equiv.).
$^1$H NMR (CDCl$_3$, 250 MHz) δ9.9 (s, 1H), 7.8 (s, 4H), 6.8 (s, 1H), 3.4–3.6 (m, 4H), 3.2 (s, 3H).

4-Hydroxymethyl-N-(2-methoxyethyl)benzamide (330 mg, 14%) was obtained as an oil (Rf=0.7, DCM:MeOH (9:1)) by coupling 4-(hydroxymethyl)benzoic acid (1.0 g, 6.5 mmol) with 2-methoxyethylamine (0.6 mL, 6.5 mmol) in the presence of Et$_3$N (0.95 mL, 1.0 equiv.), EDCl (1.2 g, 1.0 equiv.) and HOBT (0.88 g, 1.0 equiv.).

Intermediate 25

(E)-[4-(2-Dimethylaminoethoxy)phenyl]acrylic Acid

The same method was employed as in the preparation of Intermediate 23 but starting from 4-(2-dimethylaminoethoxy)benzaldehyde to give the title compound as a white powder in a 100% yield.
MP: 243° C.

4-(2-Dimethylaminoethoxy)benzaldehyde (20.6 g, 65%) was obtained by alklylation of 4-hydroxybenzaldehyde (20 g, 164 mmol) in DMF with dimethylaminoethyl chloride (144 g, 8 equiv.) and K$_2$CO$_3$ (24,9 g, 1.1 equiv.) for 16 hours at 80° C.
$^1$H NMR (CDCl$_3$, 250 MHz) δ9.85 (s, 1H), 7.9–7.8 (d, 2H), 7–6.9 (d, 2H), 4.2 (t, 2H), 2.7 (t, 2H), 2,3 (s, 6H).

Intermediate 26

(E)-3-[4-(2-Morpholin-4-yl-ethylcarbamoyl)phenyl]acrylic Acid

The same method was employed as in the preparation of Intermediate 23 but starting from 4-formyl-N-(2-morpholin-4-yl-ethyl)benzamide to give the title compound as a gummy solid.

4-Formyl-N-(2-morpholin4-yl-ethyl)benzamide (0.14 g, 55%) was obtained by oxidation of 4-hydroxymethyl-N-(2-morpholin-4-yl-ethyl)benzamide (0.24 g. 0.9 mmol) and MnO$_2$ (1.73 g, 20 mmol).
$^1$H NMR (CDCl$_3$, 250 MHz) δ10 (s, 1H), 7.9 (s, 4H), 6.8 (s, 1H), 3.5 (t, 5H), 2.6 (t, 2H), 2,3 (m, 5H).

4-Hydroxymethyl-N-(2-morpholin4-yl-ethyl)benzamide (240 mg, 14%) was obtained as a colourless oil (Rf=0.6, DCM:MeOH (9:1)) by coupling 4-(hydroxymethyl)benzoic acid (1.0 g, 6.5 mmol) with 2-morpholinethylamine (0.85 g (1.0 equiv.) in the presence of Et$_3$N (0.95 mL, 1.0 equiv.), EDCl (1.2 g, 1.0 equiv.) and HOBT (0.88 g, 1.0 equiv.).

Intermediate 27

(E)-3-(4-Cyclohexylcarbamoylphenyl)acrylic Acid

The same method was employed as in the preparation of Intermediate 23 but starting from N-cyclohexyl-4-formylbenzamide to give the title compound as a white powder in a 54% yield.
MP: 214° C.

N-Cyclohexyl-4-formylbenzamide (0.6 g, 60%) was obtained by oxidation of N-cyclohexyl-4-(hydroxymethyl)benzamide (1.0 g, 4.29 mol) with MnO$_2$ (0.2 g, 22 equiv.), as a white powder.
MP: 163° C.
$^1$H NMR (CDCl$_3$, 250 MHz) δ10 (s, 1H), 7.95 (s, 4H), 6.6 (s, 1H), 4.1 (m, 1H), 3.9–3.7 (m, 3H), 3.4–3.3 (m, 1H), 2.1–1.9 (m, 2H); 1.8–1.7 (m, 2H).

N-Cyclohexyl-4-(hydroxymethyl)benzamide(1.0 g, 66%) was obtained as white crystals by coupling 4-(hydroxymethyl)benzoic acid with cyclohexylamine (0.75 mL, 1 equiv.) in the presence of Et$_3$N (0.95 mL, 1.0 equiv.), EDCl (1.2 g, 1.0 equiv.) and HOBT (0.88 g, 1.0 equiv.).
MP: 185° C.
$^1$H NMR (CDCl$_3$, 250 MHz) δ7.8–7.7 (d, 2H), 7.5–7.4 (d, 2H), 6.8 (s, 1H), 4.8 (s, 2H), 4.2 (m, 1H), 4.0–3.75 (m, 2H), 3.4–3.3 (m, 1H), 2.7 (m, 1H), 2–1.9 (m, 2H), 1.6 (m, 1H), 1.1 (m, 1H).

Intermediate 28
(E)-3-{4-[(Tetrahydrofuran-2-ylmethyl)carbamoyl] phenyl}acrylic Acid The same method was employed as in the preparation of Intermediate 23 but starting from 4-formyl-N-(tetrahydrofuran-2-ylmethyl)benzamide to give the title compound as a white powder in a 49% yield.

MP: 215° C.

4-Formyl-N-(tetrahydrofuran-2-ylmethyl)benzamide (0.36 g, 50%) (Rf=0.3, DCM:MeOH) was obtained as an oil by oxidation of 4-hydroxymethyl-N-(tetrahydrofuran-2-ylmethyl)benzamide (0.72 g, 3.0 mmol) with $MnO_2$ (0.36 g, 22 equiv.).

4-Hydroxymethyl-N-(tetrahydrofuran-2-ylmethyl) benzamide (0.72 g, 46%) was obtained as a colourless oil (Rf=0.6, DCM:MeOH (9:1)) by coupling 4-(hydroxymethyl)benzoic acid (1.0 g, 6.5 mmol) with tetrahydrofuran-2-yl-methylamine (0.67 mL, 1.0 equiv.) in the presence of $Et_3N$ (0.95 mL, 1.0 equiv.), EDCl (1;2 g, 1.0 equiv.) and HOBT (0.88 g, 1.0 equiv.).

Intermediate 29
(E)-1-[4-(2-Carboxyvinyl)benzoyl]piperidine-4carboxylic Acid, Ethyl Ester The same method was employed as in the preparation of lntermediate 23 but starting from 1-(4-formylbenzoyl) piperidine-4-carboxylic acid, ethyl ester to give the title compound as a white powder in a 46% yield.

MP: 165° C.

1-(4-Formylbenzoyl)piperidine-4-carboxylic acid, ethyl ester (960 mg, 49%) (Rf=0.6, DCM:MeOH(95:5)) was obtained as an oil by oxidation of 1-(4-hydroxymethylbenzoyl)piperidine-4-carboxylic acid, ethyl ester (2.0 g, 6.8 mmol) with $MnO_2$ (13.1 g, 22 equiv.).

$^1$H NMR ($CDCl_3$, 250 MHz) δ10.0 (s, 1H), 7.9 (d, 2H), 7.5 (d, 2H), 4.5 (d, 1H), 4.1 (q, 2H), 3.6 (d, 1H), 3.1 (br s, 2H), 2.5 (m, 1H), 2.1–1.6 (m, 4H), 1.2 (t, 3H).

1-(4-Hydroxymethylbenzoyl)piperidine-4-carboxylic acid, ethyl ester (1.9 g, 100%) was obtained as a colorless oil (Rf=0.1, DCM:MeOH (95:5)) by coupling 4-(hydroxymethyl)benzoic acid (1.0 g, 6.5 mmol) with 4-piperidine-4-carboxylic acid, ethyl ester (1 mL, 6.5 mmol ) in the presence of $Et_3N$ (0.95 mL, 1.0 equiv.), EDCl (1.2 g, 1.0 equiv.) and HOBT (0.88 g, 1.0 equiv.).

$^1$H NMR ($CDCl_3$, 250 MHz) δ7.2 (s, 4H), 4.5 (s, 2H), 4.3 (br s, 1H), 4.1 (q, 2H), 3.6 (br s, 1H),3 (t, 2H), 2.5 (m, 1H), 2.1–1.6 (m, 4H), 1.2 (t, 3H).

Intermediate 30
(E)-3-(4-Ethoxycarbonylmethylphenyl)acrylic Acid

The same method was employed as in the preparation of Intermediate 23 but starting from (4-formylphenyl)acetic acid, ethyl ester gave the title compound as a yellow gum in a 52% yield.

$^1$H NMR ($CDCl_3$, 250 MHz) δ7.8–7.6 (m, 3H), 7.4–7.3 (d, 2H), 6.9–6.8 (d, 1H), 4.1–3.9 (q, 2H), 3.55 (s, 2H), 1.2 (t, 3H).

4-(4-Formylphenyl)acetic acid, ethyl ester was prepared according to the procedure of Biagi, G.; Livi, O.; Verugi, E. *Farmaco-Ed. Sc.* 1988, 43, 597–611.

Intermediate 31
(E)-1-[4-(2-Carboxyvinyl)phenyl]piperidine-4-carboxylic Acid, Ethyl Ester The same method was employed as in the preparation of Intermediate 23 but starting from 1-(4-formylphenyl) piperidine-4carboxylic acid, ethyl ester to give the title compound as a yellow powder in a 86% yield.

MP: 212° C.

Analysis for $C_{17}H_{21}NO_4 \cdot 0.15H_2O$:

Calculated: C,66.71; H,7.01; N,4.58;
Found: C,66.77; H,7.01; N,4.79%.

1-(4-Formylphenyl)piperidine-4-carboxylic acid, ethyl ester was prepared according to the procedure of Duckworth, D. M. Hindley, R.; Richard, M. EP 68669A1.

Intermediate 32
(E)-4-(2-Carboxyvinyl)-3-chlorobenzoic Acid, Methyl Ester

The same method was employed as in the preparation of Intermediate 23 but starting from 3-chloro-4-formylbenzoic acid, methyl ester to give the title compound as a white powder in a 58% yield.

MP: 221° C.

3-Chloro4-formylbenzoic acid, methyl ester (4.0 g, 81%) was prepared by reaction of 4-bromomethyl-3-chlorobenzoic acid, methyl ester (6.0 g, 26 mmol) with silver p-toluenesulfonate (15.0 g, 2.0 equiv.) in 100 mL of DMSO in the presence of $Et_3N$ (100 mL, 7 equiv.) at rt for 1 hour. Quenching the resulting mixture with 100 mL of water, extraction with 2×100 mL of EtOAc, washing with 50 mL of water, drying over $Na_2SO_4$ and flash chromatography with cyclohexane:EtOAc (95:5) as eluting solvent, gave the title compound (2,3 g9 42%) as an oil.

$^1$H NMR ($CDCl_3$, 250 MHz) δ10.5 (s, 1H), 8.1 (s, 1H), 7.8–7.7 (d, 1H), 7.4–7.3 (d, 1H), 3.8 (s, 3H).

4-Bromomethyl-3-chlorobenzoic acid, methyl ester (6.0 g, 87%) was obtained as an orange oil by refluxing for 12 hours 4-methyl-3-chlorobenzoic acid, methyl ester (5.7 g, 31 mmol) with NBS (6.4 g, 1.2 equiv.) in the presence of a catalytic amount of AIBN in $CCl_4$.

$^1$H NMR ($CDCl_3$, 250 MHz) δ8.0 (s, 1H), 7.9–7.8 (d, 1H), 7.45–7.35 (d, 1H), 4.5 (s, 1H), 3.9 (s, 3H).

4-Methyl-3-chlorobenzoic acid, methyl ester (5.7 g, 53%) was obtained as an orange oil by refluxing overnight 4-methyl-3-chlorobenzoic acid (9.9 g, 58 mmol) in MeOH in the presence of PTSA.

$^1$H NMR ($CDCl_3$, 250 MHz) δ8.0 (d, 1H), 7.85 (dd, 1H), 7.3 (d, 1H), 4.0 (s, 3H), 2.5 (s, 3H).

Intermediate 33
(E)-5-(2-Carboxyvinyl)-2-chlorobenzoic Acid, Methyl Ester

The same method was employed as in the preparation of Intermediate 32 but starting from 2-chloro-5-formylbenzoic acid, methyl ester to give the title compound as a yellow powder in a 76% yield.

MP: 194° C.

2-Chloro-5-formylbenzoic acid, methyl ester (0.6 g, 25%) was obtained a gum by reaction of 5-bromomethyl-2-chlorobenzoic acid, methyl ester (3.1 g, 11.7 mmol) with silver p-toluenesulfonate (6.4 g, 1.75 equiv.) in DMSO in the presence of $Et_3N$ (1.2 mL, 7 equiv.) at rt for 1 hour.

$^1$H NMR ($CDCl_3$, 250 MHz) δ10 (s, 1H), 8.4 (d, 1H), 7.9 (dd, 1H), 7.7–7.6 (d, 1H), 4.0 (s, 3H).

5-Bromomethyl-2-chlorobenzoic acid, methyl ester (3.1 g, 11.7 mmol) was obtained as a gum in a 45% yield by refluxing for 12 hours 5-methyl-2-chlorobenzoic acid, methyl ester (4.78 g, 25.9 mmol) with NBS (5.56, 1.2 equiv.) in the presence of a catalytic amount of AIBN in $CCl_4$.

$^1$H NMR ($CDCl_3$, 250 MHz) δ7.9 (s, 1H), 7.4 (br s, 2H) 4.5 (s, 2H), 3.9 (s, 3H).

5-Methyl-2-chlorobenzoic acid, methyl ester (4.78 g, 90%) was obtained as a brown oil, by refluxing overnight 3-methyl-4-chlorobenzoic acid (5.0 g, 29 mmol) in MeOH in the presence of a catalytic amount of PTSA.

$^1$H NMR ($CDCl_3$, 250 MHz) δ7.6 (s, 1H), 7.25–7.2 (d, 1H), 7.15–7.1 (d, 1H), 3.8 (s, 3H), 2.2 (s, 3H).

Intermediate 34
(E)-(3-Hydroxy-4-nitrophenyl)acrylic Acid

The same method was employed as in the preparation of Intermediate 23 but starting from 3-hydroxy-4- nitrobenzaldehyde to give the title compound as a white powder in a 88% yield.

MP: 237° C.

Intermediate 35

(E)-(3,5-Dimethyl-4-hydroxyphenyl)acrylic Acid

The same method was employed as in the preparation of Intermediate 23 but starting from 3,5-dimethyl-4-hydroxybenzaldehyde gave the title compound as a white powder in a 94% yield.

MP: 190° C.

Intermediate 36

(E)-(3-Nitro-4-hydroxy-5-methoxphenyl)acrylic Acid

The same method was employed as in the preparation of Intermediate 23 but starting from 3-nitro-4-hydroxy-5-methoxybenzaldehyde to give the title compound as a white powder in a 75% yield.

MP: 248° C.

Intermediate 37

(E)-3-(3-Nitro-2-piperidin-1-yl-phenyl)acrylic Acid

The same method was employed as in the preparation of Intermediate 23 but starting from 2-chloro-3-nitrobenzaldehyde to give the title compound as a yellow powder in a 100% yield.

$^1$H NMR (CDCl$_3$, 250 MHz) δ10.3 (br s, 1H), 8.1 (d,1H), 7.65 (dd, 1H), 7.55 (dd, 1H), 7.05 (t, 41H), 6.3 (d, 1H), 2.9 (m, 2H), 1.6 (m, 6H).

2-Chloro-3-nitrobenzaldehyde (150 mg, 20%) was prepared by reaction of 1-bromomethyl-2-chloro-3-nitrobenzene (1.0 g, 3.9 mmol) with silver p-toluenesulfonate (1.94 g, 1.75 equiv.) in DMSO in the presence of Et$_3$N (4 mL, 7 equiv.) at rt for 1 hour.

$^1$H NMR (CDCl$_3$, 250 MHz) δ10.5 (s, 1H), 8.1 (dd, 1H), 8.0 (dd, 1H), 7.5 (t, 1H). 1-Bromomethyl-2-chloro-3-nitrobenzene (13.3 g, 68%) was obtained as a yellow oil by refluxing for 2 hours a mixture of 2-chloro-3-nitrotoluene (10 g, 58 mmol) with NBS (10.3 g, 1 equiv.) in the presence of a catalytic amount of AIBN in CCl$_4$.

$^1$H NMR (CDCl$_3$, 250 MHz) δ7.75 (dd, 1H), 7.65 (dd, 1H), 7.45 (m, 1H), 4.6 (s, 2H).

Intermediate 38

(E)-3-(4-Methyl-3,4-dihydro-2H-benzo[1,4]oxazin-6-yl) acrylic Acid

The same method was employed as in the preparation of Intermediate 23 but starting from 4-methyl-3,4-dihydro-2H-benzo[1,4]oxazin-6-carboxaldehyde (prepared according to the procedure of Kotha, S.; Bindra, V.; Kuki, A. *Heterocyles* 1994, 38, 5–8) to give the title compound as a yellow powder in a 61% yield

MP: 190° C.

Analysis for C$_{12}$H$_{13}$NO$_5$:

Calculated: C,65.74; H,5.98; N,6.39;

Found: C,65.85; H,6.04; N,6.33%.

Intermediate 39

(E)-3-(2-Hydroxy-5-nitrophenyl)acalic Acid

The same method was employed as in the preparation of Intermediate 23 but starting from 2-hydroxy-5-nitro benzaldehyde to give the title compound as a yellow powder in a 11% yield.

MP: 265–267° C.

Intermediate 40

(E)-3-[3-(Trifluoromethanesulfonyloxy)phenyl]acrylic Acid

The same method was employed as in the preparation of Intermediate 23 but starting from trifluoromethanesulfonic acid, 3-formylphenyl ester (prepared according to the procedure of Kingsbury, W. D.; Pendrak, I.: Leber, J. D.: Boehm, J. C.; Mallet, B.; Sarau, H. M.; Foley, J. J.; Schmidt, D. B.; Daines, R. A. *J. Med. Chem.* 1993, 36, 3308–3320) to give the title compound as pink crystals in a 36% yield.

MP: 107° C.

Intermediate 41

(E)-3-[4-(Trifluoromethanesulfonyloxy)phenyl]acrylic Acid

The same method was employed as in the preparation of Intermediate 23 but starting from trifluoromethanesulfonic acid, 4-formylphenyl ester (prepared according to the procedure of Creary, X.; Benage, B.; Hilton, K. *J. Org. Chem.* 1983, 48(17), 2887–2891) to give the title compound as white crystals in a 61% yield.

MP: 194° C.

Intermediate 42

(E)-3-[4-(2-Pyrrolidin-1-ylethoxy)phenyl]acrylic Acid

The same method was employed as in the preparation of Intermediate 23 but starting from 4-(2-pyrrolidin-1-ylethoxy)benzaldehyde (prepared according to the procedure of Sakaguchi, J.; Nishino, H.; Ogawa, N.; Iwanaga, Y.; Yasuda, S.; Kato, H.; Ito, Y. *Chem. Pharm. Bull.* 1992, 40, 202–211) to give the title compound as a yellow solid in a 60% yield.

MP: 183° C.

Intermediate 43

(E)-3-(4-Pyrrolidin-1-ylphenyl)acrylic Acid

The same method was employed as in the preparation of Intermediate 23 but starting from (4-pyrrolidin-1-ylphenyl) benzaldehyde (prepared according to the procedure of Duckworth, D. M. Hindley, R.; Richard, M. EP 68669A1) to give the title compound as a yellow solid in a 65% yield.

MP: 265° C.

Intermediate 44

(E)-3-(4-Imidazol-1-ylphenyl)acrylic Acid

The same method was employed as in the preparation of Intermediate 23 but starting from 4-imidazol-1-ylbenzaldehyde (prepared according to the procedure of Sircar, I.; Duell, B.; Bristol, J. A.; Weishaar, R. E.; Evans, D. B. *J. Med. Chem.* 1987, 30, 1023–1029) to give the title compound as pink crystals in a 55% yield.

MP: 326–327° C.

Intermediate 45

(E)-(S)-3-[4-(1-Methylpyrolidin-2-ylmethoxy)phenyl] acrylic Acid

The same method was employed as in the preparation of Intermediate 23 but starting from (S)-4-(1-methylpyrrolidin-2-ylmethoxy)benzaldehyde to give the title compound as a beige powder in a 66% yield.

MP: 251° C.

$[α]_D^{21}$ =−9(c=0.35, pyridine).

(S)-4-(1-Methylpyrrolidin-2-ylmethoxy)benzaldehyde (0.96 g, 44%) was obtained as an orange oil by refluxing for 12 hours at 80° C., 4-hydroxybenzaldehyde (1.22 g, 10 mmol) with (S)-2-chloromethyl-1-methylpyrrolidine, hydrochloride (2.55 g, 1.5 equiv.) in DMF in the presence of K$_2$CO$_3$ (3.82 g, 2.8 equiv).

$^1$H NMR (CDCl$_3$, 250 MHz) δ9.9 (s, 1H), 7.85 (d, 2H), 7.0 (d, 2H), 4.1 (dd, 1H), 4.0 (dd,1H), 3.1 (d tr, 1H), 2.7 (m, 1H), 2.5 (s, 3H), 2,3 (m, 1H), 2 (m, 1H), 1.8 (m, 3H).

(S)-2-Chloromethyl-1-methylpyrrolidine, hydrochloride was prepared according to the procedure of D'Ambra, T. E.; Bacon, E. R.; Edward, R.; Bell, M. R., Carabateas, P. M.; Eissenstat, M. A.; Kumar, V.; Mallamo, J. P.; Ward, S. J. EP 444451 A2.

Intermediate 46

(E)-3-[4-(2-Dimethylamino-1-methylethoxy)phenyl]acrylic Acid

The same method was employed as in the preparation of Intermediate 23 but starting from 4-(2-dimethylamino-1- methylethoxy)benzaldehyde to give the title compound as a white powder in a 86% yield.

MP: 235° C.
Analysis for $C_{14}H_{19}NO_3.HCl$:
Calculated: C,58.84; H,7.05; N,4,9;
Found C,58.49; H,7.08; N,5.05%.

4-(2-Dimethylamino-1-methylethoxy)benzaldehyde (2.1 g, 18%) was obtained as an orange oil by refluxing for 12 hours, 4-hydroxybenzaldehyde (7 g, 57 mmol), $K_2CO_3$ (8.7 g, 1.1 equiv.) and 2-chloropropyldimethylamine, hydrochloride (13.6 g, 1.5 equiv.) in DMF.
$^1$H NMR (CDCl$_3$, 250 MHz) δ9.7 (s, 1H), 7.65 (d, 2H), 6.85 (d, 2H), 4.5 (m, 1H), 2.5 (m, 1H), 2,3 (m, 1H), 2.1 (m, 6H), 1.2 (d, 3H).

Intermediate 47
(E)-3-[4-(4-Methylpiperazin-1-yl)phenyl]acrylic Acid

The same method was employed as in the preparation of Intermediate 23 but starting from 4-(4-methylpiperazin-1-yl)benzaldehyde (prepared according to the procedure of Sakai, K.; Suzuki, M.; Nunami, K.; Yoneda, N.; Onoda, Y. Iwasawa, Y. Chem. Pharm. Bull. 1980, 28, 2384–2393) to give the title compound as a white powder in a 65% yield.
MP: 223–226° C.

Intermediate 48
(E)-3-[4-(2-Dimethylaminopropoxy)phenyl]acrylic Acid

The same method was employed as in the preparation of Intermediate 23 but starting from 4-(2-dimethylaminopropoxy)benzaldehyde (prepared according to the procedure of Mizzoni, R. H. U.S. Pat. No. 3,483,209) to give the title compound as a beige powder in a 100% yield.
MP: 231° C.

Intermediate 49
(E)-3-[4-(2-Morpholin-4-ylethoxy)phenyl]acrylic Acid

The same method was employed as in the preparation of Intermediate 23 but starting from 4-(2-morpholin-4-ylethoxy)benzaldehyde (prepared according to the procedure of Naruto, S.; Mizuta, H.; Sawayama, T.; Yoshida, T.; Uno, H.; Kawashima, K.; Sohji, Y.; Kadokawa,T.; Nishimura, H. J. Med. Chem. 1982, 25, 1240–1245) to give the title compound as a white powder in a 96% yield.
MP: 228° C.

Intermediate 50
(E)-3-{4-[2-(Ethylmethylamino)ethoxy]phenyl}acrylic Acid

The same method was employed as in the preparation of Intermediate 23 but starting from 4-[2-(ethylmethylamino)ethoxy]benzaldehyde to give the title compound as a beige powder in a 73% yield.
MP: 206° C.
Analysis for $C_{14}H_{19}NO_3.HCl$:
Calculated: C,58.84; H,7.05; N,4,9;
Found C,59.08; H,7.07; N,5.02%.

4-[2-(Ethylmethylamino)ethoxy]benzaldehyde(5.0 g, 59%) was obtained as a brown oil by refluxing for 12 hours 4-hydroxybenzaldehyde (5 g, 41 mmol), $K_2CO_3$ (6.2 g, 1.1 equiv.) and (2-chloroethyl)ethylmethylamine, hydrochloride (9.7 g, 1.5 equiv.) in DMF.
$^1$H NMR (CDCl$_3$, 250 MHz) δ9.7 (s, 1H), 7.7 (d, 2H), 6.9 (d, 2H), 4.1 (t, 2H), 2.6 (t, 2H), 2. (s, 6H).

Intermediate 51
(E)-3-[4-(3-Dimethylaminopropenyl)phenyl]acrylic Acid

This product was prepared by refluxing for four hours, (E)-3-[4-(3-dimethylaminopropenyl)phenyl]acrylic acid, methyl ester with NaOH (0.16 g, 2 equiv.) in 10 mL of MeOH. After evaporation of the solvent in vacuo, treatment with 5 mL of HCl (1N) gave the title compound (0.4 g, 85%) as a gummy orange solid.

$^1$H NMR (CDCl$_3$, 250 MHz) δ7.6 (d, 2H), 7.4 (d, 1H), 7.2 (d, 2H), 6.6 (d, 1H), 6.4 (d, 1H), 5.8 (m, 1H), 3.7 (d, 2H), 2.6 (s, 6H).

(E)-3-[4-(3-Dimethylaminopropenyl)phenyl]acrylic acid, methyl ester was prepared by the following way: (2-dimethylaminoethyl)triphenylphosphonium bromide (7.2 g, 17.4 mmol) in 30 mL of DMF was treated with KHMDS (27 mL, 1.01 equiv., 0.5 M in toluene) at −78° C. for one hour. At −40° C., 3-(4-formylphenyl)acrylic acid, methyl ester (2.54 g, 13.3 mmol, prepared according to the procedure of Syper, L.; Miochowski, J. Synthesis, 1984, 9, 747–752) was added dropwise. The resulting mixture was stirred for 12 hours at rt and quenched with water. Extraction with EtOAc, drying over MgSO$_4$ and evaporation in vacuo gave a residue that was purified via flash chromatography with DCM:MeOH (90:10) as eluting solvent. The title compound (1.1 g, 34%) was obtained as an orange oil.
$^1$H NMR (CDCl$_3$, 250 MHz) δ7.6 (d, 1H), 7.4 (d, 2H), 7.2 (d, 2H), 6.5 (d, 1H), 6.4 (d, 1H), 5.8 (m, 1H), 3.2 (dd, 2H), 2.1 (s, 6H).

Intermediate 52
(E)-3-[4-(2-(Tertbutyldimethylsilanyloxy)-3-dimethylaminopropenyl)phenyl]acrylic Acid This product was prepared by refluxing for four hours (E)-3-[4-(2-(tertbutyldimethylsilanyloxy)-3-dimethylaminopropanyl)phenyl]acrylic acid, methyl ester (0.8 g, 2.03 mmol) and NaOH (1N) (4 mL, 2 equiv.) in 10 mL of MeOH. Evaporation of the solvent in vacuo and treatment with 5 mL of HCl (1 N) gave the title compound (0.4 g, 60%) as a beige solid solid.
MP: 207° C.

(E)-3-[4-(2-(Tertbutyldimethylsilanyloxy)-3-dimethylaminopropoxy)phenyl]acrylic acid, methyl ester (0.8 g, 40%) was obtained as a yellow oil by reaction for 4 hours of (E)-3-[4-(3-dimethylamino-2-hydroxypropoxy) phenyl]acrylic acid, methyl ester (1.35 g, 5.13 mmol) with TBDMSCl (0.93 g, 6.2 mmol) in 50 mL of DMF in the presence of imidazole (0.84 g, 2.4 equiv.). After evaporation in vacuo, the residue was taken up in DCM, washed with water, dried over MgSO$_4$, evaporated in vacuo and purified via flash chromatography using DCM:MeOH as eluting solvent.
$^1$H NMR (CDCl$_3$, 250 MHz) δ7.5 (d, 1H), 7.3 (d, 2H), 6.8 (d, 2H), 6.2 (d, 1H), 4.0 (m, 2H), 3.8 (m, 1H), 3.7 (s, 3H), 2.4–2.2 (m, 2H), 2.1 (s, 6H), 0.7 (s, 9 H), 0.0 (d, 6H).

(E)-3-[4-(3-Dimethylamino-2-hydroxypropoxy)phenyl] acrylic acid, methyl ester (1.5 g, 60%) was obtained as an oil by reaction of 4-(3-dimethylamino-2-hydroxypropoxy) benzaldehyde (2.0 g, 8.96 mmol) in 80 mL of toluene with triphenylphosphoranylidene methyl acetate (3.6 g, 1.2 equiv.) at 100° C. for one day. After concentration in vacuo, the residue was taken up in DCM, washed with water, dried over Na$_2$SO$_4$, evaporated in vacuo and purified via flash chromatography using DCM:MeOH (95:5) as eluting solvent.
$^1$H NMR (CDCl$_3$, 250 MHz) δ7.6 (d, 1H), 7.5 (d, 2H), 7.3 (d, 2H), 6.3 (d, 1H), 4.2 (m, 1H), 4.1 (m, 1H), 3.8 (m, 3H), 3.3 (s, 1H), 2.8 (dd, 1H), 2.6 (dd, 1H), 2.4 (s, 6H).

4-(3-Dimethylamino-2-hydroxypropoxy)benzaldehyde (8.2 g, 61%) was obtained as an yellow oil, by reaction of 4-oxiranylmethoxybenzaldehyde (6 g, 33.6 mmol, prepared according to the procedure of Baldwin, J. J., Hirchmann, R.; Lumma, W. C.; Ponticello, G. S.; Sweet, C. S.; Scriabine, A. J. Med. Chem. 1977, 20, 1024–1029) in 100 mL of MeOH with dimethylamine (34 mL, 2 equiv.). The resulting mixture was stirred at reflux for 2 days. Evaporation in vacuo gave a residue that was taken up in DCM, washed with brine and dried over MgSO$_4$ and evaporated in vacuo.

¹H NMR (CDC₃, 250 MHz) δ9.7 (s, 1H), 7.6 (d, 2H), 7.0 (d, 2H), 4. (m, 3H), 3.6 (s, 1H), 2.5 (dd, 1H), 2,3 (dd, 1H), 2.25 (s, 6H).

Intermediate 53

(E)-3-[4-(2-(Dimethylaminoethylamino)phenyl]acrylic Acid

The same method was employed as in the preparation of Intermediate 23 but starting from 4-[2-(dimethylaminoethyl)amino]benzaldehyde (prepared according to the procedure of Klaus, M.; Mohr, P.; Weiss, E. EP 331983 A2) to give the title compound as an oil in a 100% yield.

¹H NMR (CDCl₃, 250 MHz) δ7.5 (d, 1H), 7.2 (d, 2H), 6.5 (d 2H), 6.1 (d, 1H) 4.6 (s, 1H), 3.0 (m, 2H), 2.5 (t, 2H), 2.2 (s, 6H).

Intermediate 54

(E)-3-{4-[2-(1,3-Dioxo-1,3-dihydroisoindol-2-yl)ethoxy]phenyl}acrylic Acid

The same method was employed as in the preparation of Intermediate 23 but starting from 4-[2-(1,3-dioxo-1,3-dihydroisoindol-2-yl)ethoxy]benzaldehyde (prepared from the procedure of Hindley, R. M.; Haigh, D.; Cottam, G. P. WO 9207839 A1) to give the title compound as an oil in a 99% yield.

¹H NMR (CDCl3, 250 MHz) δ12.3 (s, 1H), 7.9 (m, 4H), 7.6 (d, 2H), 7.5 (d, 1H), 7.0 (d, 2H), 6.4 (d, 1H), 4.4 (t, 2H), 4.0 (t, 2H).

Intermediate 55

(E)-3-[4-(2-(Piperidin-1-ylethoxy)phenyl]acrylic Acid

The same method was employed as in the preparation of Intermediate 23 but starting from 4-(2-piperidin-1-yl-ethoxy)benzaldehyde (which was prepared according to the procedure of Naruto, S.; Mizuta, H.; Sawayama, T.; Yoshida, T.; Uno, H.; Kawashirna, K.; Sohji, Y.; Kadokawa, T.; Nishimura, H. *J. Med. Chem.* 1982, 25, 1240–1245), to give the title compound as a white powder in a 60% yield.

MP: 231° C.

Intermediate 56

(E)-3-[4-(2-(Tertbutoxycarbonylmethylamino)ethoxy)phenyl]acrylic Acid (E)-3-[4-(2-Methylaminoethoxy)phenyl]acrylic acid (0.8 g, 3.6 mmol) in dioxane (100 mL) was treated with NaOH (2N) (22 mL, 12 equiv.). After one hour of stirring at 70° C., ditertbutyldicarbonate (1.6 g, 2 equiv.) was added slowly. The reaction was judged to be complete after 3 hours of stirring at 70° C. After filtration of the white precipitate, the filtrate was acidified to pH=1 with HCl (1 N). A new white solid precipitated out . Filtration and drying in vacuo gave the title compound (0.6 g, 50%) as white crystals.

¹NMR (CDCl₃, 250 MHz) δ7.8 (d, 1H), 7.65 (d, 2H), 7.0 (d, 2H), 6.4 (d, 1H), 4.25 (t, 2H), 3.7 (t, 2H), 3.1 (s, 3H), 1.5 (s, 9H).

(E)-3-[4-(2-Methylaminoethoxy)phenyl]acrylic acid (1.1 g, 41%) was obtained as a white solid by hydrolysis of (E)-3-[4-(2-methylaminoethoxy)phenyl]acrylic acid, methyl ester (3.0 g, 12.0 mmol) with NaOH (6.0 g, 12 equiv.) in MeOH/THF at 40° C.

MP: 245° C.

(E)-3-[4-(2-Methylaminoethoxy)phenyl]acrylic acid, methyl ester (3.0 g, 70%) was obtained as a yellow oil by reaction of trimethylphosphonoacetate (4.2 g, 23.0 mmol) and n-butyl lithium (9.0 mL, 18.0 mmol, 2.0 M in cyclohexane) at −78° C., followed by the addition of 4-(2-methylaminoethoxy)benzaldehyde (3.2 g, 18.0 mmol) at −40° C. The resulting mixture was stirred at rt for 16 hours, quenched with water, extracted with EtOAc, dried over MgSO₄ and concentrated in vacuo.

¹H NMR (CDCl₃, 250 MHz) δ7.65 (d, 1H), 7.45 (d, 2H), 6.9 (d, 2H), 6.25 (d, 1H), 4.10 (t, 2H), 3.75 (s, 3H), 2.95 (t, 2H), 2.5 (s, 3H).

4-(2-Methylaminoethoxy)benzaldehyde (3.2 g, 51%) was obtained as a yellow oil by reaction of 4-(2-methylaminoethoxy)benzonitrile (7.0 g, 40.0 mmol) with diisobutylaluminum hydride (40 mL, 1.5 equiv., 1.5 M in toluene) in toluene (400 mL) at −78° C. After 4 hours of stirring at −78° C. the resulting mixture was treated with a mixture of water/MeOH (4 mL). At rt an additional 20 mL of water was added. The resulting suspension was filtered on a bed of celite. The celite was washed with Et₂O (3×200 mL). The filtrate was concentrated in vacuo and purified via flash chromatography of silica gel using MeOH:DCM (1:9) as eluting solvent.

¹H NMR (CDCl₃, 250 MHz) δ9.8 (s, 1H), 7.8 (d, 2H), 7.0 (d, 2H), 4.1 (t, 2H), 2.9 (t, 2H), 2.5 (s, 3H).

4-(2-Methylaminoethoxy)benzonitrile (0.6 g, 15%) was obtained as a yellow oil by reaction of 4-(2-chloroethoxy)benzonitrile (2.0 g, 11.0 mmol, prepared according to the procedure of Mizuno, K.; Kimura, Y.; Otsuji, Y. *Synthesis*, 1979, 9, 688) with methylamine (4.3 mL, 5 equiv., 40% in water) at 70° C. for 16 hours. The resulting mixture was extracted with DCM, dried over MgSO₄, concentrated in vacuo and purified via flash chromatography of silica gel using MeOH:DCM (2:8) as eluting solvent, to give the title compound.

¹H NMR (CDCl₃, 250 MHz) δ7.6 (d, 2H), 7.0 (d, 2H), 4.1 (t, 2H), 3.0 (t, 2H), 2.5 (s, 3H).

EXAMPLE 1

(E)-1-(1-Phenyl-1,3,4,9-tetrahydro-β-carbolin-2-yl)-3-phenylprocene-1-one

To a solution of Intermediate 1 (0.2 g, 0.81 mmol) and NaHCO₃ (0.08 g, 1.2 equiv.) in 10 mL of DCM was added (E)-cinnamoyl chloride (0.2 g, 1.5 equiv.). After 4 hours of stirring at rt the reaction was judged to be completed by tlc monitoring (SiO₂, DCM:MeOH 98:2) and was quenched with 5 mL of a saturated aqueous solution of NaHCO₃. The reaction mixture was extracted with DCM, washed with brine (5 mL), dried over MgSO₄ and concentrated in vacuo. Flash chromatography on a 2×20 Cm² column using DCM:MeOH (98:2) as eluting solvent and removal of the solvent in vacuo gave after recrystallization from 2-propanol, the title compound (0.1 g, 33%) as white crystals.

MP: 130–132° C.

Analysis for $C_{26}H_{22}N_2O$:

Calculated: C,82.51; H,5.86; N,7.40;

Found: C,82.24; H,5.93; N,7.36%.

EXAMPLE 2

(E)-1-(1-Phenyl-1,3,4,9-tetrahydro-β-carbolin-2-yl)-3-(4-nitrophenyl)propene-1-one The same method as employed as in the preparation of Example 1 but starting from (E)-4-nitrocinnamoyl chloride gave after recrystallization from iPr₂O:2-propanol (3:1), the title compound as a yellow powder in a 47% yield.

MP: 230–231° C.

Analysis for $C_{26}H_{21}N_3O_3$:

Calculated: C,73.74; H,5.00; N,9.92;

Found: C,73.89; H,5.12; N,9.86%.

EXAMPLE 3

(E)-1-(1-Phenyl-1,3,4,9-tetrahydro-β-carbolin-2-yl)-3-(4-trifluoromethylphenyl)propene-1-one The same method as employed in the preparation of Example 1 but starting from (E)-4-trifluoromethylcinnamoyl chloride gave after recrystallization from pentane, the title compound as a white powder in a 41% yield.

MP: 211° C.

Analysis for $C_{27}H_{21}F_3N_2O \cdot 0.4H_2O$:

Calculated: C,71.48; H,4.84; N,6.17;

Found: C,71.84; H,4.81; N,6.19%.

EXAMPLE 4
(E)-1-(1-Phenyl-1,3,4,9-tetrahydro-β-carbolin-2-yl)-3-(4-methoxyphenyl)propene-1-one The same method as employed in the preparation of Example 1 but starting from (E)-4-methoxycinnamoyl chloride gave after recrystallization from 2-propanol, the title compound as white crystals in a 61% yield.

MP: 160–163° C.
Analysis for $C_{27}H_{24}N_2O_2 \cdot 0.5(2\text{-propanol})$:
Calculated: C,78.06; H,6.44; N,6.39;
Found: C,78.04; H,6.02; N,5.97%.

EXAMPLE 5
(E)-1-[1-(4-Methoxyphenyl)-1,3,4,9-tetrahydro-β-carbolin-2-yl]-3-(4-trifluoromethylphenyl)propene-1-one The same method as employed in the preparation of Example 1 but starting from Intermediate 2 and (E)-4-trifluoromethylcinnamoyl chloride gave after recrystallization from pentane, the title compound as a white powder in a 61% yield.

MP: 130–135° C.
Analysis for $C_{28}H_{23}N_2O_2F_3 \cdot 0.3H_2O$:
Calculated: C,69.79; H,4,94; N,5.81;
Found: C,69.9; H,4.84; N,5.73%.

EXAMPLE 6
(E)-N-[4-[3-Oxo-3-(1-phenyl-1,3,4,9-tetrahydro-β-carbolin-2-yl)propenyl]phenyl]acetamide To a solution of Intermediate 1 (0.2 g, 0.81 mmol) in 40 mL of DCM were added Et₃N (0.13 mL, 1.1 equiv.), DCC (0.18 g, 1.1 equiv.), HOBT (0.12 g, 1.1 equiv.) and (E)-3-(4-acetylaminophenyl)acrylic acid (0.18 g, 1.1 equiv.). After 24 hours of stirring at rt the reaction was judged to be completed by tlc monitoring (SiO₂, DCM:MeOH 95:5) and was quenched with 150 mL of water. A white solid precipitated out and was filtered off. The filtrate was extracted with DCM, washed with brine (5 mL), dried over MgSO₄ and concentrated in vacuo. Flash chromatography on a 2.5×25 cm² column of silica gel using DCM:MeOH (98:2) as eluting solvent and removal of the solvent in vacuo gave the title compound (0.18 g, 51%) as yellow crystals after recrystallization from 2-propanol:pentane.

MP: 177–180° C.
Analysis for $C_{28}H_{25}N_3O_2 \cdot 0.7H_2O$:
Calculated: C,75.05; H,5.94; N,9.38;
Found: C,75.01; H,5.81; N,9.22%.

EXAMPLE 7
(E)-1-[1-(4-Method)(phenyl)-1,3,4,9-tetrahydro-β-carbolin-2-yl]-3-phenylpropene-1-one The same method as employed in the preparation of Example 1 but starting from Intermediate 2 gave the title compound as white crystals in a 56% yield.

MP: 127° C.
Analysis for $C_{27}H_{24}N_2O_2 \cdot 0.5H_2O$:
Calculated: C,77.67; H,6.04; N,6.71;
Found: C,77.91; H,6.0; N,6.73%.

EXAMPLE 8
(E)-1-[1-(3,4-Methylenedioxyphenyl)-1,3,4,9-tetrahydro-β-carbolin-2-yl]-3-phenyl-propene-1-one The same method as employed in the preparation of Example 1 but starting from Intermediate 7 gave after recrystallization from 2-propanol:iPr₂O (2:8), the title compound as white crystals in a 38% yield.

MP: 236–238° C.
Analysis for $C_{27}H_{24}N_2O_2 \cdot 0.5H_2O$:
Calculated: C,76.76; H,5.25; N,6.63;
Found: C,76.87; H,5.35; N,6.54%.

EXAMPLE 9
(E)-1-(1-Phenyl-1,3,4,9-tetrahydro-β-carbolin-2-yl)-3-(4-formylphenyl)propene-1-one The same method as employed in the preparation of Example 6 but starting from (E)-4-formylcinnamic acid gave after recrystallization from acetone:MeOH (10:3), the title compound as yellow crystals in a 60% yield.

MP: 146° C.
Analysis for $C_{27}H_{22}N_2O_2 \cdot 0.4H_2O$:
Calculated: C,78.39; H,5.55; N,6.77;
Found: C,78.33; H,5.54; N,6.67%.

EXAMPLE 10
(E)-N-[4-[3-Oxo-3-(1-(4-nitrophenyl)-1.3,4,9-tetrahydro-β-carbolin-2-yl)progenyl]phenyl]acetamide The same method as employed in the preparation of Example 6 but starting from Intermediate 3 gave after recrystallization from 2-propanol, the title compound as white crystals in a 51% yield.

MP: 185° C.
Analysis for $C_{28}H_{24}N_4O_4 \cdot 0.6H_2O$:
Calculated: C,68.45; H,5.17; N,11.4;
Found: C,68.37; H,5.06; N,11.26%.

EXAMPLE 11
(E)-1-[1-(4-Nitrophenyl)-1,3,4,9-tetrahydro-β-carbolin-2-yl]-3-phenylpropene-1-one The same method as employed in the preparation of Example 1 but starting from Intermediate 3 gave after recrystallization from 2-propanol, the title compound as a yellow powder in a 15% yield.

MP: 205–206° C.
Analysis for $C_{26}H_{21}N_3O_3 \cdot 0.2H_2O$:
Calculated: C,73.12; H,5.05; N,9.84;
Found: C,72.95; H,5.15; N,9.81%.

EXAMPLE 12
(E)-1-[1-(4-Trifluoromethoxyphenyl)-1,3,4,9-tetrahydro-β-carbolin-2-yl]3-phenylpropene-1-one The same method as employed in the preparation of Example 1 but starting from Intermediate 4 gave after recrystallization from pentane, the title compound as white crystals in a 44% yield.

MP: 119° C.
Analysis for $C_{27}H_{21}N_2O_2F_3$:
Calculated: C,70.12; H,4.58; N,6.06;
Found: C,70.02; H,4.58; N,6.02%.

EXAMPLE 13
(E)-1-[1-(4-Methylphenyl)-1,3,4,9-tetrahydro-β-carbolin-2-yl]-3-phenylpropene-1-one The same method as employed in the preparation of Example 1 but starting from Intermediate 6 gave after recrystallization from pentane, the title compound as white crystals in a 50% yield.

MP: 125–127° C.
Analysis for $C_{27}H_{24}N_2O \cdot 0.6H_2O$:
Calculated: C,80.41; H,6.3; N,6.95;
Found: C,80.49; H,6.2; N,7.25%.

EXAMPLE 14
(E)-N-[4-[3-Oxo-3-(1-(3,4-methylenedioxyphenyl)-1,3,4,9-tetrahydro-β-carbolin-2-yl)-propenyl]phenyl]acetamide The same method as employed in the preparation of Example 6 but starting from Intermediate 7 and (E)-3-(4-acetylaminophenyl)acrylic acid gave after recrystallization from 2-propanol:pentane, the title compound as white crystals in a 85% yield.
MP: 185° C.
Analysis for $C_{29}H_{25}N_3O_4 \cdot 0.4H_2O$:
Calculated: C,71.56; H,5.34; N,8.63;
Found: C,71.59; H,5.32; 8.66%.

EXAMPLE 15

(E)-4-[3-Oxo-3-(1-Phenyl-1,3,4,9-tetrahydro-βcarbolin-2-yl)-Propenyl]benzoic Acid, Methyl Ester To a solution of Example 9 (0.2 g, 0.49 mmol) in 20 mL of MeOH was added activated $MnO_2$ (0.59 g, 14 equiv.), sodium cyanide (0.05 g, 2 equiv.) and acetic acid (0.05 g, 1.7 equiv.). The resulting mixture was stirred for 5 hours. Tlc monitoring showed a new compound ($SiO_2$,DCM:MeOH (95:5), Rf=0.82). The mixture was filtered through a short column of celite using 150 mL of a mixture of MeOH:EtOAc:$CHCl_3$ (1:25:25). After evaporation in vacuo the residue was purified via flash chromatography on a 2×20 cm² column using DCM as eluting solvent. Evaporation and recrystallization from EtOH gave the title compound (0.15 g, 70%) as yellow crystals.
MP: 222° C.
Analysis for $C_{28}H_{24}N_2O_3 \cdot 0.03H_2O$:
Calculated: C,76.1; H,5.61; N,6.34;
Found: C,76.05; H,5.68; N,6.15%.

EXAMPLE 16

(E)-1-[1-(2-Chlorophenyl)-1,3,4,9-tetrahydro-β-carbolin-2-yl]-3-phenylpropene-1-one The same method as employed in the preparation of Example 1 but starting from Intermediate 17 gave after recrystallization from EtOH, the title compound as white crystals in a 27% yield.
MP: 220–221° C.
Analysis for $C_{26}H_{21}N_2OCl$:
Calculated: C,75.63; H,5.13; N,6.78;
Found: C,75.4; H,5.21; N,6.79%.

EXAMPLE 17

(E)-1-(1-Phenyl-1,3,4,9-tetrahydro-β-carbolin-2-yl)-3-(3,4-methylenedioxyphenyl)-propene-1-one The same method as employed in the preparation of Example 1 but starting from (E)-(3,4-methylenedioxy)cinnamoyl chloride gave after recrystallization from EtOH, the title compound as a white powder in a 65% yield.
MP: 221° C.
Analysis for $C_{27}H22N_2O_3 \cdot 0.3H_2O$:
Calculated: C,75.79; H,5.32; N,6.55;
Found: C,75.76; H,5.37; N,6.53%.

EXAMPLE 18

(E)-1-[1-(3,4-Methylenedioxyphenyl)-1,3,4,9-tetrahydro-β-carbolin-2-yl]-3-(4-bromophenyl)propene-1-one The same method as employed in the preparation of Example 1 but starting from Intermediate 7 and (E)-4-bromocinnamoyl chloride gave after recrystallization from EtOH, the title compound as a white powder in a 10% yield.
MP: 188–190° C.
Analysis for $C_{27}H_{21}N_2O_3Br \cdot 0.3H_2O$:
Calculated: C,63.99; H,4.3; N,5.53;
Found: C,63.53; H,4.23; N,5.38%.

EXAMPLE 19

(E)-1-[1-(4-Chlorophenyl)-1,3,4,9-tetrahydro-β-carbolin-2-yl]-3-phenylpropene-1-one The same method as employed in the preparation of Example 1 but starting from Intermediate 5 gave after recrystallization from EtOH, the title compound as white crystals in a 72% yield.
MP: 213–214° C.
Analysis for $C_{26}H_{21}N_2OCl$:
Calculated: C,75.63; H,5.13; N,6.78;
Found: C,75.55; H,5.16; N,6.63%

EXAMPLE 20

(E)-1-[1-(3,4-Methylenedioxyphenyl)-1,3,4,9-tetrahydro-β-carbolin-2-yl]-3-(4-ethoxyphenyl)propene-1-one To a solution of Intermediate 7 (0.2 g,0.68 mmol) in 40 mL of DCM were added $Et_3N$ (0.1 mL, 1.1 equiv.), EDCl (0.14 g, 1.1 equiv.), HOBT (0.12 g, 1.1 equiv.) and (E)-4-ethoxycinnamic acid (0.14 g, 1.1 equiv.). After 48 hours of stirring at rt the reaction was judged to be completed by tlc monitoring ($SiO_2$, DCM:MeOH (95:5)) and was quenched with 50 mL of water. The reaction mixture was extracted with DCM, washed with brine (5 mL), dried over $MgSO_4$ and concentrated in vacuo. Flash chromatography on a 2.5×25 cm² column of silica gel using DCM:MeOH (98:2) as eluting solvent and removal of the solvent in vacuo gave the title compound (0.21 g, 67%) as white crystals after recrystallization from EtOH.
MP: 199–200° C.
Analysis for $C_{29}H_{26}N_2O_4 \cdot 0.3H_2O$:
Calculated: C,73.8; H,5.68; N,5.94;
Found: C,73.72; H,5.68; N,5.97%.

EXAMPLE 21

(E)-4-[3-Oxo-3-(1-(3,4-methylenedioxyphenyl)-1,3,4,9-tetrahydro-β-carbolin-2-yl)propenyl]acetic Acid, Phenyl Ester The same method as employed in the preparation of Example 20 but starting from (E)-4-acetoxycinnamic acid gave after recrystallization from MeOH, the title compound as white crystals in a 54% yield.
MP: 216° C.
Analysis for $C_{29}H_{24}N_2O_5$:
Calculated: C,72.49; H,5.03; N,5.83;
Found: C,72,3; H,5.11; N,5.84%.

EXAMPLE 22

(E)-1-[1-(3,4-Methylenedioxyphenyl)-1,3,4,9-tetrahydro-β-carbolin-2-yl-3-(4-hydroxyphenyl)propene-1-one The same method as employed in the preparation of Example 20 but starting from (E)-4-hydroxycinnamic acid gave after recrystallization from EtOH:pentane the title compound as white crystals in a 57% yield.
MP: 175° C.
Analysis for $C_{27}H_{22}N_2O_4 \cdot 0.3H_2O$:
Calculated: C,73.06; H,5.13; N,6.31;
Found: C,73.14; H,5.36; N,6.44%.

EXAMPLE 23

(E)-1-[1-(3,4-Methylenedioxyyhenyl)-1,3,4,9-tetrahydro-β-carbolin-2-yl]-3-(4-formylphenyl)propene-1-one The same method as employed in the preparation of Example 20 but starting from (E)-4-formylcinnamic acid gave after recrystallization from MeOH the title compound as white crystals in a 100% yield.
MP: 208° C.
Analysis for $C_{28}H_{22}N_2O_4 \cdot 0.3H_2O$:
Calculated: C,73.77; H,5.00; N,6.15;
Found: C,73.77; H,4,96; N,6.05%.

EXAMPLE 24

(E)-1-[4-[3-Oxo-3-(1-(3,4-methylenedioxyphenyl)-1,3,4,9-tetrahydro-β-carbolin-2-yl)-propenyl]phenyl]-3-phenylurea The same method as employed in the preparation of Example 20 but starting from (E)-3-[4-(3-(phenylureido)phenyl]acrylic acid (which was prepared in situ by reaction of phenylisocyanate (1 equiv.), (E)-4-aminocinnamic acid (1 equiv.) and Et₃N (1 equiv.)), gave after recrystallization from EtOH the title compound as white crystals in a 61% yield.
MP: 192° C.
Analysis for $C_{34}H_{28}N_4O_4$. 0.22(EtOH:H₂O):
Calculated: C,72.48; H,5.26; N,9.82;
Found: C,72.87; H,5.17; N,9.42%.

EXAMPLE 25
(E)-1-[1-(3,4-Methylenedioxyphenyl)-1,3,4,9-tetrahydro-β-carbolin-2-yl]-3-(4-aminophenyl)propene-1-one The same method as employed in the preparation of Example 20 but starting from (E)-4-aminocinnamic acid gave after recrystallization from EtOH:DCM:2-propanol (10:2:2) the title compound as white crystals in a 63% yield.
MP: 262–265° C.
Analysis for $C_{27}H_{23}N_3O_3$. 0.3H₂O:
Calculated: C,73.22; H,5.37; N,9.49;
Found: C,72.9; H,5.47; 9.32%.

EXAMPLE 26
(E)-1-[1-(3,4-Methylenedioxyphenyl)-1,3,4,9-tetrahydro-β-carbolin-2-yl]-3-(4-nitrophenyl)-propene-1-one The same method as employed in the preparation of Example 20 but starting from (E)-4-nitrocinnamic acid gave after recrystallization from EtOH, the title compound as yellow crystals in a 69% yield.
MP: 158° C.
Analysis for $C_{27}H_{21}N_3O_5$:
Calculated: C,69.37; H,4.53; N,8.99;
Found: C,69.57; H,4.61; N,8.92%.

EXAMPLE 27
(E)-1-[1-(3,4-Methylenedioxyphenyl)-1,3,4,9-tetrahydro-β-carbolin-2-yl]-3-1(4-bis(methylsulfonyl)aminophenyl]propene-1-one This product was prepared by refluxing for two hours a solution of Example 25 (0.2 g, 0.6 mmol), mesyl chloride (0.1 mL, 5 equiv.), Et₃N (0.4 mL, 5 equiv.) in 20 mL of THF. The disappearance of the starting material and the formation of a new compound were confirmed by tlc (SiO₂, DCM:MeOH (95:5), Rf=0.84). After evaporation of THF the residue was dissolved in DCM (15 mL) and washed with H₂O (10 mL). The organic solution was dried over MgSO₄ and concentrated in vacuo to give a residue which was purified via flash chromatography on a 2.5×25 cm² column using DCM:MeOH (98:2) as eluting solvent. Recrystallization from EtOH gave the title compound (0.09 g, 25%) as a white powder.
MP: 276° C.
Analysis for $C_{29}H_{27}N_3O_7S_2$. 0.3H₂O:
Calculated: C,58.14; H,4.64; N,7.01;
Found: C,57.76; H,4.69; N,6.81%.

EXAMPLE 28
(E)-4-(3-Oxo-3-[1-(3,4-methylenedioxyphenyl)-1,3,4,9-tetrahydro-β-carbolin-2-yl1-propenyl]benzoic Acid, Methyl Ester The same method as employed in the preparation of Example 20 but starting from (E)-4-(2-carboxyvinyl) benzoic acid, methyl ester acid (prepared according to the procedure of Taylor, E. C.; Young, W. B.; Chaudhari, R.; Patel, H. *Heterocycles* 1993, 36, 1897–1908), gave after recrystallization from MeOH:H₂O (99:1), the title compound as yellow crystals in a 84% yield.
MP: 211° C.
Analysis for $C_{29}H_{24}N_2O_5$. 0.3H₂O:
Calculated: C,71.68; H,5.1; N,5.76;
Found: C,71.76; H,5.02; N,5.68%.

EXAMPLE 29
(E)-N-[4-[3-Oxo-3-[1-(3,4-methylenedioxyphenyl)-1,3,4,9-tetrahydro-β-carbolin-2-yl]propenyl]phenyl]methanesulfonamide The same method as employed in the preparation of Example 27 but using 1 equiv. of mesyl chloride gave after recrystallization from EtOH the title compound as an off-white powder in a 10% yield.
MP: 203° C.
Analysis for $C_{28}H_{25}N_3O_5S$. 0.2H₂O:
Calculated: C,64.78; H,4,93N,8.09;
Found: C,64.66; H,5.15; N,7.73%.

EXAMPLE 30
(E)-4-[3-Oxo-3-[1-(3,4-methylenedioxyphenyl)-1,3,4,9-tetrahydro-β-carbolin-2-yl]propenyl]benzamide Into a solution of Example 28 (0.2 g, 0.4 mmol) in 50 mL of MeOH was bubbled ammonia and the resulting mixture was stirred at 35° C. for two days. The mixture was concentrated in vacuo to give a residue which was washed with 2×30 mL of water. Extraction, drying over MgSO₄ and concentration in vacuo gave a residue that was purified via radial chromatography using DCM:MeOH (90:10) as eluting solvent and via preparative chromatography (20×20-cm plate, 0.5 mm, SiO₂) using the same eluant. The title compound (0.025 g, 13%) was isolated as white crystals after recrystallization from MeOH:H₂O.
MP: 183° C.
Analysis for $C_{28}H_{23}N_3O_4$:
Calculated: C,70.07; H,5.17; N,8.76;
Found: C,69.97; H,5.16; N,8.84%.

EXAMPLE 31
(E)-4-[3-Oxo-3-[1-(3,4-methylenedioxyphenyl)-1,3,4,9-tetrahydro-β-carbolin-2-yl]-propenyl]benzoic Acid This product was prepared by refluxing for four hours a stirred solution of Example 28 (0.5 g, 1.04 mmol) and NaOH (1N) (5.2 mL, 5 equiv.) in 50 mL of MeOH. After evaporation of the solvent in vacuo, the residue was treated with 10 mL of HCl (1N). A solid precipitated out and was filtered off. Recrystallization from MeOH gave the title compound (0.35 g, 72%) as white crystals.
MP: 254–256° C.
Analysis for $C_{28}H_{22}N_2O_5$. 0.2H₂O:
Calculated: C,72.09; H,4.75; N,6.01;
Found: C,71.60; H,4.84; N,5.88%.

EXAMPLE 32
(E)-1-[1-(3,4-Methylenedioxyphenyl)-1,3,4,9-tetrahydro-β-carbolin-2-yl]-3-(4-cyanophenyl)propene-1-one The same method as employed in the preparation of Example 20 but starting from (E)-4-cyanocinnamic acid gave after recrystallization from EtOH the title compound as white crystals in a 69% yield.
MP: 167° C.
Analysis for $C_{28}H_2$, $N_3O_3$. 0.1H₂O:
Calculated: C,74.85; H,4.76; N,9.35;
Found:: C,74.72; H,4.81; N,9.27%.

EXAMPLE 33
(E)-1-[1-(3,4-Methylenedioxyphenyl)-1,3,4,9-tetrahydro-β-carbolin-2-yl]-3-(4-trifluoromethylphenyl)propene-1-one The same method as employed in the preparation of Example 20 but starting from (E)-4-trifluoromethylcinnamic acid gave after recrystallization from EtOH the title compound as white crystals in a 73% yield.
MP: 233° C.
Analysis for $C_{28}H_{21}F_3N_2O_3$. 0.2H₂O:
Calculated: C,68.07; H,4.37; N,5.67;
Found: C,68.04; H,4.32; N,5.65%.

EXAMPLE 34

(E)-1-[1-(3,4-Methylenedioxyphenyl)-1,3,4,9-tetrahydro-β-carbolin-2-yl]-3-(3,4-methylenedioxyphenyl)propene-1-one The same method as employed in the preparation of Example 20 but starting from (E)-3,4-methylenedioxycinnamic acid gave after recrystallization from EtOH the title compound as yellow crystals in a 73% yield.

MP: 233° C.
Analysis for $C_{28}H_{22}N_2O_5$:
Calculated: C,72.09; H,4.75; N,6.01;
Found: C,71.79; H,4.76; N,5.93%.

EXAMPLE 35

(E)-1-[1-(3,4-Methylenedioxyphenyl)-1,3,4,9-tetrahydro-β-carbolin-2-yl]-3-(4-chlorophenyl)propene-1-one The same method as employed in the preparation of Example 20 but starting from (E)-4-chlorocinnamic acid gave after recrystallization from EtOH the title compound as white crystals in a 55% yield.

MP: 203° C.
Analysis for $C_{27}H_{21}N_2O_3Cl$:
Calculated: C,70.97; H,4.63; N,6.13;
Found: C,71.04; H,4.76; N,6.04%.

EXAMPLE 36

(E)-1-[1-(3,4-Methylenedioxyphenyl)-1,3,4,9-tetrahydro-β-carbolin-2-yl]-3-(4-trifluoromethoxyphenyl)propene-1-one The same method as employed in the preparation of Example 20 but starting from (E)-4-trifluoromethoxycinnamic acid (prepared according to the procedure of Yagupol'skii, L. M., Troitskaya, V. I. *Zhurnal Obshchei Khimii* 1960, 30, 3102–3104) gave after recrystallization from EtOH the title compound as yellow crystals in a 35% yield.

MP: 203–205° C.
Analysis for $C_{28}H_{21}F_3N_2O_4$:
Calculated: C,66.4; H,4.18; N,5.53;
Found: C,66.23; H,4.26; N,5.54.

EXAMPLE 37

(E)-1-[1-(3,4-Methylenedioxyphenyl)-1,3,4,9-tetrahydro-β-carbolin-2-yl]-3-(4-methylphenyl)propene-1-one The same method as employed in the preparation of Example 20 but starting from (E)-4-methylcinnamic acid gave after recrystallization from EtOH:DCM (99:1) the title compound as white crystals in a 67% yield.

MP: 240° C.
Analysis for $C_{28}H_{24}N_2O_3$. $0.7H_2O$:
Calculated: C,74.88; H,5.7; N,6.24;
Found: C,74.83; H,5.45; N,6.35.%.

EXAMPLE 38

(E)-[4-[3-Oxo-3-(1-(3,4-methylenedioxyphenyl)-1,3,4,9-tetrahydro-β-carbolin-2-yl)propenyl]phenyl]urea The same method as employed in the preparation of Example 20 but starting from Intermediate 22 gave after recrystallization from EtOH the title compound as white crystals in a 49% yield.

MP: 208° C.
Analysis for $C_{28}H_{24}N_4O_4$. $0.5H_2O$:
Calculated: C,68.7; H,5.15; N,11.44;
Found: C,68.51; H,5.14; N,11.35%.

EXAMPLE 39

(E)-1-[1-(3,4-Methylenedioxyphenyl)-1,3,4,9-tetrahydro-β-carbolin-2-yl]-3-(4-hydroxymethylphenyl)propene-1-one This product was prepared by stirring a solution of Example 23 (0.3 g, 0.66 mmol) in 40 mL of MeOH with $NaBH_4$ (0.1 g, 4 equiv.) at rt for two hours. Evaporation of the solvent gave a residue which was dissolved in DCM (100 mL) and washed twice with water (50 mL). Extraction with DCM, drying over $MgSO_4$ and evaporation in vacuo gave the title compound (0.2 g, 67%) as white crystals after recrystallization from EtOH.

MP: 206° C.
Analysis for $C_{28}H_{24}N_2O_4$. 0.3EtOH:
Calculated: C,73.66; H,5.58; N,6.01;
Found: C,73.69; H,5.5; N,6.06%.

EXAMPLE 40

(E)-N-Benzyl4-[3-oxo-3-(1-(3,4-methylenedioxyrhenyl)-1,3,4,9-tetrahydro-β-carbolin-2-yl)propenyl]benzamide This product was prepared by stirring a solution of Example 31 (0.2 g, 0.43 mmol) in 50 mL of THF with benzylamine (0.5 mL, 9 equiv.), $Et_3N$ (1 mL) and diphenylphosphoryl azide (0.5 mL). After two days the reaction mixture was concentrated in vacuo. The residue was taken up in 100 mL of DCM and washed with 3×50 mL of water. Drying over $Na_2SO_4$ and evaporation of the solvent gave a residue which was purified via flash chromatography with cyclohexane and $Et_2O$. Evaporation in vacuo and recrystallization from EtOH gave the title compound (0.03 g, 13%) as white crystals.

MP: 203° C.
Analysis for $C_{35}H_{29}N_3O_4$:
Calculated: C,75.66; H,5.26; N.7.56;
Found: C,75.5; H,5.22; N,7.55%.

EXAMPLE 41

(E)-1-[1-(3,4-Methylenedioxyphenyl)-1,3,4,9-tetrahydro-β-carbolin-2-yl]-3-(2,4-dichlorophenyl)propene-1-one The same method as employed in the preparation of Example 20 but starting from (E)-2,4-dichlorocinnamic acid gave after recrystallization from EtOH:$H_2O$ the title compound as a white powder in a 66% yield.

MP: 194° C.
Analysis for $C_{27}H_{20}N_2O_3Cl_2$:
Calculated: C,66.00; H,4.10; N,5.70;
Found: C,65.85; H,4.13; N,5.78%.

EXAMPLE 42

(E)-1-[1-(3,4-Methylenedioxyphenyl)-1,3,4,9-tetrahydro-β-carbolin-2-yl]-3-(3-methoxy-4-hydroxyphenyl)propene-1-one The same method as employed in the preparation of Example 20 but starting from (E)-3-methoxy4-hydroxycinnamic acid gave after recrystallization from EtOH:H20 (10:1) the title compound as an off-white powder in a 62% yield.

MP: 155° C.
Analysis for $C_{28}H_{24}N_2O_5$:
Calculated: C,71.78; H,5.16; N,5.98;
Found: C,71.44; H,5.16; N,5.76%.

EXAMPLE 43

(E)-1-[1-(3,4-Methylenedioxyyhenyl)-1,3,4,9-tetrahydro-β-carbolin-2-yl]-3-(3-hydroxy-4-methoxyphenyl)propene-1-one The same method as employed in the preparation of Example 20 but starting from (E)-3-hydroxy-4-methoxycinnamic acid gave after recrystallization from EtOH:$H_2O$ the title compound as an off-white powder in a 47% yield.

MP: 213° C.
Analysis for $C_{28}H_{24}N_2O_5$. $0.3H_2O$:
Calculated: C,70.96; H,5.23N,5.91;
Found: C,71.09; H,5.60; N,5.66%.

EXAMPLE 44
(E)-1-[1-(3,4-Methylenedioxyphenyl)-1,3,4,9-tetrahydro-β-carbolin-2-yl]-3-(4-fluorophenyl)propene-1-one The same method as employed in the preparation of Example 20 but starting from (E)-4-fluorocinnamic acid gave after recrystallization from EtOH the title compound as white crystals in a 74% yield.
MP: 138–139° C.
Analysis for $C_{27}H_{21}F_3N_2O_3$:
Calculated: C,73.62; H,4.81; N,6.36;
Found: C,73.78; H,4.81; N,5.97%.

EXAMPLE 45
(E)-1-[1-(3,4-Methylenedioxyphenyl)-1,3,4,9-tetrahydro-β-carbolin-2-yl]-3-indan-5-yl-1-propene-1-one The same method as employed in the preparation of Example 20 but starting from (E)-3-indane-5-ylacrylic acid gave, after precipitation, the title compound as a yellow powder in a 22% yield.
MP: 115° C.
Analysis for $C_{20}H_{26}N_2O_3 \cdot 0.6H_2O$:
Calculated: C,76.12; H,5.79; N,5.92;
Found: C,76.13; H,5.79; N,5.72%.

EXAMPLE 46
(E)-N-[4-[3-Oxo-3-(1-(3,4-methylenedioxyphenyl)-1,3,4,9-tetrahydro-β-carbolin-2-yl)propenyl]benzoyl]benzenesulfonamide The same method as employed in the preparation of Example 20 but starting from Example 31 and benzenesulfonamide gave after recrystallization from EtOH:H$_2$O the title compound as white crytals in a 20% yield.
MP: 134° C.
Analysis for $C_{20}H_{26}N_2O_3 \cdot 0.6H_2O$:
Calculated: C,56.13; H,6.67; N,10.91;
Found: C,55.97; H,6.75; N,10.82%.

EXAMPLE 47
(E)-1-[1-(3,4-Methylenedioxyphenyl)-1,3,4,9-tetrahydro-β-carbolin-2-yl]-3-(3,4-dichlorophenyl)propene-1-one The same method as employed in the preparation of Example 20 but starting from (E)-3,4-dichlorocinnamic acid gave after recrystallization from EtOH:H$_2$O (99:1) the title compound as a white powder in a 45% yield.
MP: 212° C.
Analysis for $C_{27}H_{20}Cl_2N_2O_3$:
Calculated: : C,66.00; H,4.10; N,5.70;
Found: C,65.68; H,4.12; N, 5.68%.

EXAMPLE 48
(E)-1-[1-(3,4-Methylenedioxyphenyl)-1,3,4,9-tetrahydro-β-carbolin-2-yl]-3-(3,4-dimethoxyphenyl)propene-1-one The same method as employed in the preparation of Example 20 but starting from (E)-3,4-dimethoxycinnamic acid gave after recrystallization from EtOH:DCM the title compound as a white powder in a 61% yield.
MP: 233° C.
Analysis for $C_{29}H_{26}N_2O_5 \cdot 0.5H_2O$:
Calculated: C,70.86; H,5.54; N,5.70;
Found: C,70.66; H,5.44; N,5.70%.

EXAMPLE 49
(E)-1-[1-(3,4-Methylenedioxyphenyl)-1,3,4,9-tetrahydro-β-carbolin-2-yl-3-(3,4-dihydroxyphenyl)propene-1-one The same method as employed in the preparation of Example 20 but starting from (E)-3,4-dihydroxycinnamic acid gave after recrystallization from EtOH:DMF the title compound as a white powder in a 41% yield.
MP: 163–165° C.
Analysis for $C_{27}H_{22}N_2O_5 \cdot 0.3DMF$:
Calculated: C,70.34; H,5.10; N,6.76;
Found: C,70.38; H,5.13; N,6.66%.

EXAMPLE 50
(E)-N-Methyl-N-[4-(3-oxo-3-(1-(3,4-methylenedioxyphenyl)-1,3,4,9-tetrahydro-β-carbolin-2-yl)propenyl]phenyl]acetamide The same method as employed in the preparation of Example 20 but starting from Intermediate 23 gave after recrystallization from EtOH:H$_2$O (10:0.6) the title compound as an off-white powder in a 86% yield EtOH:H$_2$O.
MP: 165° C.
Analysis for $C30H_{27}N_3O_4 \cdot 0.4H_2O$:
Calculated: C,71.96; H,5.6; N,8.39;
Found: C,71.8; H,5.57; N,8.28%.

EXAMPLE 51
(E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide This product was prepared by condensation of Example 25 (0.2 g, 0.46 mmol) with 2,2-dimethylpropionyl chloride (0.09 mL, 1.5 equiv.) and NaOH (1N) (0.7 mL, 1.5 equiv.) in a mixture of EtOAc:DCM (6:1). When starting material had disappeared, 40 mL of a mixture of DCM:H$_2$O (2:1) was added. Extraction with DCM, washing with a saturated aqueous solution of NH$_4$Cl and brine, drying over MgSO$_4$ and evaporation of the solvent in vacuo gave the title compound (0.2 g, 83%) after recrystallization from EtOH:H$_2$O (1:1).
MP: 172–174° C.
Analysis for $C_{32}H_{31}N_3O_4 \cdot 0.1H_2O$:
Calculated: C,71.23; H,6.16; N,7.79;
Found: C,70.99; H,6.02; N,7.84%.

EXAMPLE 52
(E)-1-[1-(3,4-Methylenedioxyphenyl)-1,3,4,9-tetrahydro-β-carbolin-2-yl1]-3-(3,5-dimethoxyphenyl)propene-1-one The same method as employed in the preparation of Example 20 but starting from (E)-3,5-dimethoxycinnamic acid gave after recrystallization from EtOH the title compound as a white powder in a 61% yield.
MP; 178° C.
Analysis for $C_{29}H_{26}N_2O_5$:
Calculated: C,72.19; H,5.43; N,5.81;
Found: C,72.3; H,5.48; N,5.63%.

EXAMPLE 53
(E)-(N)-{4-[3-[1-(3,4-Methylenedioxyphenyl)6-fluoro-1,3,4,9-tetrahydro-β-carbolin-2-yl]-3-oxopropenyl]phenyl}-acetamide The same method as employed in the preparation of Example 20 but starting from Intermediate 16 and and (E)-3-(4-acetylaminophenyl)acrylic acid gave after recrystallization from MeOH the title compound as a white crystals in a 72% yield.
MP:179–181° C.
Analysis for $C_{29}H_{24}N_3O_4F \cdot 0.4H_2O$:
Calculated: C,69.01; H,4,95; N,8.33;
Found: C,68.97; H,4,91; N,8.34%.

EXAMPLE 54
(E)-1-[1-(3,4-Methylenedioxyphenyl)-1,3,4,9-tetrahydro-β-carbolin-2-yl]-3-(3,4,5-trimethoxyphenyl)propene-1-one The same method as employed in the preparation of Example 20 but starting from (E)-3,4,5-trimethoxycinnamic acid gave after recrystallization from MeOH the title compound as a white powder in a 49% yield.
MP: 211° C.
Analysis for $C_{30}H_{28}N_2O_6$:

Calculated: C,70.3; H,5.51; N,5.47;
Found: C,70.49; H,5.59; N,5.34.%.

EXAMPLE 55
(E)-N-[4-[3-Oxo-3-(1-(3,4-methylenedioxyphenyl)-1,3,4,9-tetrahydro-β-carbolin-2-yl)propenyl]phenyl]isobutyramide The same method as employed in the preparation of Example 51 but starting from isobutyryl chloride gave after recrystallization from EtOH the title compound as a white powder in a 85% yield.
MP: 171° C.
Analysis for $C_{31}H_{29}N_3O_4$. $0.4(H_2O:MeOH)$:
Calculated: C,72.61; H,6.02; N,7.99;
Found: C,72,33; H,5.77; N,8.33%.

EXAMPLE 56
(E)-1-[1-(3,4-Methylenedioxyphenyl)6-fluoro-1,3,4,9-tetrahydro-β-carbolin-2-yl]-3-phenylpropene-1-one The same method as employed in the preparation of Example 1 but starting from Intermediate 16 gave after recrystallization from EtOH the title compound as white crystals in a 71% yield.
MP: 227–228° C.
Analysis for $C_{27}H_{21}N_2O_3F$:
Calculated: C,73.63; H,4.81; N,6.36;
Found: C,73.72; H,4.77; N,6.43%.

EXAMPLE 57
(E)-N-(2-Methoxyethyl)-4-[3-oxo-3-(1-(3,4-Methylenedioxyphenyl)-1,3,4,9-tetrahydro-β-carbolin-2-yl)propenyl]benzamide The same method as employed in the preparation of Example 20 but starting from Intermediate 24 gave after recrystallization from EtOH the title compound as white crystals in a 43% yield.
MP: 170° C.
Analysis for $C_{27}H_{21}N_2O_3F$. $1.3H_2O$:
Calculated: C,68.07; H,5.82; N.7.68;
Found: C,67.98; H,5.8; N,7.7%.

EXAMPLE 58
(E)-1-[1-(3,4-Methylenedioxyphenyl)-1,3,4,9-tetrahydro-β-carbolin-2-yl]-3-(3-hydroxyphenyl)propene-1-one The same method as employed in the preparation of Example 20 but starting from (E)-3-hydroxycinnamic acid gave after recrystallization from EtOH:$H_2O$ the title compound as white crystals in a 54% yield.
MP: 248° C.
Analysis for $C_{27}H_{22}N_2O_4$:
Calculated: C,73.96; H,5.06; N,6.39;
Found: C,74.04; H,5.1; N,6.37%.

EXAMPLE 59
(E)-1-[1-(3,4-Methylenedioxyphenyl)-1,3,4,9-tetrahydro-β-carbolin-2-yl]-3-(3-methoxyphenyl)propene-1-one The same method as employed in the preparation of Example 20 but starting from (E)-3-methoxycinnamic acid gave after recrystallization from EtOH the title compound as white crystals in a 49% yield.
MP: 218° C.
Analysis for $C_{28}H_{24}N_2O_4$:
Calculated: C,74.32; H,5.35; N,6.19;
Found: C,74.37; H,5.61; N,6.32%.

EXAMPLE 60
(E)-1-[1-(3,4-Methylenedioxyphenyl)-1,3,4,9-tetrahydro-β-carbolin-2-yl]-3-(3-nitrophenyl)propene-1-one The same method as employed in the preparation of Example 20 but starting from (E)-3-nitrocinnamic acid gave after recrystallization from EtOH:$H_2O$ (20:1) the title compound as white crystals in a 91% yield.
MP: 156–158° C.
Analysis for $C_{28}H_{24}N_2O_4$:
Calculated: C,69.37; H,4.54; N,8.99;
Found: C,69.12; H,4.77; N,8.81%.

EXAMPLE 61
(E)-1-[1-(3,4-Methylenedioxyphenyl)-1,3,4,9-tetrahydro-β-carbolin-2-yl]-3-[4-(2-dimethylaminoethoxy)phenyl]propene-1-one The same method as employed in the preparation of Example 20 but starting from Intermediate 25 gave after recrystallization from EtOH:$H_2O$ the title compound as white crystals in a 45% yield.
MP: 157° C.
Analysis for $C_{31}H_{31}N_3O_4$:
Calculated: C,73.07; H,6.13; N,8.25;
Found: C,72.7; H,6.17; N,8.12%.

EXAMPLE 62
(E)-N-(2-Morpholin-4-ylethyl)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 26 gave after recrystallization from EtOH:$H_2O$ the title compound as white crystals in a 13% yield.
MP: 145° C.
Analysis for $C_{34}H_{34}N_4O_5$. $0.7H_2O$:
Calculated: C,69.07; H,6.03; N9.48;
Found: C,69.08; H, 6.03; N,9.45%.

EXAMPLE 63
(E)-1-[1-(3,4-Methylenedioxyphenyl)-1,3,4,9-tetrahydro-β-carbolin-2-yl]-3-[4-(1H-tetrazol-5-yl)phenyl]propene-1-one To a solution of Example 32 (0.25 g, 0.56 mmol) in 10 mL of toluene were added successively trimethylsilylazide (0.30 mL, 4 equiv.) and dibutyltinoxide (0.06 g, 0.4 equiv.). The resulting mixture was stirred at reflux for two days. T/c monitoring showed formation of a new compound (DCM:MeOH (80.20), Rf=0.35). The reaction mixture was concentrated in vacuo. The resulting yellow gum was dissolved in MeOH and concentrated in vacuo. The residue was partitioned between EtOAc (25 mL) and an aqueous saturated solution of $NaHCO_3$ (25 mL). The organic phase was extracted with an additional portion of an aqueous saturated solution of $NaHCO_3$ (25 mL). The combined aqueous extracts were acidified to pH=2 with HCl (1N) and then extracted with EtOAc (2×25 mL). The combined organic extracts were dried over $MgSO_4$, filtered and concentrated to give a yellow powder that was purified via flash chromatography ($SiO_2$, DCM:MeOH (90:10)). Recrystallization from 2-propanol:$iPr_2O$ (1:1) gave the title compound (0.19 g, 70%) as white crystals.
MP: 232–233° C.
Analysis for $C_{28}H_{22}N_6O_3$. $0.4H_2O$:
Calculated: C,67.02; H,4.92; N,16.28;
Found: C,66.83; H,4.53; N,15.96%.

EXAMPLE 64
(E)-1-[1-(3,4-Methylenedioxyphenyl)-1,3,4,9-tetrahydro-β-carbolin-2-yl]-3-(3-aminophenyl)propene-1-one A solution of Example 60 (1.36 g, 2.9 mmol), $SnCl_2.H_2O$ (2.8 g, 5 equiv.) in EtOH was refluxed overnight. After evaporation of the solvent, the residue was taken up in 50 mL of NaOH (1N). The aqueous phase was extracted with 2×100 mL of DCM and 2×50 mL of EtOAc. The combined organic layers were dried over $Na_2SO_4$ and concentrated in vacuo. Flash chromatography ($SiO_2$, DCM:MeOH (95:5) and recrystallization from EtOH:DCM gave the title compound (0.27 g, 21%) as a pale yellow powder.

MP: 139–141° C.
Analysis for $C_{27}H_{23}N_3O_3$:
Calculated: C,74.13; H,5.30; N,9.60;
Found: C,73.93; H,5.35; N,9.43%.

EXAMPLE 65

(E)-N-Cyclohexyl-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 27 gave after recrystallization from EtOH:H$_2$O the title compound as white crystals in a 6% yield.
MP: 214° C.
Analysis for $C_{28}H_{21}N_3O_3$. 0.1H$_2$O:
Calculated: C,72.19; H,6.24; N,7.43;
Found: C,72.28; H,6.19; N,6.93%.

EXAMPLE 66

(E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 28 gave after recrystallization from EtOH:H$_2$O (8:2) the title compound as white crystals in a 61% yield.
MP: 168° C.
Analysis for $C_{32}H_{29}N_3O_5$. 0.8H$_2$O:
Calculated: C,69.88; H,5.61; N,7.64;
Found: C,69.74; H,5.78; N,7.22%.

EXAMPLE 67

(E)-1-[1-(3,4-Methylenedioxyphenyl)-1,3,4,9-tetrahydro-β-carbolin-2-yl]-3-(3-cyanophenyl)propene-1-one The same method as employed in the preparation of Example 20 but starting from (E)-cyanocinnamic acid gave after recrystallization from EtOH:H$_2$O (8:2) the title compound as white crystals in a 46% yield.
MP: 228–230° C.
Analysis for $C_{28}H_{21}N_3O_3$. 0.8H$_2$O:
Calculated: C,72.81; H,4.93; N,9.10;
Found: C,72.74; H,4.69; N,8.99%.

EXAMPLE 68

(E)-N-(4-Piperidine-4-carboxylic Acid, Ethyl Ester)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 29 gave after recrystallization from iPr$_2$O the title compound as white crystals in a 28% yield.
MP: 144–145° C.
Analysis for $C_{36}H_{35}N_3O_6$. 0.7H$_2$O:
Calculated: C, 69.93; H,5.93; N,6.8;
Found: C,69.84; H,5.83; N,6.81%.

EXAMPLE 69

(E)-N-(4-Piperidine-4-carboxylic Acid)-4-[3-oxo-3-(1-(3,4-methylenedioxyphenyl)-1,3,4,9-tetrahydro-β-carbolin-2-yl)propenyl]benzamide This product was prepared by refluxing a solution of Example 68 (0.21 g, 0.36 mmol) with NaOH (1 N) (0.72 mL, 2 equiv.) in 20 mL of MeOH for 12 hours. After cooling the mixture was poured into H$_2$O (100 mL) and acidified with HCl (1 N). Extraction with 2×50 mL of DCM, drying over Na$_2$SO$_4$ and concentration in vacuo gave a residue which was recrystallized from MeOH:H$_2$O to give the title compound (0.05 g, 24%) as white crystals.
MP: 204–205° C.
Analysis for $C_{34}H_{31}N_3O_6$. 0.4H$_2$O:
Calculated: C,68.56; H,5.58; N,7.05;
Found: C,68.58; H,5.12; N,7.06%.

EXAMPLE 70

(E)-3-[3-Oxo-3-[1-(3,4-methylenedioxyphenyl)-1,3,4,9-tetrahydro-β-carbolin-2-yl]-propenyl]benzoic Acid The same method as employed in the preparation of Example 20 but starting from (E)-3-(2-carboxyvinyl)benzoic acid gave after recrystallization from MeOH, the title compound as a white powder in a 21% yield.
MP: 156–158° C.
Analysis for $C_{28}H_{22}N_2O_5$. 0.8H$_2$O:
Calculated: C,69.93; H,4.95; N,5.83;
Found: C,69.94; H,4.62; N,5.65%.

EXAMPLE 71

(E)-1-[1-(3,4-Methylenedioxyphenyl)-1,3,4,9-tetrahydro-β-carbolin-2-yl]-3-3-(4-methylpiperazine-1-carbonyl)phenyl)propene-1-one The same method as employed in the preparation of Example 20 but starting from Example 70 and 4-methylpiperazine gave after recrystallization from MeOH:H$_2$O, the title compound as a white powder in a 30% yield.
MP: 151° C.
Analysis for $C_{33}H_{32}N_4O_4$. H$_2$O:
Calculated: C,69.95; H,6.05; N,9.89;
Found: C,69.63; H,5.93; N,9.99%.

EXAMPLE 72

(E)-N-(2-Piperazin-1-ylethyl)-3-[3-oxo-3-(1-(3,4-methylenedioxyphenyl)-1,3,4,9-tetrahydro-β-carbolin-2-yl)propenyl]benzamide The same method as employed in the preparation of Example 20 but starting from Example 70 and 1-(2-aminoethyl)piperazine gave after recrystallization from iPr$_2$O, the title compound as a white powder in a 23% yield.
MP: 138–140° C.
Analysis for $C_{34}H_{35}N_5O_4$. 3.1H$_2$O:
Calculated: C,64.46; H,6.55; N,11.05;
Found: C,64.46; H,6.25; N,11.00%.

EXAMPLE 73

(E)4-[3-Oxo-3-(1-(3,4-methylenedioxyphenyl)-1,3,4,9-tetrahydro-β-carbolin-2-yl)-propenyl]acetic Acid Ethyl Ester The same method as employed in the preparation of Example 20 but starting from Intermediate 30 gave after recrystallization from DCM:pentane, the title compound as a white powder in a 17% yield.
MP: 92–95° C.
Analysis for $C_{31}H_{28}N_2O_5$. 0.9H$_2$O:
Calculated: C,70.95; H,5.72; N,5.34;
Found: C,71.32; H,6.0; N,4.93%.

EXAMPLE 74

(E)-1-[1-(3,4-Methylenedioxyphenyl)-1,3,4,9-tetrahydro-β-carbolin-2-yl]-3-(3-tetrazolophenyl)propene-1-one The same method as employed in the preparation of Example 63 but starting from Example 67 gave after recrystallization from MeOH:H$_2$O, the title compound as a white powder in a 5% yield.
MP: 260–264° C.
Analysis for $C_{28}H_{22}N_6O_3$. 2.2H$_2$O:
Calculated: C,63.43; H,5.02; N,15.85;
Found: C,63.31; H,4.37; N,15.47%.

EXAMPLE 75
(E)-2-[3-Oxo-3-[1-(3,4-methylenedioxyphenyl)-1,3,4,9-tetrahydro-β-carbolin-2-yl]-propenyl]benzoicacid, Methyl Ester The same method as employed in the preparation of Example 20 but starting from (E)-2-(2-carboxyvinyl)benzoic acid, methyl ester (prepared according to the procedure of Alabaster, R. J.; Cottrell, I. F.; Hands, D.; Humphrey, G. R.; Kennedy, D. J.; Wright, S. H. B. *Synthesis* 1989, 8, 598–603), gave after recrystallization from MeOH, the title compound as white crystals in a 46% yield.
MP: 203–204° C.
Analysis for $C_{27}H_{21}N_3O_5$:
Calculated: C,72.49; H,5.03; N,5.83;
Found: C,72.59; H,5.1; N,5.67%.

EXAMPLE 76
(E)-3-[3-Oxo-3-[1-(3,4-methylenedioxyphenyl)-1,3,4,9-tetrahydro-β-carbolin-2-yl]-propenyl]benzoic Acid, Methyl Ester The same method as employed in the preparation of Example 20 but starting from (E)-3-(2-carboxyvinyl)benzoicacid, methyl ester (prepared according to the procedure of Baker, S. R.; Jamieson, W. B.; Todd, A. EP 134111 A1), gave after recrystallization from MeOH, the title compound as yellow crystals in a 61% yield.
MP: 165–167° C.
Analysis for $C_{29}H_{24}N_2O_5$:
Calculated: C,72.49; H,5.03; N,5.83;
Found: C,72.53; H,5.02; N,5.93%.

EXAMPLE 77
(E)-1-(4-[3-Oxo-3-(1-(3,4-methylenedioxyphenyl)-1,3,4,9-tetrahydro-β-carbolin-2-yl)-propenyl]phenyl)piperidine-4carboxylic Acid, Ethyl Ester The same method as employed in the preparation of Example 20 but starting from Intermediate 31 gave after recrystallization from MeOH, the title compound as yellow crystals in a 45% yield.
MP: 175° C.
Analysis for $C_{35}H_{35}N_3O_5$:
Calculated: C,72.77; H,6.11; N,7.27;
Found: C,72.99; H,6.16; N,7.03%.

EXAMPLE 78
(E)-N-(1-Ethylpyrrolidin-2-yl-methyl)-3-[3-oxo-3-(1-(3,4-methylenedioxyphenyl)-1,3,4,9-tetrahydro-β-carbolin-2-yl)propenyl]benzamide The same method as employed in the preparation of Example 20 but starting from Example 70 and 2-pyrrolidin-1-ylethylamine gave after recrystallization from iPr₂O, the title compound as a white powder in a 53% yield.
MP: 128–130° C.
Analysis for $C_{35}H_{36}N_4O_4$:
Calculated: C,72.9; H,6.29; N,9.72;
Found: C,72.9; H,6.42; N,10.01%.

EXAMPLE 79
(E)-1-[1-(3,4-Methylenedioxyphenyl)-1,3,4,9-tetrahydro-β-carbolin-2-yl]-3-(3-(2-dimethylaminoethoxy)phenyl)propene-1-one To a solution of Example 58 (0.25 g, 0.57 mmol) in 50 mL of DMF was added $K_2CO_3$ (0.24 g, 3 equiv.) and an excess of dimethylaminodiethyl chloride (about 15 equiv.). The resulting mixture was heated at 60° C. for four hours until disappearance of the Jstarting material (tlc monitoring, DCM:MeOH (90:10). A new compound was formed (Rf= 0.20). After evaporation of DMF, the residue was taken up in 150 mL of DCM, washed with 2×50 mL of water, dried over $Na_2SO_4$ and recrystallized from EtOH:H₂O to give the title compound (0.06 g, 22%) as yellow crystals.
MP: 76–78° C.
Analysis for $C_{31}H_{31}N_3O_4$. 0.6H₂O:
Calculated: C,71.55; H,6.24; N,8.07;
Found: C,71.34; H,6.45; N,7.8%.

EXAMPLE 80
(E)-1-[1-(3,4-Methylenedioxyphenyl)-1,3,4,9-tetrahydro-β-carbolin-2-yl]-3-(3,5-diterbutyl-4-hydroxyphenyl)propene-1-one The same method as employed in the preparation of Example 20 but starting from (E)-3,5-ditertbutyl-4-hydroxycinnamic acid gave after recrystallization from cyclohexane, the title compound as yellow crystals in a 45% yield.
MP: 137° C.

EXAMPLE 81
(E)-3-[3-Oxo-3-[1-(4-methoxycarbonylphenyl)-1,3,4,9-tetrahydro-β-carbolin-2-yl]propenyl]benzoic Acid, Methyl Ester The same method as employed in the preparation of Example 20 but starting from Intermediate 8 and (E)-3-(2-carboxy-vinyl)benzoic acid, methyl ester (prepared according to the procedure of Baker, S. R.; Jamieson, W. B; Todd, A. EP 134111 A1), gave after recrystallization from 2-propanol, the title compound as white crystals in a 70% yield.
MP: 182° C.
Analysis for $C_{30}H_{26}N_2O_5$:
Calculated: C,72.86; H,5.3; N,5.66;
Found: C,72.49; H,5.31; N,5.68%.

EXAMPLE 82
(E)-2-[3-Oxo-3-[1-(3,4-methylenedioxyphenyl)-1,3,4,9-tetrahydro-β-carbolin-2-yl]-propenyl]benzoic Acid The same method as employed in the preparation of Example 31 but starting from Example 75 gave after recrystallization from MeOH the title compound as off-white crystals in a 78% yield.
MP: 174° C.
Analysis for $C_{28}H_{22}N_2O_5$:
Calculated: C,72.09, H,4.75; N,6.01;
Found: C,72.53; H,4.72; N,5.76%.

EXAMPLE 83
(E)-(4-[3-Oxo-3-(1-(3,4-methylenedioxyphenyl)-1,3,4,9-tetrahydro-β-carbolin-2-yl)propenyl]phenoxy)acetic Acid, Ethyl Ester The same method as employed in the preparation of Example 79 but starting from Example 22 and bromoacetic acid, ethyl ester, gave after recrystallization from EtOH:2-propanol the title compound as yellow crystals in a 28% yield.
MP: 99–98° C.
Analysis for $C_{31}H_{28}N_2O_6$. 2.4H₂O:
Calculated: C,65.57; H,5.82; N,4.93;
Found: C,65.34; H,5.4; N,5.09%.

EXAMPLE 84
(E)-(4-[3-Oxo-3-(1-(3,4-methylenedioxyphenyl)-1,3,4,9-tetrahydro-β-carbolin-2-yl)-propenyl]phenyl)acetic Acid The same method as employed in the preparation of Example 31 but starting from a solution of Example 73 in EtOH gave after recrystallization from iPr₂O:2-propanol the title compound as white crystals in a 51% yield.
MP: 231° C.
Analysis for $C_{29}H_{24}N_2O_5$. 0.25iPrOH:
Calculated: C, 72.11; H, 5.29; N,5.64;
Found: C, 71.9; H, 5.15; N, 5.74%.

EXAMPLE 85
(E)-(4-[3-Oxo-3-(1-(3,4-methylenedioxyphenyl)-1,3,4,9-tetrahydro-β-carbolin-2-yl)propenyl]phenoxy)acetic Acid The same method as employed in the preparation of Example 31 but starting from Example 83 gave after recrystallization from iPr$_2$O:2-propanol the title compound as yellow crystals in a 45% yield.

MP: 158–160° C.

Analysis for $C_{29}H_{24}N_2O_6$. $0.9H_2O$:
Calculated: C,67.93; H,5.07; N,5.46;
Found: C,68.0; H,4.86; N,5.21%.

EXAMPLE 86
(E)-1-[1-(3,4-Methylenedioxyphenyl)-1,3,4,9-tetrahydro-β-carbolin-2-yl]-3-(3-nitro-4-chlorophenyl)propene-1-one The same method as employed in the preparation of Example 20 but starting from (E)-3-nitro-4-chlorocinnamic acid gave after recrystallization from EtOH the title compound as yellow crystals in a 56% yield.

MP: 240° C.

Analysis for $C_{27}H_{20}N_3O_5Cl$:
Calculated: C,64.61; H,4.02; N,8.37;
Found: C,64.5; H,3.97; N,8.28%.

EXAMPLE 87
(E)-1-[1-(3,4-Methylenedioxyphenyl)-1,3,4,9-tetrahydro-β-carbolin-2-yl]-3-(5-nitro-2-chlorophenyl)propene-1-one The same method as employed in the preparation of Example 20 but starting from (E)-5-nitro-2-chlorocinnamic acid gave after recrystallization from EtOH:H$_2$O the title compound as yellow crystals in a 44% yield.

MP: 146° C.

Analysis for $C_{27}H_{20}N_3O_5Cl$. $0.1H_2O$:
Calculated: C,64.38; H,4.04; N,8.34;
Found: C,64.12; H,3.81; N,8.35%.

EXAMPLE 88
(E)-3-Chloro-4-[3-oxo-3-[1-(3,4-methylenedioxyphenyl)-1,3,4,9-tetrahydro-β-carbolin-2-yl]propenyl]benzoic Acid, Methyl Ester The same method as employed in the preparation of Example 20 but starting from Intermediate 32 gave after recrystallization from EtOH the title compound as a white powder in a 57% yield.

MP: 166° C.

Analysis for $C_{29}H_{23}N_2O_5Cl$. $0.15EtOH$:
Calculated: C,67.43; H,4.62; N,5.37;
Found: C,67.09; H,4.56; N,5.51%.

EXAMPLE 89
(E)-(4-[3-Oxo-3-(1-(3,4-methylenedioxyphenyl)-1,3,4,9-tetrahydro-β-carbolin-2-yl)propenyl]benzyloxy)acetic Acid The same method as employed in the preparation of Example 79 but starting from a solution of (E)-(4-[3-oxo-3-(1-(3,4-methylenedioxyphenyl)-1,3,4,9-tetrahydro-β-carbolin-2-yl)propenyl]benzyloxy acetic acid, ethyl ester in EtOH gave after recrystallization from MeOH:H$_2$O the title compound as an off-white solid in a 40% yield.

MP: 162–163° C.

Analysis for $C_{30}H_{26}N_2O_6$. $0.1H_2O$:
Calculated: C,68.17; H,5.13; N,5.49;
Found: C,68.16; H,5.46; N,5.51%.

(E)-(4-[3-Oxo-3-(1-(3,4-methylenedioxyphenyl)-1,3,4,9-tetrahydro-β-carbolin-2-yl)propenyl]benzyloxy)acetic Acid, Ethyl Ester To a solution of Example 39 (0.7 g, 1.5 mmol) in 50 mL of DMF was added K$_2$CO$_3$ (0.25 g, 1.2 equiv.) and ethylbromoacetate (0.2 mL, 1.1 equiv.). The resulting mixture was heated at 60° C. for 16 hours until disappearance of the starting material (tlc monitoring, DCM:MeOH (95:5)). A new compound was formed (Rf=0.8). After evaporation of DMF, the residue was taken up in 150 mL of DCM, washed with 2×50 mL of water, dried over Na$_2$SO$_4$ and purified via radial chromatography with DCM to give the title compound (0.85 g, 11%) as a white powder.

$^1$H NMR (CDCl$_3$) δ7.8–6.65 (m, 14H), 5.9 (s, 2H), 4.7 (s, 2H), 4.6–4.3 (q, 2H), 4.2–4.0 (m, 4H), 3.6–3.5 (m, 1H), 3.2–2.9 (m, 2H), 1.3–1.2 (t, 3H).

EXAMPLE 90
(E)-1-[1-(3,4-Methylenedioxyphenyl)-1,3,4,9-tetrahydro-β-carbolin-2-yl]-3-(5-amino-2-chlorophenyl)propene-1-one The same method as employed in the preparation of Example 64 but starting from Example 87 gave after recrystallization from EtOH:DCM, the title compound as a white powder in a 17% yield.

MP: 251–252° C.

Analysis for $C_{27}H_{22}ClN_3O_3$. $0.4H_2O$:
Calculated: C,67.68; H,4.8; N,8.77;
Found: C,67.71; H,4.73; N,8.65%.

EXAMPLE 91
(E)-3-Chloro-4-[3-oxo-3-[1-(3,4-methylenedioxyphenyl)-1,3,4,9-tetrahydro-β-carbolin-2-yl]propenyl]benzoic Acid The same method as employed in the preparation of Example 31 but starting from Example 88 gave after recrystallization from 2-propanol the title compound as a yellow powder in a 40% yield.

MP: 169° C.

Analysis for $C_{28}H_{21}N_2O_5$. $H_2O$:
Calculated: C,64.8; H,4.47; N,5.40;
Found: C,64.47; H,4.13; N,5.60%.

EXAMPLE 92
(E)-1-[1-(3,4-Methylenedioxyphenyl)-1,3,4,9-tetrahydro-β-carbolin-2-yl]-3-(3,5-dibromo-4-hydroxyphenyl)propene-1-one The same method as employed in the preparation of Example 20 but starting from (E)-3,5-dibromo-4-hydroxy cinnamic acid gave after recrystallization from EtOH:H$_2$O the title compound as white crystals in a 13% yield.

MP: 148–150° C.

Analysis for $C_{27}H_{20}N_2O_4Br_2$. $1.6EtOH$:
Calculated: C,54.14; H,4.45; N,4.18;
Found: C,54.1; H,4.15; N,3.77%.

EXAMPLE 93
(E)-1-[1-(3,4-Methylenedioxyphenyl)-1,3,4,9-tetrahydro-β-carbolin-2-yl]-3-(4-(2-dimethylaminopropoxy)phenyl)propene-1-one The same method as employed in the preparation of Example 79 but starting from Example 22 and dimethylaminopropyl chloride gave after recrystallization from cyclohexane:DCM:pentane the title compound as white crystals in a 16% yield.

MP: 106° C.

Analysis for $C_{32}H_{33}N_3O_4$. $0.3H_2O$:
Calculated: C,72.65; H,6.40; N,7.94;
Found: C,72.74; H,6.56; N,7.63%.

EXAMPLE 94
(E)-2-Chloro-5-[3-oxo-3-[1-(3,4-methylenedioxyphenyl)-1,3,4,9-tetrahydro-β-carbolin-2-yl]propenyl]benzoic Acid, Methyl Ester The same method as employed in the preparation of Example 20 but starting from Intermediate 33 gave after recrystallization from MeOH:DCM the title compound as a white powder in a 59% yield.

MP: 228° C.

Analysis for $C_{29}H_{23}ClN_2O_5$. $1.05H_2O$:

Calculated: C,65.24; H,4.74; N,5.25;
Found: C,64.91; H,4.27; N,5.13%.

EXAMPLE 95
(E)-1-[1-(3,4-Methylenedioxyphenyl)-1 3,4,9-tetrahydro-β-carbolin-2-yl]-3-(4-(2-diisopropylaminoethoxy)phenyl)propene-1-one The same method as employed in the preparation of Example 79 but starting from Example 22 and diisopropylaminodiethyl chloride gave after recrystallization from MeOH:H$_2$O the title compound as pale yellow crystals in a 12% yield.
MP: 92–93° C.
Analysis for C$_{35}$H$_{39}$N$_3$O$_4$:
Calculated: C,74.31; H,6.95; N,7.43;
Found: C,74.34; H,7.16; N,7.10%.

EXAMPLE 96
(E)-2-Chloro-5-[3-oxo-3-[1-(3,4-methylenedioxyphenyl)-1,3,4,9-tetrahydro-β-carbolin-2-yl]propenyl]benzoic Acid The same method as employed in the preparation of Example 31 but starting from Example 94 gave after recrystallization from MeOH the title compound as white crystals in a 78% yield.
MP: 178° C.
Analysis for C$_{28}$H$_{21}$N$_2$O$_5$. 0.7MeOH:
Calculated: C,65.86; H,4.58; N,5.35;
Found: C, 65.73; H, 4.44; N, 5.51%.

EXAMPLE 97
(E)-1-[1-(3,4-Methylenedioxyphenyl)-1,3,4,9-tetrahydro-β-carbolin-2-yl]-3-(3-hydroxy-4-nitrophenyl)propene-1-one The same method as employed in the preparation of Example 20 but starting from Intermediate 34 gave after recrystallization from EtOH the title compound as yellow crystals in a 77% yield.
MP: 172° C.

EXAMPLE 98
(E)-1-[1-(3,4-Methylenedioxyphenyl)-1,3,4,9-tetrahydro-β-carbolin-2-yl]-3-(3,5-dimethyl-4-hydroxyphenyl)propene-1-one The same method as employed in the preparation of Example 20 but starting from Intermediate 35 gave after recrystallization from MeOH:H$_2$O the title compound as a white powder in a 71% yield.
MP: 151–152° C.
Analysis for C$_{29}$H$_{26}$N$_2$O$_4$. 0.4H$_2$O:
Calculated: C,73.52; H,5.7; N,5.91;
Found: C,73.56; H,5.59; N6.29%.

EXAMPLE 99
(E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one The same method as employed in the preparation of Example 79 but starting from Example 97 and dimethylaminodiethyl chloride gave after recrystallization from MeOH the title compound as a pale yellow powder in a 18% yield.
MP: 189° C.
Analysis for C$_{31}$H$_{30}$N$_4$O$_6$. 1.5H$_2$O:
Calculated: C,64.02; H,5.72; N,9.63;
Found: C,64.18; H,5.41; N,9.21%.

EXAMPLE 100
(E)-1-[1-(3,4-Methylenedioxyphenyl)-1,3,4,9-tetrahydro-β-carbolin-2-yl]-3-(3-(2-dimethylaminoethoxy)-4-aminophenyl)propene-1-one The same method as employed in the preparation of Example 64 but starting from Example 99 gave after recrystallization from iPr$_2$O the title compound as a pale yellow powder in a 17% yield.
MP: 143° C.
Analysis for C$_{31}$H$_{32}$N$_4$O$_4$. 0.5H$_2$O:
Calculated: C,69.78; H,6.23; N,10.5;
Found: C,69.87; H,5.98; N,10.42%.

EXAMPLE 101
(E)-1-[1-(3,4-Methylenedioxyphenyl)-1,3,4,9-tetrahydro-β-carbolin-2-yl]-3-(3-nitro-4-hydroxy-5-methoxyphenyl)propene-1-one The same method as employed in the preparation of Example 20 but starting from Intermediate 36 gave after recrystallization from EtOH:DCM the title compound as pale yellow crystals in a 45% yield.
MP: 172° C.
Analysis for C$_{28}$H$_{23}$N$_3$O$_7$. 0.8H$_2$O:
Calculated: C,63.7; H,4.7; N,7.96;
Found: C,63.71; H,4.31; N,7.98%.

EXAMPLE 102
(E)-1-[1-(3,4-Methylenedioxyphenyl)-1,3,4,9-tetrahydro-β-carbolin-2-yl]-3-(3-chloro-phenyl)propene-1-one The same method as employed in the preparation of Example 20 but starting from (E)-3-chlorocinnamic acid, gave after recrystallization from EtOH the title compound as white crystals in a 48% yield.
MP: 212–213° C.
Analysis for C$_{27}$H$_{21}$ClN$_2$O:
Calculated: C,70.97; H,4.63; N,6.13
Found: C,70.65; H,4.63; N,6.16%.

EXAMPLE 103
(E)-1-[1-(4-Methoxy-phenyl)-1,3,4,9-tetrahydro-β-carbolin-2-yl]-3-(2-chloro-5-nitrophenyl)propene-1-one The same method as employed in the preparation of Example 20 but starting from Intermediate 2 and (E)-2-chloro-5-nitrocinnamic acid gave after recrystallization from 2-propanol the title compound as a yellow powder white in a 18% yield.
MP: 136–138° C.
Analysis for C$_{27}$H$_{22}$ClN$_3$O$_4$. 0.2H$_2$O:
Calculated: C,65.98; H,4.59; N,8.55;
Found: C,65.91; H,4.4; N,8.42%.

EXAMPLE 104
(E)-1-[1-(3,4-Methylenedioxyphenyl)-1,3,4,9-tetrahydro-β-carbolin-2-yl]-3-(2,6-dichlorophenyl)propene-1-one The same method as employed in the preparation of Example 20 but starting from (E)-2,6-dichlorocinnamic acid gave after recrystallization from cyclohexane the title compound as a white powder in a 41% yield.
MP: 118–120° C.
Analysis for C$_{27}$H$_{20}$Cl$_2$N$_2$O$_3$. 0.2H$_2$O:
Calculated: C,65.52; H,4.15; N,5.66;
Found: C,65.74; H,4.62; N,5.29%.

EXAMPLE 105
(E)-1-[1-(3,4-Methylenedioxyphenyl)-1,3,4,9-tetrahydro-β-carbolin-2-yl]-3-(4-methylaminomethylphenyl)propene-1-one A solution of (E)-1-[1-(3,4-methylenedioxyphenyl)-1,3,4,9-tetrahydro-β-carbolin-2-yl]-3-(4-methyliminomethylphenyl)propene-1-one (0.46 g, 1.1 mmol), NaBH$_3$CN (0.14 g, 2.3 mmol) and acetic acid (0.11 mL) in 20 mL of MeOH was stirred at rt for one hour. The reaction mixture was quenched with 50 mL of an aqueous saturated solution of NaHCO$_3$. Extraction with 2×30 mL of DCM, washing with brine, drying over Na$_2$SO$_4$ and concentration in vacuo gave a residue that was purified via flash chromatography of silica gel using DCM:MeOH (97:3) as eluting solvent. Recrystallization from DCM:cyclohexane gave the title compound (0.05 g, 10%) as a white powder.

MP: 201° C.

Analysis for $C_{29}H_{27}Cl_2N_3O_3 \cdot 0.5H_2O$:

Calculated: C,73,4; H,5.95; N,8.85;

Found: C,73.66; H,5.82; N,8.57%.

A stirred solution of Example 23 (0.5 g, 1.0 mmol) in MeOH was refluxed with methylamine (1.6 mL, 1.5 equiv., 33% in EtOH) for one hour. Evaporation in vacuo gave (E)-1-[1-(3,4-methylenedioxyphenyl)-1,3,4,9-tetrahydro-β-carbolin-2-yl]-3-(4-methyliminomethylphenyl)propene-1-one (0.46 g, 90%).

$^1$H NMR (CDCl$_3$, 250 MHz) δ8.2 (d, 1H), 8.1 (s, 1H), 7.8–7.65 (m, 3H), 7.55–7.5 (m, 3H), 7.4–7.1 (m, 3H), 7.0–6.85 (m, 2H), 6.8–6.6 (dd, 2H), 5.9 (s, 2H), 4.2–4.1 (br d, 1H), 3.5 (s+m, 4H), 3.05–2.85 (m, 2H).

EXAMPLE 106

(E)-1-[1-(3,4-Methylenedioxyphenyl)-1,3,4,9-tetrahydro-β-carbolin-2-yl]-3-(3-methylphenyl)-propene-1-one The same method as employed in the preparation of Example 20 but starting from (E)-3-methylcinnamic acid gave after recrystallization from MeOH the title compound as a white powder in a 67% yield.

MP: 196° C.

Analysis for $C_{28}H_{24}N_2O_3$:

Calculated: C,77.04; H,5.54; N,6.62;

Found: C,76.76; H,5.56; N,6.33%.

EXAMPLE 107

(E)-N-Methyl-(4-[3-oxo-3-(1-(3,4-methylenedioxyphenyl)-1,3,4,9-tetrahydro-β-carbolin-2-yl)propenyl] benzenesulfonamide The same method as employed in the preparation of Example 20 but starting from (E)-4-(N-methylsulfonamide) cinnamic acid gave after recrystallization from EtOH:H$_2$O the title compound as white crystals in a 79% yield.

MP: 162° C.

Analysis for $C_{28}H_{25}N_3O_5 \cdot 0.4EtOH$:

Calculated: C,64.78; H,5.17; N,7.87;

Found: C,64.46; H,4.82; N,7.76%.

EXAMPLE 108

(E)-1-[1-(3,4-Methylenedioxyphenyl)-1,3,4,9-tetrahydro-β-carbolin-2-yl]-3-(3-hydroxy-4-acetylphenyl)propene-1-one The same method as employed in the preparation of Example 20 but starting from (E)-3-hydroxy-4-acetylcinnamic acid gave after recrystallization from EtOH the title compound as yellow crystals in a 87% yield.

MP: 217–218° C.

Analysis for $C_{29}H_{24}N_2O_5$:

Calculated: C,72.49; H,5.03; N,5.83;

Found: C,72.24; H,5.25; N,5.53%.

EXAMPLE 109

(E)-1-[1-(2,3-Dihydrobenzofuran-5-yl)-1,3,4,9-tetrahydro-β-carbolin-2-yl]-3-(2-chloro-5-nitrophenyl)propene-1-one The same method as employed in the preparation of Example 20 but starting from Intermediate 10 and (E)-2-chloro-5-nitrocinnamic acid gave after recrystallization from EtOH:H$_2$O (95:5) the title compound as yellow crystals in a 62% yield.

MP: 154° C.

Analysis for $C_{27}H_{22}ClN_3O_4 \cdot 0.5(H_2O:MeOH)$:

Calculated: C,66.08; H,4.55; N,8.36;

Found: C,66.3; H,4.52; N,7.94%.

EXAMPLE 110

(E)-1-[1-(3,4-Methylenedioxyphenyl)-1,3,4,9-tetrahydro-β-carbolin-2-yl]-3-(2-hydroxyphenyl)propene-1-one The same method as employed in the preparation of Example 20 but starting from (E)-2-hydroxy cinnamic acid gave after recrystallization from EtOH:H$_2$O, the title compound as white crystals in a 47% yield;

MP: 154° C.

Analysis for $C_{27}H_{22}N_2O_4 \cdot 0.6H_2O$:

Calculated: C,72.18; H,5.2; N,6.24;

Found: C,72.19; H,4.93; N,6.13%.

EXAMPLE 111

(E)-1-[1-(3,4-Methylenedioxyphenyl)-1,3,4,9-tetrahydro-β-carbolin-2-yl]-3-(3-nitro-2-piperidin-1-ylphenyl)propene-1-one The same method as employed in the preparation of Example 20 but starting from Intermediate 37 gave after recrystallization from MeOH the title compound as yellow crystals in a 31% yield.

MP: 162–163° C.

Analysis for $C_{32}H_{30}N_4O_5 \cdot 0.2H_2O$:

Calculated: C,65.52; H,5.84; N,9.55;

Found: C,65.9; H,5.49; N,9.59%.

EXAMPLE 112

(E)-1-[1-(2,3-Dihydrobenzofuran-5-yl)-1,3,4,9-tetrahydro-β-carbolin-2-yl]-3-phenylpropene-1-one The same method as employed in the preparation of Example 1 but starting from Intermediate 10 gave after recrystallization from EtOH the title compound as white crystals in a 52% yield.

MP: 190° C.

Analysis for $C_{28}H_{24}N_2O_2$:

Calculated: C,79.98; H,5.75; N,6.66;

Found: C,79.94; H,5.86; N,6.62%.

EXAMPLE 113

(E)-1-[1-(4-Isopropylphenyl)-1,3,4,9-tetrahydro-β-carbolin-2-yl]-3-(3-nitrophenyl)propene-1-one The same method as employed in the preparation of Example 20 but starting from Intermediate 11 and (E)-3-nitrocinnamic acid gave after recrystallization from EtOH the title compound as yellow crystals in a 54% yield.

MP: 195° C.

Analysis for $C_{29}H_{27}N_3O_3$:

Calculated: C,74.82; H,5.85; N,9.03;

Found: C,74.43; H,5.84; N,9.17%.

EXAMPLE 114

(E)-1-[1-(2,3-Dihydrobenzofuran-5-yl)-1,3,4,9-tetrahydro-β-carbolin-2-yl]-3-(3-nitrophenyl)propene-1-one The same method as employed in the preparation of Example 20 but starting from Intermediate 10 and (E)-3-nitrocinnamic acid gave after recrystallization from EtOH the title compound as white crystals in a 35% yield.

MP: 174–176° C.

Analysis for $C_{28}H_{23}N_3O_4 \cdot 0.1H_2O$:

Calculated: C,71.97; H,5.0; N,8.99;

Found: C,71.78; H,4.89; N,8.83%.

EXAMPLE 115

(E)-(R)-1-[1-(3,4-Methylenedioxyphenyl)-1,3,4,9-tetrahydro-β-carbolin-2-yl]-3-phenylpropene-1-one The same method as employed in the preparation of Example 1 but starting from Intermediate 19 gave after recrystallization from EtOH the title compound as white crystals in a 60% yield.

MP: 232–233° C.

Analysis for $C_{27}H_{22}N_2O_3 \cdot 0.2H_2O$:

Calculated: C,76.11; H,5.3; N,6.57;
Found: C,76.2; H,5.27; N,6.77%
$[\alpha]_D^{21}$=−336 (c=0.50, MeOH).

EXAMPLE 116
(E)-(S)-1-[1-(3,4-Methylenedioxyphenyl)-1,3,4,9-tetrahydro-β-carbolin-2-yl]-3-phenylpropene-1-one The same method as employed in the preparation of Example 1 but starting from Intermediate 18 gave after recrystallization from iPrOH the title compound as white crystals in a 32% yield.
MP: 235–236° C.
Analysis for $C_{27}H_{22}N_2O_3$. 0.1$H_2O$:
Calculated: C,76.43; H,5.27; N,6.6;
Found: C,76.26; H,5.21; N,6.61%.
$[\alpha]_D^{21}$=378 (c=0.5, MeOH).

EXAMPLE 117
(E)-1-[1-(4-Methoxyphenyl)-1,3,4,9-tetrahydro-β-carbolin-2-yl]-3(3-nitrophenyl)propene-1-one The same method as employed in the preparation of Example 20 but starting from Intermediate 2 and (E)-3-nitrocinnamic acid gave after recrystallization from EtOH the title compound as yellow crystals in a 63% yield.
MP: 227° C.
Analysis for $C_{27}H_{23}N_3O_4$. 0.1EtOH:
Calculated: C,71.32; H,5.19; N,9.17;
Found: C,70.96; H,5.14; N,9.23%.

EXAMPLE 118
(E)-1-[1-(4-Methylphenyl)-1,3,4,9-tetrahydro-β-carbolin-2-yl]-3-(2-chloro-5-nitrophenyl)propene-1-one The same method as employed in the preparation of Example 20 but starting from Intermediate 6 and (E)-2-chloro-5-nitrocinnamic acid gave after recrystallization from EtOH the title compound as a yellow powder in a 57% yield.
MP: 211–213° C.
Analysis for $C_{27}H_{23}ClN_3O_3$:
Calculated: C,68.72; H,4.7; N,8.9;
Found: C,68.42; H,4.73; N.8.91%.

EXAMPLE 119
(E)-N-(Tetrahydrofuran-2-ylmethyl)-3-[3-oxo-3-(1-(3,4-methylenedioxy)-1,3,4,9-tetrahydro-β-carbolin-2-yl)propenyl]benzamide The same method as employed in the preparation of Example 20 but starting from Example 70 and tetrahydrofurfurylamine gave after recrystallization from EtOH the title compound as a white powder in a 30% yield.
MP: 172–173° C.
Analysis for $C_{33}H_{31}N_3O_5$. 0.4$H_2O$:
Calculated: C,71.18; H,5.76; N,7.55;
Found: C,71.1; H,5.88; N,7.45%.

EXAMPLE 120
(E)-1-[1-(Indan-5-yl)-1,3,4,9-tetrahydro-β-carbolin-2-yl]-3-phenylpropene-1-one The same method as employed in the preparation of Example 1 but starting from Intermediate 9 and tetrahydrofurfurylamine gave after recrystallization from EtOH the title compound as white crystals in a 51% yield.
MP: 223° C.
Analysis for $C_{29}H_{26}N_2O$. 0.4$H_2O$:
Calculated: C,81.81; H,5.34; N,6.58;
Found: C,81.87; H,6.34; N,6.5%.

EXAMPLE 121
(E)-1-[1-(3,4-Methylenedioxyphenyl)-1,3,4,9-tetrahydro-β-carbolin-2-yl]-3-(3-acetylphenyl)propene-1-one The same method as employed in the preparation of Example 20 but starting from 3-acetylcinnamic acid (prepared according to the procedure of Cleland, G. H. *J. Org. Chem.* 1969, 34, 744–747) gave after recrystallization from EtOH the title compound as a yellow powder in a 42% yield.
MP: 191° C.
Analysis for $C_{29}H_{24}ClN_2O_4$:
Calculated: C,74.98; H,5.21; N,6.03;
Found: C,74.85; H,5.28; N,6.1%.

EXAMPLE 122
(E)-1-[1-(2,3-Dihydrobenzofuran-5-yl)-1,3,4,9-tetrahydro-β-carbolin-2-yl]-3-(4-(2-dimethylaminoethoxy)phenyl)propene-1-one The same method as employed in the preparation of Example 20 but starting from Intermediate 10 and Intermediate 25 gave after recrystallization from $CH_3CN$ the title compound as white crystals in a 37% yield.
MP: 146° C.
Analysis for $C_{32}H_{33}N_3O_3$. 1.5$H_2O$:
Calculated: C,71.89; H,6.79; N,7.86;
Found; C,72.04; H,7.09; N,7.93%.

EXAMPLE 123
(E)-4-[3-Oxo-3-[1-(4-methoxyphenyl)-1,3,4,9-tetrahydro-β-carbolin-2-yl]propenyl]benzoic Acid, Methyl Ester The same method as employed in the preparation of Example 20 but starting from Intermediate 2 and (E)-4-(2-carboxyvinyl)benzoic acid, methyl ester gave after recrystallization from EtOH the title compound as yellow crystals in a 73% yield.
MP: 189° C.
Analysis for $C_{29}H_{26}N_2O_4$. 0.1EtOH:
Calculated; C,74.44; H,5.69; N,5.95;
Found: C,74.1; H, 5.65; N,6.01%.

EXAMPLE 124
(E)-1-[1-(3,4-Methylenedioxyphenyl)-1,3,4,9-tetrahydro-β-carbolin-2-yl]-3-(4-methyl-3,4-dihydro-2H-benzo[1,4]oxazin-6-yl)propene-1-one The same method as employed in the preparation of Example 20 but starting from Intermediate 38 gave after recrystallization from EtOH the title compound as yellow crystals in a 69% yield.
MP: 231–232° C.
Analysis for $C_{29}H_{26}N_2O_4$. 0.1EtOH:
Calculated: C,73.01; H,5.51; N, 8.51;
Found: C,72.54; H,5.58; N,8.44%.

EXAMPLE 125
(E)-1-[1-(3,4-Methylenedioxyphenyl)-1,3,4,9-tetrahydro-β-carbolin-2-yl]-3-(2-hydroxy-5-nitrophenyl)propene-1-one The same method as employed in the preparation of Example 20 but starting from Intermediate 39 gave after recrystallization from EtOH the title compound as yellow crystals in a 30% yield.
MP: 205° C.
Analysis for $C_{27}H_{21}N_3O_6$. 0.6EtOH:
Calculated: C,65.78; H,5.14; N,7.94;
Found: C,65.52; H,4.98; N,8.04%.

EXAMPLE 126
(E)-4-[3-Oxo-3-[1-(2,3-dihydrobenzofuran-5-yl)-1,3,4,9-tetrahydro-β-carbolin-2-yl]propenyl]benzoic Acid, Methyl Ester The same method as employed in the preparation of Example 20 but starting from Intermediate 10 and (E)-4-(2- carboxyvinyl)benzoic acid, methyl ester gave after recrystallization from EtOH the title compound as white needles in a 88% yield.
MP: 186° C.
Analysis for $C_{30}H_{26}N_2O_4$. $0.2H_2O$:
Calculated: C,74.73; H,5.52; N,5.81;
Found: C,75.45; H, 5.38; N,6.07%.

EXAMPLE 127

(E)-4-[3-Oxo-3-[1-(4-methoxyphenyl)-1,3,4,9-tetrahydro-β-carbolin-2-yl]propenyl]benzoic Acid The same method as employed in the preparation of Example 31 but starting from Example 123 gave after recrystallization from MeOH:$H_2O$ the title compound as a grey powder in a 43% yield.
MP: 147–149° C.
Analysis for $C_{28}H_{24}N_2O_4$:
Calculated: C,74.32; H,5.35; N,6.19;
Found: C,74.3; H,5.37; N,6.07%.

EXAMPLE 128

(E)-4-[3-Oxo-3-[1-(2,3-dihydrobenzofuran-5-yl)-1,3,4,9-tetrahydro-β-carbolin-2-yl]propenyl]benzoic Acid The same method as employed in the preparation of Example 31 but starting from Example 126 gave after recrystallization from MeOH the title compound as white crystals in a 53% yield.
MP: 222–224° C.
Analysis for $C_{29}H_{24}N_2O_4$:
Calculated: C,74.98; H,5.21; N,6.03;
Found: C,75.21; H,5.3; N,6.21%.

EXAMPLE 129

(E)-1-[1-(Benzofuran-5-yl)-1,3,4,9-tetrahydro-β-carbolin-2-yl]-3-phenylpropene-1-one The same method as employed in the preparation of Example 1 but starting from Intermediate 12 gave after recrystallization from EtOH the title compound as white crystals in a 35% yield.
MP: 241–242° C.
Analysis for $C_{28}H_{22}N_2O_2$:
Calculated: C,80.36; H,5.3; N,6.69;
Found: C,80.44; H,5.3; N,6.89%.

EXAMPLE 130

(E)-3-[3-Oxo-3-(1-(3,4-methylenedioxyphenyl)-1,3,4,9-tetrahydro-β-carbolin-2-yl)-propenyl]phenyl) trifluoromethanesulfonic Acid, Phenyl Ester The same method as employed in the preparation of Example 20 but starting from Intermediate 40 gave after recrystallization from EtOH the title compound as white crystals in a 38% yield.
MP: 169° C.
Analysis for $C_{28}H_{21}F_3N_2O_6S$. $0.2H_2O$:
Calculated: C,58.58; H,3.76; N,4.88;
Found: C,58.84; H,3.71; N,4.3%.

EXAMPLE 131

(E)-1-[1-(3,4-Methylenedioxyphenyl)-1,3,4,9-tetrahydro-β-carbolin-2-yl]-3-[4-(2-hydroxyethoxy)phenyl]propene-1-one The same method as employed in the preparation of Example 20 but starting from (E)-4-(2-hydroxyethoxy) phenyl (prepared according to the procedure of Oku, T.; Kayakiri, H.; Satoh, S.; Abe, Y.; Sawada, Y.; Inoue, T.; Tanaka, H.; EP 622361) gave after recrystallization from EtOH the title compound as white crystals in a 57% yield.
MP: 136° C.
Analysis for $C_{29}H_{26}N_2O_5$. 1.2EtOH:
Calculated: C,58.58; H,3.76; N,4.88;
Found: C,58.84; H,3.71; N,4.3%.

EXAMPLE 132

(E)-1-[1-(Benzofuran-5-yl-1,3,4,9-tetrahydro-β-carbolin-2-yl)]-3-(4-(2-dimethylaminoethoxy)phenyl)propene-1-one The same method as employed in the preparation of Example 20 but starting from Intermediate 12 and Intermediate 25 gave after recrystallization from $CH_3CN$ the title compound as white crystals in a 23% yield.
MP: 159° C.
Analysis for $C_{32}H_{31}N_3O_3$. $0.1H_2O$:
Calculated: C,75.75; H,6.2; N,8.28;
Found: C,75.58; H,5.97; N,8.35%.

EXAMPLE 133

(E)-1-[1-(3,4-Methylenedioxyphenyl)-1,3,4,9-tetrahydro-β-carbolin-2-yl]-3-(2-dimethylaminophenyl)propene-1-one The same method as employed in the preparation of Example 20 but starting from (E)-2-dimethylaminocinnamic acid (prepared according to the procedure of Suschitzky, H.; Hollywood, F. *Synthesis* 1982, 662–665) gave after recrystallization from MeOH:$H_2O$ the title compound as a yellow powder in a 51% yield.
MP: 172° C.
Analysis for $C_{29}H_{27}N_3O_3$:
Calculated: C,74.82; H,9.89; N,9.03
Found: C,74.75; H,5.85; N,8.9%.

EXAMPLE 134

(E)-1-[1-(3,4-Methylenedioxyphenyl)-1,3,4,9-tetrahydro-β-carbolin-2-yl]-3-(2-piperidin-1-ylphenyl)propene-1-one The same method as employed in the preparation of Example 20 but starting from (E)-2-piperidin-1-ylcinnamic acid (prepared according to the procedure of Suschitzky, H.; Hollywood, F. *Synthesis* 1982, 662–665) gave after recrystallization from MeOH:$H_2O$ the title compound as a yellow powder in a 37% yield.
MP: 129° C.
Analysis for $C_{32}H_{31}N_3O_3$:
Calculated: C,76.02; H,6.18; N,8.31;
Found: C,75.66; H,6.18; N,8.29%.

EXAMPLE 135

(E)-4-[3-Oxo-3-[1-(benzofuran-5-yl-1,3,4,9-tetrahydro-β-carbolin-2-yl]-propenyl]benzoic Acid, Methyl Ester The same method as employed in the preparation of Example 20 but starting from Intermediate 12 and (E)-4-(2-carboxyvinyl)benzoic acid methyl ester gave after recrystallization from EtOH the title compound as yellow crystals in a 76% yield.
MP: 221° C.
Analysis for $C_{30}H_{24}N_2O_4$:
Calculated: C,75.62; H,5.08; N,5.88;
Found: C,75.75; H,5.31; N,5.86%.

EXAMPLE 136

(E)-4-[3-(1-Benzofuran-5-yl-1,3,4,9-tetrahydro-β-carbolin-2-yl)-3-oxo-propenyl]Benzoic Acid The same method as employed in the preparation of Example 31 but starting from Example 135 gave after recrystallization from $CH_3CN$ the title compound as yellow crystals in a 66% yield.
MP: 283° C.
Analysis for $C_{29}H_{22}N_2O_4$. $0.6H_2O$:
Calculated: C,73.59; H,4.94; N,5.92;
Found: C,73.48; H,4.78; N,5.93%.

EXAMPLE 137

(E)-4-[3-Oxo-3-(1-(3,4-methylenedioxyphenyl)-1,3,4,9-tetrahydro-β-carbolin-2-yl)propenyl]phenyl) trifluoromethanesulfonic Acid, Phenyl Ester The same method as employed in the preparation of Example 20 but starting from Intermediate 41 gave after recrystallization from EtOH the title compound as white crystals in a 51% yield.

MP: 254° C.
Analysis for $C_{28}H_{21}F_3N_2O_6S$:
Calculated: C,58.95; H,3.71; N,4.91;
Found: C,58.79; H,3.8; N,4.77%.

EXAMPLE 138

(E)-1-[1-(3,4-Methylenedioxyphenyl)-1,3,4,9-tetrahydro-β-carbolin-2-yl]-3-(2-(2-dimethylaminoethoxy)phenyl) propene-1-one The same method as employed in the preparation of Example 79 but starting from Example 110 and dimethylaminodiethyl chloride gave after recrystallization from $CH_3CN$:pentane the title compound as yellow crystals in a 70% yield.

MP: 131° C.
Analysis for $C_{31}H_{31}N_3O_4$. $1.3H_2O$:
Calculated: C,68.95; H,6.35; N,7.88;
Found: C,69.77; H,6.28; N,7.84%.

EXAMPLE 139

(E)-1-[1-(3-Fluoro-4-methoxyphenyl)-1,3,4,9-tetrahydro-β-carbolin-2-yl]-3-phenylpropene-1-one The same method as employed in the preparation of Example 1 but starting from Intermediate 14 gave after recrystallization from DCM:cyclohemane the title compound as white crystals in a 66% yield.

MP: 122° C.
Analysis for $C_{27}H_{23}FN_2O_2$. $0.4CH_2Cl_2$:
Calculated: C,71.47; H,5.21; N,6.08;
Found: C,71.46; H,5.27; N,6.12%.

EXAMPLE 140

(E)-(R)-1-[1-(2,3-Dihydrobenzofuran-5-yl)-1,3,4,9-tetrahydro-β-carbolin-2-yl)]-3-(4-(2-dimethylaminoethoxy) phenyl)propene-1-one The same method as employed in the preparation of Example 20 but starting from Intermediate 20 and Intermediate 25 gave after recrystallization from $CH_3CN$ the title compound as white crystals in a 85% yield.

MP: 187–189° C.
Analysis for $C_{32}H_{33}N_3O_3$:
Calculated: C,75.71; H,6.55; N,8.20;
Found: C,75.60; H,6.76; N,8.10%.
$[\alpha]_D^{21}=-310$ (c=0.40, $CHCl_3$).

EXAMPLE 141

(E)-1-(2,3-Dihydrobenzo[1,4]dioxin-6-yl)-1,3,4,9-tetrahydro-β-carbolin-2-yl]-3-phenylpropene-1-one The same method as employed in the preparation of Example 1 but starting from Intermediate 13 gave after recrystallization from EtOH the title compound as white crystals in a 39% yield.

MP: 216° C.
Analysis for $C_{28}H_{24}N_2O_3$. $0.6H_2O$:
Calculated: C,75.18; H,5.68; N,6.26;
Found: C,75.17; H,5.41; N,6.4%.

EXAMPLE 142

(E)-1-[1-(2,3-Dihydrobenzofuran-5-yl)-1,3,4,9-tetrahydro-β-carbolin-2-yl)]-3-(4-(2-pyrrolidin-1-ylethoxy)phenyl) propene-1-one The same method as employed in the preparation of Example 20 but starting from Intermediate 10 and Intermediate 42 gave after recrystallization from 2-propanol:$iPr_2O$ the title compound as white crystals in a 26% yield.

MP: 152° C.
Analysis for $C_{34}H_{35}N_3O_3$. $0.5H_2O$:
Calculated: C,75.25; H,6.69; N,7.74;
Found: C,75.31; H,6.6; N,7.69%.

EXAMPLE 143

(E)-1-[1-(3,4-Methylenedioxyphenyl)-1,3,4,9-tetrahydro-β-carbolin-2-yl]-3-[4-pyrrolidin-1-ylphenyl]propene-1-one The same method as employed in the preparation of Example 20 but starting from Intermediate 43 gave after recrystallization from EtOH:$H_2O$ the title compound as white crystals in a 73% yield.

MP: 154° C.
Analysis for $C_{31}H_{29}N_3O_3$. $0.6H_2O$:
Calculated: C,74.11; H,6.06; N,8.36;
Found: C,74.22; H,5.97; N,7.97%.

EXAMPLE 144

(E)-(R)-1-[1-(2,3-Dihydrobenzofuran-5-yl)-1,3,4,9-tetrahydro-β-carbolin-2-yl]-3-(3-nitrophenyl)propene-1-one The same method as employed in the preparation of Example 20 but starting from Intermediate 20 and (E)-3-nitrocinnamic acid gave after recrystallization from EtOH the title compound as yellow crystals in a 51% yield.

MP: 155° C.
Analysis for $C_{28}H_{23}N_3O_4$:
Calculated: C,72.25; H,4.98; N,9.03;
Found: C,72.2; H,5.0; N,9.01%.
$[\alpha]_D^{19}=-347$ (c=0.33, MeOH).

EXAMPLE 145

(E)-1-[1-(3,4-Methylenedioxyphenyl)-1,3,4,9-tetrahydro-β-carbolin-2-yl]-3-[4-imidazol-1-ylphenyl]propene-1-one The same method as employed in the preparation of Example 20 but starting from Intermediate 44 gave after recrystallization from EtOH the title compound as white crystals in a 69% yield.

MP: 204° C.
Analysis for $C_{30}H_{24}N_4O_3$. $0.6H_2O$:
Calculated: C,72.68; H,5.04; N,11.3;
Found: C,72.67; H,4.85; N,11.34%.

EXAMPLE 146

(E)-4-[3-[1-(2,3-Dihydrobenzo[1,4]dioxin-6-yl)-1,3,4,9-tetrahydro-β-carbolin-2-yl]-3-oxopropenyl]benzoic Acid, Methyl Ester The same method as employed in the preparation of Example 20 but starting from Intermediate 13 and (E)-4-(2-carboxyvinyl)benzoic acid, methyl ester gave after recrystallization from MeOH the title compound as a white powder in a 35% yield.

MP: 136° C.
Analysis for $C_{30}H_{26}N_2O_5$. $0.1H_2O$:
Calculated: C,72.6; H,5.32; N, 5.64;
Found: C,72.31; H,5.26; N,5.74%.

EXAMPLE 147

(E)-1-[1-(2,3-Dihydrobenzo[1,4]dioxin-6-yl)-1,3,4,9-tetrahydro-β-carbolin-2-yl]-3-(3-nitrophenyl)propene-1-one The same method as employed in the preparation of Example 20 but starting from Intermediate 13 and (E)-3-nitrocinnamic acid gave after recrystallization from EtOH the title compound as a pale yellow powder in a 93% yield.

MP: 154° C.
Analysis for $C_{28}H_{23}N_3O_5$. $0.6H_2O$:
Calculated: C,68.31; H,4.95; N,8.54;
Found: C,68.41; H,4.87; N,8.61%.

EXAMPLE 148
(E)-1-[1-(2,3-Dihydrobenzo[1,4]dioxin-6-yl)-1,3,4,9-tetrahydro-β-carbolin-2-yl)]-3-(4-(2-dimethylaminoethoxy)phenyl)propene-1-one The same method as employed in the preparation of Example 20 but starting from Intermediate 13 and Intermediate 25 gave after recrystallization from $CH_3CN$ the title compound as a white powder in a 65% yield.

MP: 145° C.

EXAMPLE 149
(E)-1-[1-(3-Fluoro-4-methoxyphenyl)-1,3,4,9-tetrahydro-β-carbolin-2-yl)]-3-(4-(2-dimethylaminoethoxy)phenyl)propene-1-one The same method as employed in the preparation of Example 20 but starting from Intermediate 14 and Intermediate 25 gave after recrystallization from $iPr_2O$ the title compound as a white powder in a 60% yield.

MP: 103° C.

Analysis for $C_{31}H_{32}FN_3O_3 \cdot 0.4H_2O$:
Calculated: C,71.49; H,6.35; N,8.07;
Found: C,71.4; H,6.51; N,8.04%.

EXAMPLE 150
(E)-4-[3-[1-(2,3-Dihydrobenzo[1,4]dioxin-6-yl)-1,3,4,9-tetrahydro-β-carbolin-2-yl]-3-oxopropenyl]benzoic Acid The same method as employed in the preparation of Example 31 but starting from Example 146 gave after recrystallization from MeOH the title compound as a white powder in a 93% yield.

MP: 253° C.

Analysis for $C_{29}H_{24}N_2O_5 \cdot 0.7H_2O$:
Calculated: C,70.63; H,5.19; N,5.68;
Found: C,70.78; H,5.09; N,5.72%.

EXAMPLE 151
(E)-(R)-1-[1-(2,3-Dihydrobenzofuran-5-yl)-1,3,4,9-tetrahydro-β-carbolin-2-yl]-3-phenylpropene-1-one The same method as employed in the preparation of Example 1 but starting from Intermediate 20 gave after recrystallization from MeOH the title compound as white crystals in a 100% yield.

MP: 267° C.

Analysis for $C_{28}H_{24}N_2O_2$:
Calculated: C,79.98; H,5.75; N,6.66;
Found: C,79.86; H,5.89; N,6.72%.
$[\alpha]_D^{22}=-362$ (c=0.35, $CHCl_3$).

EXAMPLE 152
(E)-(S)-1-[1-(2,3-Dihydrobenzofuran-5-yl)-1,3,4,9-tetrahydro-β-carbolin-2-yl]-3-(4-(2-dimethylaminoethoxy)phenyl)propene-1-one The same method as employed in the preparation of Example 20 but starting from Intermediate 21 and Intermediate 25 gave after recrystallization from $CH_3CN$ the title compound as beige crystals in a 79% yield.

MP: 153° C.

Analysis for $C_{32}H_{33}N_3O_3 \cdot 0.5H_2O$:
Calculated: C, 74.39; H,6.63; N,8.13;
Found: C,74.36; H,6.69; N,8.44%.
$[\alpha]_D^{21}=314$ (c=0.40, $CHCl_3$).

EXAMPLE 153
(E)-1-[1-(2,3-Dihydrobenzofuran-5-yl)-1,3,4,9-tetrahydro-β-carbolin-2-yl]-3-(4-aminophenyl)propene-1-one The same method as employed in the preparation of Example 20 but starting from Intermediate 10 and (E)-4-aminocinnamic acid gave after recrystallization from iPrOH the title compound as white crystals in a 43% yield.

MP: 183° C.

Analysis for $C_{30}H_{31}N_3O_2 \cdot 1.6H_2O$:
Calculated: C,76.59; H,5.83; 9.57;
Found: C,76.62; H,5.82; N,9.59%.

EXAMPLE 154
(E)-(S)-1-[1-(2,3-Dihydrobenzofuran-5-yl)-1,3,4,9-tetrahydro-β-carbolin-2-yl]-3-phenylpropene-1-one The same method as employed in the preparation of Example 1 but starting from Intermediate 21 gave after recrystallization from EtOH the title compound as white crystals in a 98% yield.

MP: 266° C.

Analysis for $C_{28}H_{24}N_2O_2 \cdot 0.2H_2O$:
Calculated: C,79.30; H,5.80; N,6.61;
Found: C,79.24; H,5.92; N,6.48%.
$[\alpha]_D^{20}=356$ (c=0.35, $CHCl_3$).

EXAMPLE 155
(E)-(S)-1-[1-(2,3-Dihydrobenzofuran-5-yl)-1,3,4,9-tetrahydro-β-carbolin-2-yl]-3-(3-nitrophenyl)propene-1-one The same method as employed in the preparation of Example 20 but starting from Intermediate 21 and (E)-3-nitrocinnamic acid gave after recrystallization from 2-propanol the title compound as yellow crystals in a 77% yield.

MP: 143° C.

Analysis for $C_{28}H_{23}N_3O_4 \cdot 0.3H_2O$:
Calculated: C,71.42; H,5.05; N,8.92;
Found: C,71.51; H,4.98; N,9.23%.
$[\alpha]_D^{19}=294$ (c=0.30, $CHCl_3$).

EXAMPLE 156
(E)-(R)-1-[1-(2,3-Dihydrobenzofuran-5-yl)-1,3,4,9-tetrahydro-β-carbolin-2-yl]-3-(4-(1-(S)-methylpyrrolidin-2-yl-methoxy)phenyl)propene-1-one The same method as employed in the preparation of Example 20 but starting from Intermediate 20 and Intermediate 45 gave after recrystallization from 2-propanol the title compound as white crystals in a 73% yield.

MP: 167° C.

Analysis for $C_{34}H_{35}N_3O_3$:
Calculated: C,76.52; H,6.61; N,7.87;
Found: C,76.13; H, 6.71; N,7.96%.
$[\alpha]_D^{20}=-344$ (c=0.30, $CHCl_3$).

EXAMPLE 157
(E)-(R)-1-[1-(2,3-Dihydrobenzofuran-5-yl)-1,3,4,9-tetrahydro-β-carbolin-2-yl]-3-(3-hydroxyphenyl)propene-1-one The same method as employed in the preparation of Example 20 but starting from Intermediate 20 and (E)-3-hydroxycinnamic acid gave after recrystallization from EtOH the title compound as white crystals in a 93% yield.

MP: 251° C.

Analysis for $C_{28}H_{24}N_2O_3 \cdot 0.8H_2O$:
Calculated: C,74.58; H,5.72; N,6.21;
Found: C,74.58; H,5.65; N,6.17%.
$[\alpha]_D^{21}=-342$ (c=0.53, $CHCl_3$).

EXAMPLE 158
(E)-(R)-1-[1-(2,3-Dihydrobenzofuran-5-yl)-1,3,4,9-tetrahydro-β-carbolin-2-yl]-3-(4-(2-dimethylamino-1-methylethoxy)phenyl)propene-1-one The same method as employed in the preparation of Example 20 but starting from Intermediate 20 and Intermediate 46 gave after recrystallization from $CH_3CN$ the title compound as white crystals in a 100% yield.

MP: 193° C.

Analysis for $C_{33}H_{35}N_3O_3 \cdot 0.45H_2O$:
Calculated: C,74.82; H,6.83; N,7.93;
Found: C,74.85; H, 6.76; N,8.21%.

EXAMPLE 159
(E)-1-(1-Phenyl-1,3,4,9-tetrahydro-β-carbolin-2-yl)-3-(4-(4-methylpyperazin-1-yl)-phenyl)propene-1-one The same method as employed in the preparation of Example 20 but starting from Intermediate 1 and Intermediate 47 gave after recrystallization from EtOH the title compound as pale yellow crystals in a 26% yield.
MP: 223–226° C.
Analysis for $C_{32}H_{32}N_4O_3$. $0.4H_2O$:
Calculated: C,72.82; H,6.26; N,10.61;
Found C,72.77; H,6.31; N,10.52%.

EXAMPLE 160
(E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)phenyl)propene-1-one The same method as employed in the preparation of Example 20 but starting from Intermediate 19 and Intermediate 45 gave after recrystallization from $iPr_2O$ the title compound as white crystals in a 83% yield.
MP: 164° C.
Analysis for $C_{33}H_{33}N_3O_4$. $0.9H_2O$:
Calculated: C,71.82; H,6.36; N,7.61;
Found C,72.05; H,6.57; N,7.24%.
$[\alpha]_D^{21}=-285$ (c=0.40, $CHCl_3$).

EXAMPLE 161
(E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one The same method as employed in the preparation of Example 20 but starting from Intermediate 19 and Intermediate 46 gave after recrystallization from $iPr_2O$ the title compound as white crystals in a 56% yield.
MP: 107° C.
Analysis for $C_{32}H_{33}N_3O_4$. $0.7H_2O$:
Calculated: C,71.67; H,6.47; N,7.84;
Found: C,71.6; H, 6.53; N,7.97%.

EXAMPLE 162
(E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one The same method as employed in the preparation of Example 20 but starting from Intermediate 19 and Intermediate 48 gave after recrystallization from $iPr_2O$ the title compound as white crystals in a 78% yield.
MP: 193° C.
Analysis for $C_{32}H_{33}N_3O_4$. $1.6H_2O$:
Calculated: C,69.57; H,6.6; N,7.61;
Found: C,69.46; H, 6.59; N,7.33%.
$[\alpha]_D^{21}=-266$ (c=0.40, $CHCl_3$).

EXAMPLE 163
(E)-4-[3-Oxo-3-[1-(3,4-fluorophenyl)-1,3,4,9-tetrahydro-β-carbolin-2-yl]-propenyl]benzoic Acid, Methyl Ester The same method as employed in the preparation of Example 20 but starting from Intermediate 15 and (E)-4-(2-carboxyvinyl)benzoic acid, methyl ester gave after recrystallization from $EtOH:H_2O$ the title compound as a yellow powder in a 100% yield.
MP: 200° C.
Analysis for $C_{28}H_{22}F_2N_2O_3$:
Calculated: C,71.18; H,4.69; N,5.93;
Found: C,71.21; H,4.77; N,6.03%.

EXAMPLE 164
(E)-(R)-[1-(2,3-Dihydrobenzofuran-5-yl)-1,3,4,9-tetrahydro-β-carbolin-2-yl)]-3-(4-(2-diethylaminoethoxy)phenyl)propene-1-one The same method as employed in the preparation of Example 20 but starting from Intermediate 20 and (E)-3-(4-(2-diethylaminoethoxy)phenyl)acrylic acid (prepared according to the procedure of Sharpe, C. J.; Shabolt, R. S.; Brown, G. R.; Ashford, A.; Ross, J. W. *J. Med. Chem.* 1971, 14, 836–842), gave after recrystallization from $CH_3CN$ the title compound as white crystals in a 80% yield.
MP: 193° C.
Analysis for $C_{34}H_{37}N_3O_3$. $0.6H_2O$:
Calculated: C,74.73; H,7.05; N,7.69;
Found: C,74.53; H, 6.91; N,7.68%.
$[\alpha]_D^{20}=-311$ (c=0.30, $CHCl_3$).

EXAMPLE 165
(E)-(R)-1-[1-(2,3-Dihydrobenzofuran-5-yl)-1,3,4,9-tetrahydro-β-carbolin-2-yl)]-3-(4-(2-dimethylaminopropoxy)phenyl)propene-1-one The same method as employed in the preparation of Example 20 but starting from Intermediate 20 and Intermediate 48 gave after recrystallization from $CH_3CN$ the title compound as white crystals in a 79% yield.
MP: 193° C.
Analysis for $C_{33}H_{35}N_3O_3$:
Calculated: C,75.98; H,6.76; N,8.06;
Found: C,76.24; H, 6.76; N,8.21%.
$[\alpha]_D^{20}=-293$ (c=0.40, $CHCl_3$).

EXAMPLE 166
(E)4-[3-Oxo-3-[1-(3,4-difluorophenyl)-1,3,4,9-tetrahydro-β-carbolin-2-yl]propenyl]benzoic Acid The same method as employed in the preparation of Example 31 but starting from Example 163 gave after recrystallization from $MeOH:H_2O$ the title compound as a white powder in a 100% yield.
MP: 172° C.
Analysis for $C_{27}H_{20}F_2N_2O_3$:
Calculated: C,68.06; H,4.65; N,5.88;
Found: C,68.15; H,4.55; N,5.99%.

EXAMPLE 167
(E)-(R)-1-[1-(2,3-Dihydrobenzofuran-5-yl)-1,3,4,9-tetrahydro-β-carbolin-2-yl]-3-(4-aminophenyl)propene-1-one The same method as employed in the preparation of Example 20 but starting from Intermediate 20 and (E)-4-aminocinnamic acid gave after recrystallization from 2-propanol the title compound as white crystals in a 80% yield.
MP: 176° C.
Analysis for $C_{28}H_{25}N_3O_2$. $0.23H_2O$:
Calculated: C,76.49; H,5.84; N,9.56;
Found: C,76.21; H, 5.61; N,9.96%.
$[\alpha]_D^{21}=-375.3$ (c=0.0.35, $CHCl_3$).

EXAMPLE 168
(E)-(R)-1-[1-(3,4-Methylenedioxyphenyl)-1,3,4,9-tetrahydro-β-carbolin-2-yl]-3-(4-aminophenyl)propene-1-one The same method as employed in the preparation of Example 20 but starting from Intermediate 19 and (E)-4-aminocinnamic acid gave after recrystallization from 2-propanol:$H_2O$ the title compound as white crystals in a 63% yield.
MP: 264° C.
Analysis for $C_{27}H_{23}N_3O_3$. $0.6H_2O$:
Calculated: C,72.34; H,5.44; N,9.37;
Found: C,72.06; H,5.48; 9.55%.
$[\alpha]_D^{21}=-266$ (c=0.3, MeOH).

EXAMPLE 169
(R)-(E)-1-[1-(3,4-Methylenedioxyphenyl)-1,3,4,9-tetrahydro-β-carbolin-2-yl)]-3-(4-(2-pyrrolidin-1-ylethoxy)phenyl)propene-1-one The same method as employed in the preparation of Example 20 but starting from Intermediate 19 and Intermediate 42 gave after recrystallization from iPr$_2$O the title compound as brown crystals in a 4% yield.
MP: 116° C.
Analysis for $C_{33}H_{33}N_3O_4 \cdot 1.7H_2O$:
Calculated: C,69.99; H,6.48; N,7.42;
Found: C,70.02; H, 6.47; N,7.59%.

EXAMPLE 170
(E)-(R)-1-[1-(3,4-Methylenedioxyphenyl)-1,3,4,9-tetrahydro-β-carbolin-2-yl)]-3-(4-(2-diethylaminoethoxy)phenylpropene-1-one The same method as employed in the preparation of Example 20 but starting from 1 Intermediate 19 and (E)-3-(4-(2-diethylaminoethoxy)phenyl)acrylic acid (prepared according to the procedure of Sharpe, C. J.; Shabolt, R. S.; Brown, G. R.; Ashford, A.; Ross, J. W. *J. Med. Chem.* 1971, 14(9), 836–842) gave after recrystallization from iPr$_2$O the title compound as white crystals in a 67% yield.
MP: 94° C.
Analysis for $C_{33}H_{35}N_3O_4 \cdot 0.5H_2O$:
Calculated: C,72.5; H,6.64; N,7.69;
Found: C,72.48; H,6.64; N,7.58%.
$[\alpha]_D^{21} = -287$ (c=0.3, CHCl$_3$).

EXAMPLE 171
(E)-1-[1-(3-Fluoro-4-methoxyphenyl)-1,3,4,9-tetrahydro-β-carbolin-2-yl)]-3-(3-nitrophenyl)propene-1-one The same method as employed in the preparation of Example 20 but starting from Intermediate 14 and (E)-3-nitrocinnamic acid gave after recrystallization from DCM:2-propanol the title compound as a yellow powder in a 90% yield.
MP: 141° C.
Analysis for $C_{27}H_{22}FN_3O_4 \cdot 0.9CH_2Cl_2$:
Calculated: C,61.16; H,4.38; N,7.67;
Found: C,61.1; H,4.39; N,7.56%.

EXAMPLE 172
(E)-(R)-1-[1-(2,3-Dihydrobenzofuran-5-yl)-1,3,4,9-tetrahydro-β-carbolin-2-yl]-3-(4-trifluoromethylphenyl)propene-1-one The same method as employed in the preparation of Example 20 but starting from Intermediate 20 and (E)-4-trifluoromethylcinnamic acid gave after recrystallization from 2-propanol the title compound as white crystals in a 91% yield.
MP: 141° C.
Analysis for $C_{29}H_{23}F_3N_2O_2$:
Calculated: C,71.3; H,4.75; N,5.73;
Found: C,71.37; H,4.79; N,5.86%.
$[\alpha]_D^{20} = -326$ (c=0.3, CHCl$_3$).

EXAMPLE 173
(E)-(R)-1-[1-(2,3-Dihydrobenzofuran-5-yl)-1,3,4,9-tetrahydro-β-carbolin-2-yl]-3-(3-trifluoromethylphenyl)propene-1-one The same method as employed in the preparation of Example 20 but starting from Intermediate 20 and (E)-3-trifluoromethylcinnamic acid gave after recrystallization from 2-propanol:H$_2$O the title compound as white crystals in a 80% yield.
MP: 223° C.
Analysis for $C_{29}H_{23}F_3N_2O_2$:
Calculated: C,71.3; H,4.75; N,5.73;
Found: C,71.44, H,4.73; N,5.85%.
$[\alpha]_D^{20} = -326$ (c=0.3, CHCl$_3$).

EXAMPLE 174
(E)-(R)-1-[1-(2,3-Dihydrobenzofuran-5-yl)-1,3,4,9-tetrahydro-β-carbolin-2-yl]-3-(4-(2-morpholin-4-ylethoxy)phenyl)propene-1-one The same method as employed in the preparation of Example 20 but starting from Intermediate 20 and Intermediate 49 gave after recrystallization from 2-propanol:H$_2$O the title compound as white crystals in a 66% yield.
MP: 148° C.
Analysis for $C_{34}H_{35}N_3O_4$:
Calculated, C,71.3; H,4.75; N,5.73;
Found: C,71.44; H,4.73; N,5.85%.
$[\alpha]_D^{19} = -288$ (c=0.3, CHCl$_3$).

EXAMPLE 175
(E)-(R)-1-[1-(2,3-Dihydrobenzofuran-5-yl)-1,3,4,9-tetrahydro-β-carbolin-2-yl]-3-(4-(2-(ethylmethylamino)ethoxy)phenyl)propene-1-one The same method as employed in the preparation of Example 20 but starting from Intermediate 20 and Intermediate 50 gave after recrystallization from iPr$_2$O the title compound as a white powder in a 66% yield.
MP: 107° C.
Analysis for $C_{33}H_{35}N_3O_3 \cdot 0.8H_2O$:
Calculated: C,73.94; H,6.88; N,7.84;
Found: C,74.09; H,7.15; N,7.48%.
$[\alpha]_D^{21} = -253$ (c=0.3, CHCl$_3$).

EXAMPLE 176
(E)-1-[1-(2,3-Dihydrobenzofuran-5-yl)-1,3,4,9-tetrahydro-β-carbolin-2-yl]-3-(4-(3-(dimethylamino)propenyl)phenyl)propene-1-one The same method as employed in the preparation of Example 20 but starting from Intermediate 20 and Intermediate 51 gave after recrystallization from EtOH the title compound as a white powder in a 45% yield.
MP: 216° C.
Analysis for $C_{33}H_{33}N_3O_2 \cdot 0.2H_2O$:
Calculated: C,78.14; H,6.88; N,7.84;
Found: C,78.03; H,6.74; N,8.21%.
$[\alpha]_D^{19.8} = -312$ (c=0.29, CHCl$_3$).

EXAMPLE 177
(E)-(R)-1-[1-(2,3-Dihydrobenzofuran-5-yl)-1,3,4,9-tetrahydro-β-carbolin-2-yl]-3-(4-(3-dimethylamino-2-hydroxypropoxy)phenyl)propene-1-one At 0° C. to a solution (E)-(R)-1-[1-(2,3-dihydrobenzofuran-5-yl)-1,3,4,9-tetrahydro-β-carbolin-2-yl]-3-(4-(2-(tertbutyldimethylsilanyloxy)-3-dimethylamino-2-hydroxy-propoxy)phenyl)propene-1-one (0.4 g, 0.6 mmol) in 50 mL of anhydrous THF was added tetrabutylammonium fluoride (0.6 mL, 1 equiv., 1 M in THF). The resulting mixture was stirred at rt for one day. Quenching with water, extraction with DCM, washing with brine, drying over MgSO$_4$ and concentration in vacuo gave an oil. Recrystallization from iPrOH:H$_2$O gave the title compound (0.2 g, 62%) as an off-white powder.
MP: 138° C.
Analysis for $C_{33}H_{35}N_3O_4 \cdot 0.5H_2O$:
Calculated: C,72.5; H,6.64; N,7.69;
Found; C,72.21; H,6.75; N,7.48%.
$[\alpha]_D^{20} = -283$ (c=0.6, CHCl$_3$).
(E)-(R)-1-[1-(2,3-Dihydrobenzofuran-5-yl)-1,3,4,9-tetrahydro-β-carbolin-2-yl]-3-(4-(2-(tertbutyldimethylsilanyloxy)-3-dimethylamino-2-hydroxypropoxy)phenyl)-propene-1-one was obtained in a 89% yield as a yellow oil from the same method as employed in the preparation of Example 20 but starting from Intermediate 20 and Intermediate 52.

$^1$H NMR (CDCl$_3$,250 MHz) δ8.1 (s, 1H), 7.5–7.3 (m, 2H), 6.9–7.2 (m, 7H), 6.8–6.5 (m, 3H), 4.5 (t, 2H), 4.2 (m, 1H), 4.0 (m, 3H), 3.8 (m, 1H) 3.3 (m, 1H), 3.0 (t, 2H), 2.7–2.9 (m, 3H), 2.3–2.15 (m, 2H), 2.1 (s, 6H), 0.8 (s,9H), 0.05 (d, 6H).

EXAMPLE 178

(E)-(R)-1-(1-(2,3-Dihydrobenzofuran-5-yl)-1,3,4,9-tetrahydro-β-carbolin-2-yl)-3-(4-formylphenyl)propene-1-one The same method as employed in the preparation of Example 20 but starting from Intermediate 20 and (E)-4-formylcinnamic acid gave after recrystallization from EtOH the title compound as a white powder in a 53% yield.

MP: 175° C.
Analysis for C$_{29}$H$_{24}$N$_2$O$_3$. 0.8H$_2$O:
Calculated: C,75.24; H,5.57; N,6.05;
Found: C,75.54; H,5.78; N,6.11%.
[α]$_D^{20}$=−340 (c=0.33, CHCl$_3$).

EXAMPLE 179

(E)-(R)-1-[1-(2,3-Dihydrobenzofuran-5-yl)-1,3,4,9-tetrahydro-β-carbolin-2-yl]-3-(4-propylaminomethyl)phenyl)propene-1-one To a solution of a solution of Example 178 (0.5 g, 1.1 mmol) in 50 mL of MeOH was added propylamine (14 mL, 1.5 equiv.). The resulting mixture was stirred at 50° C. for 4 hours. At rt polymer-supported borohydride (1.2 g, 1.2 equiv., 2.5 mmol/g) was added and the resulting mixture was stirred at 50° C. for 6 hours. After evaporation in vacuo, the residue was washed with 2×50 mL of DCM. After filtration, the filtrate was washed with 2×50 mL of water. Drying over Na$_2$SO$_4$, evaporation in vacuo and recrystallization from MeOH gave the title compound (0.4 g, 81%) as a pale yellow powder.

MP: 170° C.
Analysis for C$_{32}$H$_{33}$N$_3$O$_2$. 0.4H$_2$O:
Calculated: C,77.05; H,6.83; N,8.42;
Found: C,77.04; H,6.78; N,8.29%.
[α]$_D^{19}$=−330 (c=0.4, MeOH).

EXAMPLE 180

(E)-(R)-1-[1-(2,3-Dihydrobenzofuran-5-yl)-1,3,4,9-tetrahydro-β-carbolin-2-yl]-3-[4-(2-dimethylaminoethylamino)phenylpropene-1-one The same method as employed in the preparation of Example 20 but starting from intermediate 20 and Intermediate 53 gave after recrystallization from EtOH the title compound as yellow crystals in a 12% yield.

MP: 160° C.
Analysis for C$_{32}$H$_{34}$N$_4$O$_2$. 0.2H$_2$O:
Calculated: C,75.33; H,6.8; N,10.98;
Found C,75.06; H,6.83; N,10.98%.
[α]$_D^{20}$=−214 (c=0.1, MeOH).

EXAMPLE 181

(E)-(R)-1-[1-(2,3-Dihydrobenzofuran-5-yl)-1,3,4,9-tetrahydro-β-carbolin-2-yl]-3-(4-(2-aminoethoxy)phenyl)propene-1-one To a solution of (E)-(R)-2-[2-(4-{3-[1-(2,3-dihydrobenzofuran-5-yl)-1,3,4,9-tetrahydro-β-carbolin-2-yl]-3-oxo-propenyl}-phenoxy)ethyl]isoindole-1,3-dione (0.85 g, 1.4 mmol) in 50 mL of MeOH:THF was added hydrazine (0.38 mL, 3 equiv., 35% in water). The resulting mixture was stirred at 45° C. for 4 hours. Evaporation in vacuo and flash chromatography with DCM:MeOH (80:20) as eluting solvent gave the title compound (0.17 g, 26%) as yellow powder.

MP: 186° C.
Analysis for C$_{30}$H$_{29}$N$_3$O$_3$. 0.3CH$_2$Cl$_2$:
Calculated: C,72.06; H,5.91; N,8.32;
Found C,72.12; H,8.08; N,8.67%.
[α]$_D^{20}$=−285 (c=0.29, MeOH).

(E)-(R)-2-[2-(4-{3-[1-(2,3-Dihydrobenzofuran-5-yl)-1,3,4,9-tetrahydro-β-carbolin-2-yl]-3-oxo-propenyl}phenoxy)ethyl]isoindole-1,3-dione was obtained after recrystallization from EtOH, as a gummy solid in a 90% yield using the same method as employed in the preparation of Example 20 but starting from Intermediate 20 and Intermediate 54.

$^1$H NMR (CDCl$_3$ 250 MHz) δ8.0–6.7 (m, 19H), 4.5 (t, 2H), 4.2–4.0 (m, 5H), 3.4 (m, 1H), 3.0 (t, 2H), 2.9 (m, 2H).

EXAMPLE 182

(E)-(R)-1-[1-(2,3-Dihydrobenzofuran-5-yl)-1,3,4,9-tetrahydro-β-carbolin-2-yl]-3-(4-hydroxyphenyl)propene-1-one The same method as employed in the preparation of Example 20 but starting from Intermediate 20 and (E)-4-hydroxycinnamic acid gave after recrystallization from DMF:MeOH the title compound as a white powder in a 90% yield.

MP: 189° C.
Analysis for C$_{28}$H$_{24}$N$_2$O$_3$. 0.5DMF:
Calculated: C,75.51; H,5.77; N,7.12;
Found: C,75.31; H,5.84; N,6.81%.
[α]$_D^{20}$=−310 (c=0.32, MeOH).

EXAMPLE 183

(E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one The same method as employed in the preparation of Example 20 but starting from Intermediate 20 and Intermediate 47 gave after recrystallization from DMF:EtOH the title compound as pale yellow crystals in a 48% yield.

MP: 193° C.
Analysis for C$_{33}$H$_{34}$N$_4$O$_2$. 1.0DMF:
Calculated: C,73.07; H,6.98; N,11.83;
Found C,72.67; H,7.05; N,11.55%.
[α]$_D^{20}$=−330 (c=0.3, CHCl$_3$).

EXAMPLE 184

(E)-(R)-1-[1-(2,3-Dihydrobenzofuran-5-yl)-1,3,4,9-tetrahydro-β-carbolin-2-yl]-3-(4-methylaminomethyl)phenyl)propene-1-one The same method as employed in the preparation of Example 179 but starting from methylamine gave after recrystallization from MeOH.H$_2$O the title compound as a white powder in a 52% yield.

MP: 129° C.
Analysis for C$_{30}$H$_{29}$N$_3$O$_2$. 1.1H$_2$O:
Calculated: C,74.54; H,6.51; N,8.69;
Found: C,74.68; H,6.57; N,8.59%.
[α]$_D^{21}$=−288 (c=0.4, CHCl$_3$).

EXAMPLE 185

(E)-(R)-1-[1-(2,3-Dihydrobenzofuran-5-yl)-1,3,4,9-tetrahydro-β-carbolin-2-yl]-3-(4-isopropylaminomethyl)phenyl)propene-1-one The same method as employed in the preparation of Example 179 but starting from isopropylamine gave after recrystallization from MeOH:H$_2$O the title compound as a white powder in a 47% yield.

MP: 158° C.
Analysis for C$_{32}$H$_{33}$N$_3$O$_2$. 0.3H$_2$O:

Calculated: C,77.33; H,6.81; N,8.45;
Found: C,77.42; H,6.74; N,8.26%.
$[\alpha]_D^{21}$=−319 (c=0.3, MeOH).

EXAMPLE 186
(E)-(R)-1-[1-(2,3-Dihydrobenzofuran-5-yl)-1,3,4,9-tetrahydro-β-carbolin-2-yl]-3-(4-dimethylaminomethyl) phenyl)propene-1-one The same method as employed in the preparation of Example 179 but using dimethylamine gave after recrystallization from iPrOH:H$_2$O the title compound as a white powder in a 34% yield.

MP: 153–154° C.
Analysis for $C_{31}H_{31}N_3O_2.0.2H_2O$:
Calculated: C,77.38; H,6.58; N,8.73;
Found: C,77.4; H,6.49; N,8.61%.
$[\alpha]_D^{21}$=−336 (c=0.3, MeOH).

EXAMPLE 187
(E)-(R)-1-[1-(2,3-Dihydrobenzofuran-5-yl)-1,3,4,9-tetrahydro-β-carbolin-2-yl]-3-[4-(3-dimethylaminopropoxy)phenyl]propene-1-one The same method as employed in the preparation of Example 79 but starting from Example 182 and dimethylaminopropyl chloride gave after recrystallization from CH$_3$CN the title compound as a white powder in a 53% yield.

MP: 186° C.
Analysis for $C_{33}H_{35}N_3O_2$. 0.6H$_2$O:
Calculated: C,74.44; H,6.85; N,7.89;
Found: C,74.36; H,6.63; N,7.98%.
$[\alpha]_D^{20}$=−326 (c=0.3, MeOH).

EXAMPLE 188
(E)-(R)-1-[1-(2,3-Dihydrobenzofuran-5-yl)-1,3,4,9-tetrahydro-β-carbolin-2-yl]-3-(4-(2-piperidin-1-ylethoxy) phenyl)propene-1-one The same method as employed in the preparation of Example 20 but starting from Intermediate 20 and Intermediate 55 gave after recrystallization from CH$_3$CN the title compound as white crystals in a 50% yield.

MP: 210° C.
Analysis for $C_{35}H_{37}N_3O_3$:
Calculated: C,76.75; H,6.81; N,7.67;
Found: C,76.68; H,7.11; N,7.93%.
$[\alpha]_D^{18.9}$=−290 (c=0.4, CHCl$_3$).

EXAMPLE 189
(E)-1-[1-(3,4-Methylenedioxyphenyl)-1,3,4,9-tetrahydro-β-carbolin-2-yl]-3-(4-(2-piperidin-1-ylethoxy)phenyl] propene-1-one The same method as employed in the preparation of Example 20 but starting from Intermediate 55 gave after recrystallization from MeOH:H$_2$O the title compound as a beige solid in a 32% yield.

MP: 102° C.
Analysis for $C_{34}H_{35}N_3O_4$. 0.6MeOH:
Calculated: C,73.05; H,6.63; N,7.39;
Found: C,73.24; H,6.87; N,7.02%.

EXAMPLE 190
(E)-(R)-[2-(4-{3-[1-(2,3-Dihydrobenzofuran-5-yl)-1,3,4,9-tetrahydro-β-carbolin-2-yl]-3-oxopropenyl}phenoxy)ethyl] methylcarbamic Acid, Tertbutyl Ester The same method as employed in the preparation of Example 20 but starting from Intermediate 20 and Intermediate 56 gave the title compound as a yellow powder in a 95% yield.

MP: 110° C.
Analysis for $C_{36}H_{39}N_3O_5$. 0.3H$_2$O:
Calculated: C,72.17; H,6.66; N,7.01;
Found; C,71.9; H,6.86; N,7.17%.

EXAMPLE 191
(E)-(R)-1-[1-(2,3-Dihydrobenzofuran-5-yl)-1,3,4,9-tetrahydro-β-carbolin-2-yl]-3-[4-(2-methylaminoethoxy) phenyl]propene-1-one A solution of Example 190 (0.33 g, 0.55 mmol) in DCM (30 mL) was treated with zinc bromide (0.63 g, 5 equiv.) for 16 hours at 30° C. A gummy solid was formed. Extraction with DCM:MeOH, washing with water, drying over Na$_2$SO$_4$ and recrystallization from iPrOH gave the title compound as white crystals in a 98% yield.

MP: 145° C.
Analysis for $C_{31}H_{31}N_3O_3$. 0.2H$_2$O:
Calculated: C,74.89; H,6.37; N,8.45;
Found: C,74.90; H,6.70; N,8.49%.
$[\alpha]_D^{20}$=−337 (c=0.4, MeOH).

EXAMPLE 192
(E)-1-[1-(3,4-Methylenedioxyphenyl)-1,3,4,9-tetrahydro-β-carbolin-2-yl]-3-(4-(2-piperidin-1-ylethoxy)phenyl] propene-1-one The same method as employed in the preparation of Example 1 but starting from Intermediate 13 gave after recrystallization from MeOH:H$_2$O the title compound as a beige solid in a 32% yield.

MP: 102° C.
Analysis for $C_{34}H_{35}N_3O_4$. 0.6MeOH:
Calculated: C,73.05; H,6.63; N,7.39;
Found: C,73.24; H,6.87; N,7.02%.

Inhibitory Effect on cGMP-PDE cGMP-PDE activity of compounds of the present invention was measured using a one-step assay adapted from Wells at al. (Wells, J. N., Baird, C. E., Wu, Y. J. and Hardman, J. G., Biochim. Biophys. Acta 384, 430 (1975)). The reaction medium contained 50 mM Tris-HCl,pH 7.5, 5 mM Mg-acetate, 250 μg/ml 5'-Nucleotidase, 1 mM EGTA and 0.15 μM 8-[H$^3$]-cGMP. The enzyme used was a human recombinant PDE 5 (ICOS, Seattle USA).

Compounds of the invention were dissolved in DMSO finally present at 2% in the assay. The incubation time was 30 minutes during which the total substrate conversion did not exceed 30%.

The IC$_{50}$ values for the compounds examined were determined from concentration-response curves using typically concentrations ranging from 10 nM to 10 μM. Tests against other PDE enzymes using standard methodology also showed that compounds of the invention are highly selective for the cGMP specific PDE enzyme.

cGMP Level Measurements

Rat aortic smooth muscle cells (RSMC) prepared according to Chamley et al. in Cell Tissue Res 177, 503–522 (1977) were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn and two extractions were performed by addition of 65% ethanol (0.25 ml). The two ethanolic extracts were pooled and evaporated until dryness, using a Speed-vac system. cGMP was measured after acetylation by scintillation proximity immunoassay (AMERSHAM). The EC$_{50}$ values are expressed as the dose giving half of the stimulation at saturating concentrations Biological Data The compounds according to the present invention were typically found to exhibit an $IC_{50}$ value of less than 500 nM and an $EC_{50}$ value of less than 5 μM. In vitro test data for representative compounds of the invention is given in the following table:

TABLE 1

In vitro results

| Example No. | $IC_{50}$ nM | $EC_{50}$ μM |
|---|---|---|
| 14 | 5 | 0.45 |
| 25 | 72 | 0.3 |
| 28 | 55 | 0.3 |
| 31 | 4 | 1 |
| 55 | 40 | 0.4 |
| 61 | 20 | 1.8 |
| 140 | 2 | 0.1 |
| 142 | 18 | 1.5 |
| 156 | 15 | <1 |
| 164 | 11 | 1.5 |
| 165 | 9 | <1 |
| 177 | 12 | <1 |
| 184 | 44 | 3 |
| 180 | 25 | 3.5 |
| 181 | 9 | 2 |
| 183 | 24 | 2 |
| 182 | 2 | <1 |
| 188 | 24 | <1 |
| 191 | 8 | <1 |

The hypotensive effects of compounds according to the invention as identified in Table 2 were studied in conscious spontaneously hypertensive rats (SHR). The compounds were administered orally at a dose of 5 mg/kg in a mixture of 5% DMF and 95% olive oil. Blood pressure was measured from a catheter inserted in the carotid artery and recorded for 5 hours after administration. The results are expressed as Area Under the Curve (AUC from 0 to 5 hours, mmHg.hour) of the fall in blood pressure over time.

TABLE 1

In vivo results

| Example No. | AUC PO (mmHg · h) |
|---|---|
| 14 | 128 |
| 25 | 72 |
| 26 | 102 |
| 28 | 114 |
| 31 | 86 |
| 55 | 97 |
| 61 | 95 |
| 112 | 71 |
| 122 | 76 |
| 140 | 105 |
| 142 | 74 |
| 156 | 57 |
| 175 | 52 |
| 177 | 100 |
| 181 | 77 |
| 188 | 86 |
| 191 | 84 |

The application of which this description and claims forms part may be used as a basis for priority in respect of any subsequent application. The claims of such subsequent application may be directed to any novel feature or combination of features described herein. They may take the form of product, composition, process or use claims and may include, by way of example and without limitation, the following claim:

What is claimed is:
1. A compound of formula (I)

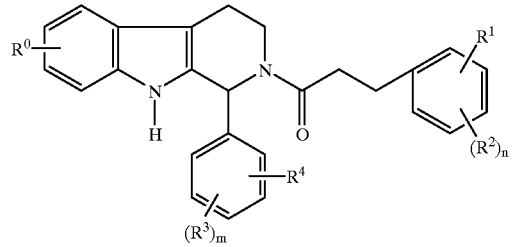

wherein
$R^0$ represents -hydrogen or -halogen;
$R^1$ is selected from the group consisting of:
- -hydrogen,
- $-NO_2$,
- -trifluoromethyl,
- -trifluoromethoxy,
- -halogen,
- -cyano,
- a 5- or 6-membered heterocyclic group selected from the group consisting of pyridyl, pyrrolidinyl, morpholinyl, tetrahydrofuryl, furyl, tetrazolyl, imidazolyl, piperidinyl, and piperizinyl (optionally substituted by $-C(=O)OR^a$ or $C_{1-4}$alkyl),
- $-C_{1-6}$alkyl optionally substituted by $OR^a$,
- $-C_{1-3}$alkoxy,
- $-C(=O)R^a$,
- $-O-C(=O)R^a$,
- $-C(=O)OR^a$,
- $-C_{1-4}$alkyleneC$(=O)OR^a$,
- $-O-C_{1-4}$alkylene-C$(=O)OR^a$,
- $-C_{1-4}$alkylene-O-$C_{1-4}$alkylene-C$(=O)OR^a$,
- $-C(=O)NR^aCO_2R^c$,
- $-C(=O)C_{1-4}$alkyleneHet, wherein Het represents 5- or 6-membered heterocyclic group as defined above,
- $-C_{1-4}$alkyleneNR$^aR^b$,
- $-C_{2-6}$alkenyleneNR$^aR^b$,
- $-C(=O)NR^aR^b$,
- $-C(=O)NR^aR^c$,
- $-C(=O)NR^aC_{1-4}$alkyleneOR$^b$,
- $-C(=O)NR^aC_{1-4}$alkyleneHet, wherein Het represents a 5- or 6-membered heterocyclic group as defined above,
- $-OR^a$,
- $-OC_{2-4}$alkyleneNR$^aR^b$,
- $-OC_{1-4}$alkylene-CH(OR$^a$)CH$_2$NR$^aR^b$,
- $-O-C_{1-4}$alkyleneHet, wherein Het represents a 5- or 6-membered heterocyclic group as defined above,
- $-O-C_{2-4}$alkylene-OR$^a$,
- $-O-C_{2-4}$alkylene-NR$^a$—C$(=O)$—OR$^b$,
- $-NR^aR^b$,
- $-NR^aC_{1-4}$alkyleneNR$^aR^b$,
- $-NR^aC(=O)R^b$,
- $-NR^aC(=O)NR^aR^b$,
- $-N(SO_2C_{1-4}$alkyl)$_2$,
- $-NR^a(SO_2C_{1-4}$alkyl),
- $-SO_2NR^aR^b$, and
- $-OSO_2$trifluoromethyl;
$R^2$ is selected from the group consisting of:
- -hydrogen,
- -halogen,
- $-OR^a$,
- $-C_{1-6}$alkyl, —NO₂, and
—NR^aR^b, or R¹ and R², together form a 3- or 4-membered alkylene or alkenylene chain, optionally containing at least one heteroatom;

a first R³ is selected from the group consisting of:
-hydrogen,
-halogen,
—NO₂,
-trifluoromethoxy,
—C₁₋₆alkyl, and
—C(=O)OR^a, and a second R³ and R⁴ together, and with the phenyl ring to which they are attached, form a 3- or 4-membered alkylene or alkenylene chain, optionally containing at least one heteroatom, R^a and R^b, which may be the same or different, are independently selected from hydrogen and C₁₋₆alkyl;

R^c represents phenyl or C₄₋₆cycloalkyl, which phenyl or C₄₋₆cycloalkyl can be optionally substituted by one or more halogen atoms, one or more —C(=O)OR^a or one or more —OR^a;

n is an integer selected from 1, 2 and 3;
m is an integer selected from 1 and 2;
and pharmaceutically acceptable salts and solvates thereof.

2. A compound represented by formula Ia

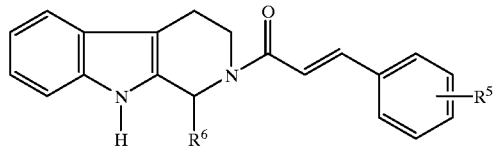

(Ia)

wherein
R⁵ is selected from the group consisting of —OH, —OC₂₋₄alkyleneNR^aR^b and —O—C₁₋₄alkyleneHet, wherein Het represents a 5- or 6-membered heterocyclic group selected from the group consisting of pyridyl, pyrrolidinyl, morpholinyl, tetrahydrofuryl, furyl, tetrazolyl, imidazolyl, piperidinyl, and piperizinyl, optionally substituted by C₁₋₄alkyl;

R⁶ represents

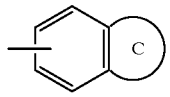

wherein C represents a 5- or 6-membered ring which may be saturated or partially or fully unsaturated and comprises carbon atoms and optionally one or two heteroatoms selected from oxygen, sulphur, and nitrogen, optionally substituted by C₁₋₄alkyl;

R^a and R^b, which may be the same or different, are independently selected from hydrogen and C₁₋₆alkyl;
and pharmaceutically acceptable salts and solvates thereof.

3. The compound of claim 1 wherein R⁰ represents hydrogen.

4. The compound of claim 1 wherein R¹ is selected from the group consisting of:
—OR^a,
—O—C₂₋₄alkylene NR^aR^b,
—O—C₁₋₄alkyleneHet, and
—O—C₂₋₄alkylene-OR^a.

5. The compound of claim 4 wherein R¹ represents —O—C₁₋₄ethyleneNR^aR^b.

6. The compound of claim 5 wherein at least one of R^a and R^b is methyl.

7. The compound of claim 1 wherein R² represents hydrogen.

8. The compound of claim 1 wherein R¹ and R² together form a methylenedioxy chain, an ethyleneoxy chain, an ethylenedioxy chain, an ethenyleneoxy chain, a propylene chain, a butylene chain, or —NR^aethylene-O—.

9. The compound of claim 1 wherein R¹ and R² together form methylenedioxy, propylene, or —N(CH₃)—ethylene-O—.

10. The compound of claim 1 wherein R³ and R⁴ together form a methylenedioxy chain, an ethylenoxy chain, an ethylenedioxy chain, an ethenyleneoxy chain, a propylene chain, a propylene chain, a butylene chain, or —NR^aethylene-O—.

11. The compound of claim 1 wherein R³ and R⁴ together form a methylenedioxy or ethyleneoxy.

12. The compound of claim 2 wherein R¹ represents —OC₂₋₄alkyleneNR^aR^b, or —O—C₁₋₄alkyleneHet.

13. The compound of claim 2 wherein R² represents

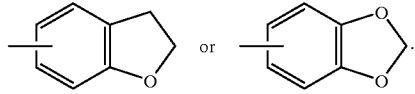

14. A compound selected from the group consisting of
(E)-1-(1-Phenyl-1,3,4,9-tetrahydro-β-carbolin-2-yl)-3-phenylpropene-1-one,
(E)-1-(1-Phenyl-1,3,4,9-tetrahydro-β-carbolin-2-yl)-3-(4-nitrophenyl)propene-1-one,
(E)-1-(1-Phenyl-1,3,4,9-tetrahydro-β-carbolin-2-yl)-3-(4-trifluoromethylphenyl)propene-1-one,
(E)-1-(1-Phenyl-1,3,4,9-tetrahydro-β-carbolin-2-yl)-3-(4-methoxyphenyl)propene-1-one,
(E)-1-[1-(4-Methoxyphenyl)-1,3,4,9-tetrahydro-β-carbolin-2-yl]-3-(4-trifluoromethylphenyl)propene-1-one,
(E)-N-[4-[3-Oxo-3-(1-phenyl-1,3,4,9-tetrahydro-β-carbolin-2-yl)propenyl]phenyl]acetamide
(E)-1-[1-(4-Methoxyphenyl)-1,3,4,9-tetrahydro-β-carbolin-2-yl]-3-phenylpropene-1-one,
(E)-1-(1-Phenyl-1,3,4,9-tetrahydro-β-carbolin-2-yl)-3-(4-formylphenyl)propene-1-one,
(E)-N-[4-[3-Oxo-3-(1-(4-nitrophenyl)-1,3,4,9-tetrahydro-β-carbolin-2-yl)propenyl]phenyl]acetamide
(E)-1-[1-(4-Nitrophenyl)-1,3,4,9-tetrahydro-β-carbolin-2-yl]-3-phenylpropene-1-one,
(E)-1-[1-(4-Trifluoromethoxyphenyl)-1,3,4,9-tetrahydro-β-carbolin-2-yl]-3-phenylpropene-1-one,
(E)-1-[1-(4-Methylphenyl)-1,3,4,9-tetrahydro-β-carbolin-2-yl]-3-phenylpropene-1-one,
(E)-4-[3-Oxo-3-(1-phenyl-1,3,4,9-tetrahydro-β-carbolin-2-yl)-propenyl]benzoic acid, methyl ester,
(E)-1-[1-(2-Chlorophenyl)-1,3,4,9-tetrahydro-β-carbolin-2-yl]-3-phenylpropene-1-one,
(E)-1-(1-Phenyl-1,3,4,9-tetrahydro-β-carbolin-2-yl)-3-(3,4-methylenedioxyphenyl)-propene-1-one,
(E)-1-[1-(4-Chlorophenyl)-1,3,4,9-tetrahydro-β-carbolin-2-yl]-3-phenylpropene-1-one,
(E)-N-(2-Morpholin-4-ylethyl)-4-[3-oxo-3-(1-(3,4-methylene-dioxyphenyl)-1,3,4,9-tetrahydro-β-carbolin-2-yl)propenyl]benzamide,
(E)-N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide, (E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide, (E)-N-(2-Piperazin-1-ylethyl)-3-[3-oxo-3-(1-(3,4-methylene-dioxyphenyl)-1,3,4,9-tetrahydro-β-carbolin-2-yl)propenyl]benzamide, (E)-N-(1-Ethylpyrrolidin-2-yl-methyl)-3-[3-oxo-3-(1-(3,4-methylenedioxyphenyl)-1,3,4,9-tetrahydro-β-carbolin-2-yl)propenyl]benzamide, (E)-1-[1-(4-Isopropylphenyl)-1,3,4,9-tetrahydro-β-carbolin-2-yl]-3-(3-nitrophenyl)propene-1-one, (E)-1-[1-(4-Methoxyphenyl)-1,3,4,9-tetrahydro-β-carbolin-2-yl]-3(3-nitrophenyl)propene-1-one, (E)-1-[1-(4-Methylphenyl)-1,3,4,9-tetrahydro-β-carbolin-2-yl]-3-(2-chloro-5-nitrophenyl)propene-1-one, (E)-1-[1-(Indan-5-yl)-1,3,4,9-tetrahydro-β-carbolin-2-yl]-3-phenylpropene-1-one, (E)-4-[3-Oxo-3-[1-(4-methoxyphenyl)-1,3,4,9-tetra-hydro-β-carbolin-2-yl]propenyl]benzoic acid, methyl ester, (E)-4-[3-Oxo-3-[1-(4-methoxyphenyl)-1,3,4,9-tetra-hydro-β-carbolin-2-yl]propenyl]benzoic acid, (E)-1-[1-(3-Fluoro-4-methoxyphenyl)-1,3,4,9-tetra-hydro-β-carbolin-2-yl]-3-phenylpropene-1-one, (E)-1-[1-(3,4-Methylenedioxyphenyl)-1,3,4,9-tetra-hydro-β-carbolin-2-yl]-3-[4-pyrrolidin-1-ylphenyl]-propene-1-one, (E)-1-[1-(3,4-Methylenedioxyphenyl)-1,3,4,9-tetra-hydro-β-carbolin-2-yl]-3-[4-imidazol-1-ylphenyl]-propene-1-one, (E)-1-[1-(3-Fluoro-4-methoxyphenyl)-1,3,4,9-tetra-hydro-β-carbolin-2-yl)]-3-(4-(2-dimethylaminoethoxy)phenyl)propene-1-one, (E)-(R)-1-[1-(2,3-Dihydrobenzofuran-5-yl)-1,3,4,9-tetrahydro-β-carbolin-2-yl)]-3-(4-(1-(S)-methylpyrrolidin-2-yl-methoxy)phenyl)propene-1-one, (E)-1-(1-Phenyl-1,3,4,9-tetrahydro-β-carbolin-2-yl)-3-(4-(4-methylpyperazin-1-yl)-phenyl)propene-1-one, (E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)-phenyl)propene-1-one, (E)-4-[3-Oxo-3-[1-(3,4-fluorophenyl)-1,3,4,9-tetra-hydro-β-carbolin-2-yl]propenyl]benzoic acid, methyl ester, (E)-4-[3-Oxo-3-[1-(3,4-difluorophenyl)-1,3,4,9-tetrahydro-β-carbolin-2-yl]propenyl]benzoic acid, (E)-(R)-1-[1-(3,4-Methylenedioxyphenyl)-1,3,4,9-tetrahydro-β-carbolin-2-yl)]-3-(4-(2-pyrrolidin-1-ylethoxy)phenyl)propene-1-one, (E)-1-[1-(3-Fluoro-4-methoxyphenyl)-1,3,4,9-tetra-hydro-β-carbolin-2-yl)]-3-(3-nitrophenyl)propene-1-one, (E)-(R)-1-[1-(2,3-Dihydrobenzofuran-5-yl)-1,3,4,9-tetrahydro-β-carbolin-2-yl]-3-(4-(2-morpholin-4-ylethoxy)phenyl)propene-1-one, (E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one, (E)-(R)-1-[1-(2,3-Dihydrobenzofuran-5-yl)-1,3,4,9-tetrahydro-β-carbolin-2-yl]-3-(4-(2-piperidin-1-ylethoxy)phenyl)propene-1-one, (E)-1-[1-(3,4-Methylenedioxyphenyl)-1,3,4,9-tetra-hydro-β-carbolin-2-yl)-3-(4-(2-piperidin-1-ylethoxy)phenyl]propene-1-one, and pharmaceutically acceptable salts and solvates thereof.

15. A pharmaceutical composition comprising a compound of claim 1, together with a pharmaceutically acceptable diluent or carrier.

16. A method for the curative or prophylactic treatment of erectile dysfunction in an animal comprising administration of an effective dose of a compound of claim 1, or pharmaceutically acceptable salts and solvates thereof, to the animal.

17. The method of claim 16 wherein the animal is a human.

18. The method of claim 17 wherein the treatment is an oral treatment.

19. A pharmaceutical composition comprising a compound of claim 14, together with a pharmaceutically acceptable diluent or carrier.

20. A method for the curative or prophylactic treatment of erectile dysfunction in an animal comprising administration of an effective dose of a compound of claim 14, or pharmaceutically acceptable salts and solvates thereof, to the animal.

21. The method of claim 20 wherein the animal is a human.

22. The method of claim 21 wherein the treatment is an oral treatment.

* * * * *

UNITED STATES PATENT AND TRADEMARK OFFICE
CERTIFICATE OF CORRECTION

PATENT NO. : 6,306,870 B1
DATED : October 23, 2001
INVENTOR(S) : Bombrun

It is certified that error appears in the above-identified patent and that said Letters Patent is hereby corrected as shown below:

Title page,
Item [56], OTHER PUBLICATIONS, Bhalla et al., date in parentheses, "(1972)" should be -- (1979) --

Column 1,
Line 9, insert "of" before "International"

Column 2,
Line 7, "$NR^aR_b$" should be --- $NR^aR^b$ --

Column 3,
Lines 63-64, "piperazinyl pyrrolidinyl" should be -- piperazinyl, pyrrolidinyl --
Line 55, "rn" should be -- ring --

Column 4,
Line 26, "bases," should be -- bases. --
Line 35, "-1 one" should be -- -1-one --

Column 5,
Line 45, "Benzyl4" should be -- Benzyl-4 --

Column 6,
Line 13, "(3,4 5-" should be.-- (3,4,5- --
Line 21, "-1, 3, 4, 9tetrahydro" should be -- -1, 3, 4, 9-tetrahydro --
Line 57, "[3oxo-" should be -- [3-oxo- --

Column 7,
Line 7, "(1-Ethylpyrroidin-" should be -- (1-Ethylpyrrolidin- --
Line 14, "carbolin-2-y]" should be -- carbolin-2-yl] --
Line 40, "[3oxo-" should be -- [3-oxo- --
Line 48, "[3oxo-" should be -- [3-oxo- --

Column 8,
Line 15, "[3oxo-" should be -- [3-oxo- --
Line 36, "βcarbolin-2y1]" should be -- βcarbolin-2--yl] --

Column 9,
Line 29, "(2dimethylaminoethoxy)" should be -- (2-dimethylaminoethyoxy) --
Line 30, "dioxin6-yl)" should be -- dioxyin-6-yl) --
Line 31, "-2-yll-" should be -- -2-yl]- --

UNITED STATES PATENT AND TRADEMARK OFFICE
CERTIFICATE OF CORRECTION

PATENT NO. : 6,306,870 B1
DATED : October 23, 2001
INVENTOR(S) : Bombrun

It is certified that error appears in the above-identified patent and that said Letters Patent is hereby corrected as shown below:

Column 13,
Line 62, delete 2nd occurrence of the word "are"

Column 14,
Line 23, "-3-ethylcarbodiumide" should be -- -3-ethylcarbodiimide ---

Column 15,
Line 58, underline the letter "p" in "p-toluene"

Column 16,
Line 25, "4-trifluoromethoxybenzaidehyde" should be
-- 4-trifluoromethoxybenzaldehyde --

Column 17,
Line 57. "3-fluoro4-" should be -- 3-fluoro-4 --

Column 18,
Line 9, "2,34g" should be -- 2.34 g --.

Column 19,
Line 26, " $[\alpha]_D^{19.7}=49$" should be -- $[\alpha]_D^{19.7}=-49$ --
Line 55, "3,4 (s, 3H)" should be -- 3.4 (s, 3H), --
Line 58, "(2-Methoxyethylcarbambyl)" should be -- (2-Methoxyethylcarbamoyl) --

Column 22,
Line 21, "(2,3 g9 42%)" should be -- (2.3 g, 42%) --

Column 23,
Line 56, ")acalic" should be -- (acrylic --

Column 26,
Line 29, delete second occurrence of "solid"
Line 59, "as an a yellow" should be --- as a yellow --

Column 27,
Line 1, "(CDC$_3$," should be -- (CDCl$_3$, --
Line 2, "2,3 (dd, 1H)," should be -- 2.3 (dd, 1H). --
Line 12, "(d 2H)" should be -- (d, 2H) --
Line 22, "(CDCl3," should be -- (CDCl$_3$, --
Line 46, "$^1$NMR" should be -- $^1$H NMR --

UNITED STATES PATENT AND TRADEMARK OFFICE
CERTIFICATE OF CORRECTION

PATENT NO.  : 6,306,870 B1
DATED       : October 23, 2001
INVENTOR(S) : Bombrun

It is certified that error appears in the above-identified patent and that said Letters Patent is hereby corrected as shown below:

Column 28,
Line 27, "phenylprocene-l-one" should be -- phenylpropene-l-one --
Line 36, "Cm$^2$" should be -- cm$^2$ --

Column 29,
Line 23, "H,4,94;" should be -- H, 4.94; --
Line 48, "(4-Method) (phenyl)" should be -- (4-Methoxyphenyl) --

Column 30,
Line 16, "0-1 .3,4,9-" should be -- )-1,3,4,9- --
Line 17, ")progenyl]" should be -- (propenyl] --

Column 31,
Line 9, "(1-Phenyl-" should be -- (1-phenyl-
Line 46, "$C_{27}H22N_2O_3$" should be -- $C_{27}H_{22}N_2O_3$ --

Column 32,
Line 37, "C,72,3;" should be -- C, 72.3; --

Column 33,
Line 34, "carbolin-2-y1]-3-1(" should be -- carbolin-2-yl]-3-1[( --
Line 53, "(E)-4-(3" should be -- (E)-4-[3 --
Line 54, "-2-yll-" should be -- -2-yl]- --

Column 34,
Line 11, "H,4,93N" should be -- H, 4.93; N --
Line 54, "$C_{28}H_2$, " should be -- $C_{28}H_{21}$ --
Line 56, delete second occurrence of the colon ":"

Column 35,
Line 31, "Zhumal" should be -- Zhurnal --

Column 36,
Line 12, "(E)-N-Benzyl4-" should be -- (E)-N-Benzyl-4- --
Line 46, "(E)-3-methoxy4-" should be -- (E)-3-methoxy-4- --
Line 48, "EtOH:H2O" should be -- EtOH:H$_2$O --

Column 37,
Line 45, delete second occurrence of ":"
Line 61, "-2-yl-" should be -- -2-yl]- --

UNITED STATES PATENT AND TRADEMARK OFFICE
CERTIFICATE OF CORRECTION

PATENT NO. : 6,306,870 B1
DATED : October 23, 2001
INVENTOR(S) : Bombrun

It is certified that error appears in the above-identified patent and that said Letters Patent is hereby corrected as shown below:

Column 38,
Line 13, "C30H$_{27}$N$_3$O$_4$" should be -- C$_{30}$H$_{27}$N$_3$O$_4$ --
Line 36, "carbolin-2-yll]" should be -- carbolin-2-yl] --
Line 41, "MP;" should be -- MP: --
Line 47, ")6-fluoro-" should be -- )-6-fluoro- --
Line 51, delete second occurrence of "and"
Line 57, "H,4,95;" should be -- H, 4.95; --
Line 58, "H,4,91;" should be -- H, 4.91; --

Column 39,
Line 14, "C,72,33;" should be -- C, 72.33; --
Line 16, ")6-fluoro-" should be -- )-6-fluoro- --

Column 40,
Line 37, "Tlc" should be -- T/c

Column 42,
Line 21, "-3-3-(3-(4-" should be -- -3-(3-(4- --

Column 43,
Line 33, "4carboxylic" should be -- 4-carboxylic --
Line 62, "Jstarting" should be -- starting --

Column 45,
Line 67, "tic" should be -- tlc --

Column 49,
Line 12-- " -(4-methyliminomethylphenyl) " should be -- -(4-methylaminomethylphenyl) --
Line 6, "C,73,4;" should be -- C, 73.4; --

Column 51,
Line 66, "H,5.34;" should be -- H, 6.34; --

Column 54,
Line 27, "H,9,89;" should be -- H, 5.85; --

UNITED STATES PATENT AND TRADEMARK OFFICE
CERTIFICATE OF CORRECTION

PATENT NO.    : 6,306,870 B1
DATED         : October 23, 2001
INVENTOR(S)   : Bombrun It is certified that error appears in the above-identified patent and that said Letters Patent is hereby corrected as shown below:

Column 55,
Line 31, "DCM:cyclohemane" should be -- DCM:cyclohexane --

Column 60,
Line 27, "(E)4-" should be -- (E)4 --

Column 63,
Line 49, "intermediate 20" should be -- Intermediate 20 --

Column 64,
Line 7, "H,8.08;" should be -- H, 6.08; --

Column 70,
Line 4, "-O-$C_{1-4}$" should be -- -O-$C_{2-4}$ --
Lines 16-17, delete second occurrence of "a propylene chain"

Signed and Sealed this

Twenty-second Day of April, 2003

JAMES E. ROGAN
*Director of the United States Patent and Trademark Office*